(12) United States Patent
Brown et al.

(10) Patent No.: US 8,772,293 B2
(45) Date of Patent: Jul. 8, 2014

(54) CHEMICAL COMPOUNDS

(75) Inventors: Alan Daniel Brown, Sandwich (GB); Marcel John De Groot, Sandwich (GB); Brian Edward Marron, Durham, NC (US); David James Rawson, Sandwich (GB); Thomas Ryckmans, Sandwich (GB); Robert Ian Storer, Sandwich (GB); Paul Anthony Stupple, Sandwich (GB); Nigel Alan Swain, Sandwich (GB); Christopher William West, Durham, NC (US)

(73) Assignees: Pfizer Limited, Sandwich (GB); Icagen Inc., Durham, NC (US)

( * ) Notice: Subject to any disclaimer, the term of this patent is extended or adjusted under 35 U.S.C. 154(b) by 397 days.

(21) Appl. No.: 13/178,534

(22) Filed: Jul. 8, 2011

(65) Prior Publication Data
US 2012/0010182 A1   Jan. 12, 2012

Related U.S. Application Data

(60) Provisional application No. 61/362,927, filed on Jul. 9, 2010, provisional application No. 61/492,525, filed on Jun. 2, 2011.

(51) Int. Cl.
| | | |
|---|---|---|
| *A01N 43/58* | (2006.01) | |
| *A61K 31/50* | (2006.01) | |
| *A01N 43/40* | (2006.01) | |
| *A61K 31/435* | (2006.01) | |
| *A01N 43/56* | (2006.01) | |
| *A61K 31/415* | (2006.01) | |
| *A01N 43/36* | (2006.01) | |
| *A61K 31/40* | (2006.01) | |

(52) U.S. Cl.
USPC ............ 514/247; 514/277; 514/403; 514/408

(58) Field of Classification Search
CPC ... A61K 31/10; A61K 31/145; A61K 31/075; A61K 31/085
USPC .................................. 514/247, 277, 403, 408
See application file for complete search history.

(56) References Cited

U.S. PATENT DOCUMENTS

| | | |
|---|---|---|
| 5,084,085 A | 1/1992 | Theodoridis |
| 5,851,745 A | 12/1998 | Takeuchi |
| 5,885,304 A | 3/1999 | Schneider et al. |
| 6,118,016 A | 9/2000 | Hawkins |
| 6,251,827 B1 | 6/2001 | Ziemer et al. |
| 6,335,333 B1 | 1/2002 | Schwab et al. |
| 6,348,474 B1 | 2/2002 | Kayakiri et al. |
| 6,376,512 B1 | 4/2002 | Jayyosi et al. |
| 7,772,285 B2 | 8/2010 | Chaki et al. |
| 2002/0086887 A1 | 7/2002 | Augeri et al. |
| 2003/0162818 A1 | 8/2003 | Ikawa et al. |
| 2008/0188467 A1 | 8/2008 | Wong et al. |
| 2010/0179137 A1 | 7/2010 | Kamikubo et al. |
| 2011/0201616 A1 | 8/2011 | Kubota et al. |
| 2012/0010183 A1 | 1/2012 | Bell et al. |
| 2012/0010207 A1 | 1/2012 | Bell et al. |
| 2013/0109667 A1 | 5/2013 | Markworth et al. |
| 2013/0109696 A1 | 5/2013 | Greener et al. |
| 2013/0109701 A1 | 5/2013 | Brown et al. |
| 2013/0109708 A1 | 5/2013 | Brown et al. |
| 2013/0116285 A1 | 5/2013 | Bell et al. |

FOREIGN PATENT DOCUMENTS

| | | |
|---|---|---|
| EP | 0029742 | 6/1981 |
| EP | 0194599 | 9/1986 |
| EP | 0281103 | 9/1988 |
| EP | 0325245 | 7/1989 |
| EP | 0399732 | 11/1990 |
| EP | 0412848 | 2/1991 |
| EP | 0453210 | 10/1991 |
| EP | 0570006 | 11/1993 |
| EP | 0585155 | 3/1994 |
| EP | 0620490 | 10/1994 |
| EP | 0684521 | 11/1995 |
| EP | 0753508 | 1/1997 |
| EP | 1260221 A2 | 11/2002 |
| GB | 2266527 | 11/1993 |

(Continued)

OTHER PUBLICATIONS

Naganawa et al., "Further optimization of sulfonamide analogs as EP1 receptor antagonists: Synthesis and evaluation of bioisosteres for the carboxylic acid group", Bioorganic & Medicinal Chemistry, vol. 14(21), pp. 7121-7137 (2006).

(Continued)

*Primary Examiner* — Yong Chong
(74) *Attorney, Agent, or Firm* — J. Michael Dixon

(57) ABSTRACT

The invention relates to sulfonamide derivatives, to their use in medicine, to compositions containing them, to processes for their preparation and to intermediates used in such processes.

More particularly the invention relates to new sulfonamide Nav1.7 inhibitors of formula (I):

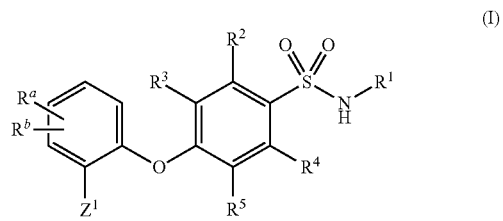

or pharmaceutically acceptable salts thereof, wherein $Z^1$, $R^a$, $R^b$, $R^1$, $R^2$, $R^3$, $R^4$ and $R^5$ are as defined in the description.

Nav 1.7 inhibitors are potentially useful in the treatment of a wide range of disorders, particularly pain.

15 Claims, No Drawings

(56) References Cited

FOREIGN PATENT DOCUMENTS

| | | |
|---|---|---|
| JP | 5289262 | 11/1993 |
| JP | 5307242 | 11/1993 |
| JP | 2001075213 | 3/2001 |
| WO | 8801133 | 2/1988 |
| WO | 8904303 | 5/1989 |
| WO | 8904304 | 5/1989 |
| WO | 8904305 | 5/1989 |
| WO | 8912628 | 12/1989 |
| WO | 9300332 | 1/1993 |
| WO | 9413636 | 6/1994 |
| WO | 9421590 | 9/1994 |
| WO | 9610012 A1 | 4/1995 |
| WO | 9604905 | 2/1996 |
| WO | 9609818 | 4/1996 |
| WO | 9900372 | 1/1999 |
| WO | 9916744 | 4/1999 |
| WO | 9920275 | 4/1999 |
| WO | 9932433 A1 | 7/1999 |
| WO | 9947508 | 9/1999 |
| WO | 0039077 | 7/2000 |
| WO | 0064876 | 11/2000 |
| WO | 0066120 | 11/2000 |
| WO | 0071493 A2 | 11/2000 |
| WO | 0071507 A2 | 11/2000 |
| WO | 0071508 A2 | 11/2000 |
| WO | 0071509 A1 | 11/2000 |
| WO | 0071510 A2 | 11/2000 |
| WO | 0071511 A2 | 11/2000 |
| WO | 0071512 A1 | 11/2000 |
| WO | 0123347 A1 | 4/2001 |
| WO | 0127068 A1 | 4/2001 |
| WO | 0136365 | 5/2001 |
| WO | 0166098 | 9/2001 |
| WO | 0224636 | 3/2002 |
| WO | 02096863 A1 | 12/2002 |
| WO | 03042150 | 5/2003 |
| WO | 2004018386 | 3/2004 |
| WO | 2004037233 A2 | 5/2004 |
| WO | 2004078126 A2 | 9/2004 |
| WO | 2005080346 | 9/2005 |
| WO | 2005094810 | 10/2005 |
| WO | 2005113494 A2 | 12/2005 |
| WO | 2006015158 | 2/2006 |
| WO | 2006045514 | 5/2006 |
| WO | 2006121097 | 11/2006 |
| WO | 2007068894 A2 | 6/2007 |
| WO | 2007072782 | 6/2007 |
| WO | 2007115408 A1 | 10/2007 |
| WO | 2007115409 A1 | 10/2007 |
| WO | 2007115410 A1 | 10/2007 |
| WO | 2008025539 | 3/2008 |
| WO | 2008092231 | 8/2008 |
| WO | 2008149965 | 11/2008 |
| WO | 2009/012242 A2 | 1/2009 |
| WO | 2009012242 A2 | 1/2009 |
| WO | 2009/049181 A1 | 4/2009 |
| WO | 2009064250 | 5/2009 |
| WO | 2009064251 | 5/2009 |
| WO | 2009067541 | 5/2009 |
| WO | 2009067621 | 5/2009 |
| WO | 2009080835 | 7/2009 |
| WO | 2009101082 A1 | 8/2009 |
| WO | 2009139633 A1 | 11/2009 |
| WO | 2009139634 A1 | 11/2009 |
| WO | 2009144159 A1 | 12/2009 |
| WO | 2009157399 | 12/2009 |
| WO | 2010/079443 | 7/2010 |
| WO | 2010079443 A1 | 7/2010 |

OTHER PUBLICATIONS

Pinkerton et al., "Allosteric potentiators of the metabotropic glutamate receptor 2 (mGlu2). Part 3: Identification and biological activity of indanone containing mGlu2 receptor potentiators", Bioorganic & Medicinal Chemistry Letters, vol. 15(6), pp. 1565-1571 (2005).

Ng et al., "Design, Synthesis, and Biological Activity of Novel Factor Xa Inhibitors: 4-Aryloxy Substituents of 2,6-Diphenoxypyridines", Bioorganic & Medicinal Chemistry, vol. 10(3), pp. 657-666 (2002).

Hamill et al., "Development of [11C]L-159,884: A Radiolabelled, Nonpeptide Angiotensin II Antagonist that is Useful for Angiotensin II, AT1 Receptor Imaging", Applied Radiation and Isotopes, vol. 47(2), pp. 211-218 (1996).

Matassa et al., "Synthesis and in Vitro LTD4 Antagonist Activity of Bicyclic and Monocyclic Cyclopentylurethane and Cyclopentylacetamide N-Arylsulfonyl Amides", Journal of Medicinal Chemistry, vol. 33(9), pp. 2621-2629 (1990).

Musser et al., "N-[(Arylmethoxy)phenyl] Carboxylic Acids, Hydroxamic Acids, Tetrazoles, and Sulfonyl Carboxamides. Potent Orally Active Leukotriene D4 Antagonists of Novel Structure", Journal of Medicinal Chemistry, vol. 33(1), pp. 240-245 (1990).

Brown et al., "Hydroxyacetophenone-Derived Antagonists of the Peptidoleukotriens", Journal of Medicinal Chemistry, vol. 32(4), pp. 807-826 (1989).

Dubois et al., "Dihydrochalcone Sweeteners. A Study of the Atypical Temporal Phenomena", Journal of Medicinal Chemistry, Vol. 24(4), pp. 408-428 (1981).

Sobel et al., Journal of Chromatography Biomedical Applications, vol. 183(1), pp. 124-130 (1980).

Silverman, Richard B. The Organic Chemistry of Drug Design and Drug Action. 2nd Ed., 2004, pp. 29-32, Elsevier, Burlington, MA.

CHEMICAL COMPOUNDS

This application claims benefit of U.S. Provisional Application No. 61/362,927, filed Jul. 9, 2010; and U.S. Provisional Application No. 61/492,525, filed Jun. 2, 2011; each application is hereby incorporated by reference in its entirety for any purpose.

The invention relates to sulfonamide derivatives, to their use in medicine, to compositions containing them, to processes for their preparation and to intermediates used in such processes.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)).

There are currently at least nine known members of the family of voltage-gated sodium channel (VGSC) alpha subunits. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that $Na_v1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v1.7$ protein has been shown to accumulate in neuromas, particularly painful neuromas (Kretschmer et al., *Acta. Neurochir. (Wien)*, 144(8): 803-10 (2002)). Gain of function mutations of $Na_v1.7$, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology*. 7; 69(6): 505-7 (2007)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.*; 52(5):767-74 (2006). Further evidence of the role of Nav1.7 in pain is found in the phenotype of loss of function mutations of the SCN9A gene. Cox and colleagues (*Nature*, 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.*; 71(4): 311-9 (2007), Ahmad et al, *Hum Mol. Genet.* 1; 16(17): 2114-21 (2007)).

Nav 1.7 inhibitors are therefore potentially useful in the treatment of a wide range of disorders, particularly pain, including: acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

Certain inhibitors of voltage gated sodium channels useful in the treatment of pain are known. Thus WO-A-2005/013914 discloses heteroarylamino sulfonylphenyl derivatives, WO-A-2008/118758 aryl sulphonamides and WO-A-2009/012242 N-thiazolyl benzenesulfonamides.

There is, however, an ongoing need to provide new $Na_v1.7$ inhibitors that are good drug candidates.

Preferably compounds are selective Nav1.7 channel inhibitors. That is, preferred compounds show an affinity for the Nav1.7 channel over other Nav channels. In particular, they should show an affinity for the Nav1.7 channel which is greater than their affinity for Nav1.5 channels. Advantageously, compounds should show little or no affinity for the Nav1.5 channel.

Selectivity for the Nav1.7 channel over Nav1.5 may potentially lead to one or more improvements in side-effect profile. Without wishing to be bound by theory, such selectivity is thought to reduce any cardiovascular side effects which may be associated with affinity for the Nav1.5 channel. Preferably compounds demonstrate a selectivity of 10-fold, more preferably 30-fold, most preferably 100-fold, for the Nav 1.7 channel when compared to their selectivity for the Nav1.5 channel whilst maintaining good potency for the Nav1.7 channel.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as Nav1.7 channel inhibitors. They should be non-toxic and demonstrate few side-effects. Ideal drug candidates should exist in a physical form that is stable, non-hygroscopic and easily formulated.

We have now found new sulphonamide Nav1.7 inhibitors.

According to a first aspect of the invention there is provided a compound of formula (I)

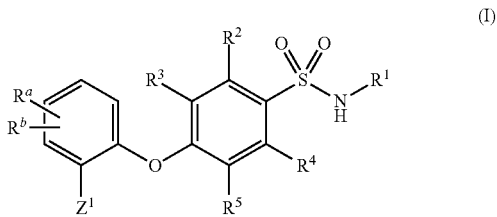

or a pharmaceutically acceptable salt thereof, wherein:

$R^1$ is a 'C-linked' 5- or 6-membered heteroaryl comprising (a) one or two nitrogen atoms or, when 5-membered, (b) one or two nitrogen atoms and one sulphur atom, said heteroaryl being optionally substituted on a ring carbon atom by F or Cl;

$R^2$, $R^3$ and $R^4$ are independently H, F, Cl or —OCH$_3$;

$R^5$ is CN, F, Cl or $R^6$;

$R^a$ is (a) phenyl, optionally substituted by one to three substituents independently selected from F, Cl, CN, H$_2$N(C$_1$-C$_4$)alkylene-, (C$_1$-C$_4$)alkylNH(C$_1$-C$_4$)alkylene-(C$_3$-C$_8$)cycloalkyl or $R^6$; or (b) a 'C-linked' 5- or 6-membered heteroaryl comprising one or two nitrogen atoms, said heteroaryl being optionally substituted by $R^7$ or $R^8$, or both $R^7$ and $R^8$;

$R^b$ is H, F, Cl, CN or $R^6$;

$R^6$ is (C$_1$-C$_4$)alkyl or (C$_1$-C$_4$)alkyloxy, each optionally substituted by, valency permitting, one to eight F;

$Z^1$ is (a) phenyl, optionally substituted by one to three substituents independently selected from F, Cl or $R^6$; or (b) a 'C-linked' 5- or 6-membered heteroaryl comprising one or two nitrogen atoms, said heteroaryl being optionally substituted by $R^7$ or $R^8$, or both $R^7$ and $R^8$;

$R^7$ is attached to a $Z^1$ ring carbon and is selected from F, Cl, NR$^9$R$^{10}$, $R^6$, (C$_3$-C$_8$)cycloalkyl or Het$^1$;

$R^8$ is attached to a $Z^1$ ring nitrogen and is selected from (a) (C$_1$-C$_4$)alkyl or (C$_3$-C$_8$)cycloalkyl, each optionally substituted by, valency permitting, one to three F; or (b) 'C-linked' Het$^1$;

Het$^1$ is a 3- to 8-membered saturated monoheterocycloalkyl comprising one or two ring members selected from —NR$^{11}$— and —O—, said monoheterocycloalkyl being optionally substituted on a ring carbon atom by one to three substituents independently selected from F, (C$_1$-C$_6$)alkyl, (C$_1$-C$_4$)alkyloxy(C$_0$-C$_4$)alkylene and (C$_3$-C$_8$)cycloalkyl; and $R^9$, $R^{10}$ and $R^{11}$ are independently selected from H, (C$_1$-C$_6$)alkyl or (C$_3$-C$_8$)cycloalkyl; or, when Het$^1$ is 'N-linked', $R^{11}$ is absent from that nitrogen atom.

Described below are a number of embodiments (E) of this first aspect of the invention, where for convenience E1 is identical thereto.

E1 A compound of formula (I) as defined above or a pharmaceutically acceptable salt thereof.

E2 A compound according to E1 of the following formula

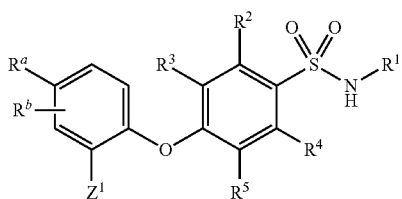

or a pharmaceutically acceptable salt thereof, wherein:

$R^1$ is a 'C-linked' 5- or 6-membered heteroaryl comprising (a) one or two nitrogen atoms or, when 5-membered, (b) one or two nitrogen atoms and one sulphur atom, said heteroaryl being optionally substituted on a ring carbon atom by F or Cl;

$R^2$, $R^3$ and $R^4$ are independently H, F, Cl or —OCH$_3$;

$R^5$ is CN, F, Cl or $R^6$;

$R^a$ is phenyl optionally substituted by one to three substituents independently selected from F, Cl or $R^6$;

$R^b$ is H, F, Cl or $R^6$;

$R^6$ is (C$_1$-C$_4$)alkyl or (C$_1$-C$_4$)alkyloxy, each optionally sustituted by one to three F;

$Z^1$ is (a) phenyl, optionally substituted by one to three substituents independently selected from F, Cl or $R^6$; or (b) a 'C-linked' 5- or 6-membered heteroaryl comprising one or two nitrogen atoms, said heteroaryl being optionally substituted by $R^7$ or $R^8$, or both $R^7$ and $R^8$;

$R^7$ is attached to a $Z^1$ ring carbon and is selected from F, Cl, NR$^9$R$^{10}$, $R^6$, (C$_3$-C$_8$)cycloalkyl or Het$^1$;

$R^8$ is attached to a $Z^1$ ring nitrogen and is from (C$_1$-C$_4$)alkyl, (C$_3$-C$_8$)cycloalkyl or 'C-linked' Het$^1$;

Het$^1$ is a 3- to 8-membered saturated monoheterocycloalkyl comprising one or two ring members selected from —NR$^{11}$— and —O—, said monoheterocycloalkyl being optionally substituted on a ring carbon atom by one to three substituents independently selected from F, (C$_1$-C$_6$)alkyl, (C$_1$-C$_4$)alkyloxy(C$_0$-C$_4$)alkylene and (C$_3$-C$_8$)cycloalkyl; and $R^9$, $R^{19}$ and $R^{11}$ are independently selected from H, (C$_1$-C$_6$)alkyl or (C$_3$-C$_8$)cycloalkyl; or, when Het$^1$ is 'N-linked', $R^{11}$ is absent from that nitrogen atom.

E3 A compound according to E1 or E2 wherein $R^1$ is a 'C-linked' heteroaryl selected from thiazolyl, thiadiazolyl, pyridazinyl or pyrimidinyl, said heteroaryl being optionally substituted on a ring carbon atom by F or Cl.

E4 A compound according to any of E1 to E3 wherein $R^1$ is a 'C-linked' heteroaryl selected from thiazolyl or thiadiazolyl, said heteroaryl being optionally substituted by on a ring carbon atom F.

E5 A compound according to any of E1 to E4 wherein $R^1$ is 'C-linked' thiadiazolyl, such as 'C-linked' 1,3,4-thiadiazolyl.

E6 A compound according to any of E1 to E5 wherein $R^2$, $R^3$ and $R^4$ are independently H or F.

E7 A compound according to any of E1 to E6 wherein $R^2$, is H or F; and $R^3$ and $R^4$ are both H.

E8 A compound according to any of E1 to E7 wherein $R^5$ is CN, F or Cl.

E9 A compound according to any of E1 to E8 wherein $R^5$ is CN or Cl.

E10 A compound according to any of E1 to E9 wherein $R^a$ is phenyl, optionally substituted by $R^6$.

E11 A compound according to any of E1 to E10 wherein $R^a$ is phenyl optionally substituted by Cl or CF$_3$.

E12 A compound according to any of E1 to E11 wherein $R^b$ is H.

E13 A compound according to any of E1 to E12 wherein $Z^1$ is a 'C-linked' 5- or 6-membered heteroaryl comprising one or two nitrogen atoms, said heteroaryl being optionally substituted by $R^7$ or $R^8$, or both $R^7$ and $R^8$.

E14 A compound according to any of E1 to E13 wherein $Z^1$ is a 'C-linked' heteroaryl selected from pyrazolyl and pyridazinyl, said heteroaryl being optionally substituted by $R^7$ or $R^8$, or both $R^7$ and $R^8$.

E15 A compound according to any of E1 to E13 wherein $Z^1$ is a 'C-linked' 5- or 6-membered heteroaryl comprising one or two nitrogen atoms, said heteroaryl being optionally substituted by $R^8$.

E16 A compound according to any of E1 to E13 or E15 wherein $Z^1$ is a 'C-linked' 5- or 6-membered heteroaryl comprising one or two nitrogen atoms, said heteroaryl being optionally substituted by methyl or a 'C-linked' 3- to 6-membered saturated monoheterocycloalkyl comprising one or two ring members selected from NH or —N(C$_1$-C$_4$)alkyl.

E17 A compound according to any of E1 to E14 wherein $Z^1$ is a 'C-linked' heteroaryl selected from pyrazolyl and pyridazinyl, said heteroaryl being optionally substituted by $R^8$.

E18 A compound according to any of E1 to E14 or E17 wherein $Z^1$ is a 'C-linked' heteroaryl selected from pyrazolyl and pyridazinyl, said heteroaryl being optionally substituted by methyl or a 'C-linked' 3- to 6-membered saturated monoheterocycloalkyl comprising one or two ring members selected from NH or —N($C_1$-$C_4$)alkyl.

E19 A compound according to any of E1 to E14 or E17 to E18 wherein $Z^1$ is a 'C-linked' pyridazinyl or 'C-linked' pyrazolyl, said pyrazolyl being optionally substituted by methyl or a 'C-linked' 3- to 4-membered saturated monoheterocycloalkyl comprising one —N($C_1$-$C_2$)alkyl ring member.

E20 A compound according to E1 which is the compound of any one of:
Examples 1 to 20;
4-{[3'-(aminomethyl)-3-(1-methyl-1H-pyrazol-5-yl)biphenyl-4-yl]oxy}-3-cyano-N-(1,3-thiazol-2-yl)benzenesulfonamide;
Example 22;
3-cyano-4-({2'-[(methylamino)methyl]-3-(1-methyl-1H-pyrazol-5-yl)biphenyl-4-yl}oxy)-N-(1,3-thiazol-2-yl) benzenesulfonamide;
Examples 24 to 33;
5-Chloro-2-fluoro-4-({3-[2-(piperazin-1-yl)pyridin-4-yl]-4'-(trifluoromethyl)biphenyl-4-yl}oxy)-N-(1,3,4-thiadiazol-2-yl)benzenesulfonamide; or
Examples 35 to 40;
or a pharmaceutically acceptable salt thereof.

Alkyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

Examples of cycloalkyl include cyclopropyl, cyclobutyl, cyclopentyl, cyclohexyl, cycloheptyl and cyclooctyl.

Halo means fluoro, chloro, bromo or iodo.

The term 'C-linked' used in the definitions of formula (I) means that the group in question is joined via a ring carbon. The term 'N-linked' used in the definitions of formula (I) means that the group in question is joined via a ring nitrogen.

Specific examples of 5- or 6-membered heteroaryl used in the definitions of formula (I) include pyrrolyl, pyrazolyl, imidazoyl, thiazolyl, isothiazolyl, thiadiazolyl, pyridyl, pyridazinyl, pyrimidinyl and pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of $Het^1$ include oxiranyl, aziridinyl, oxetanyl, azetidinyl, tetrahydrofuranyl, pyrrolidinyl, tetrahydropyranyl, piperidinyl, morpholinyl, piperazinyl, azepanyl, oxepanyl, oxazepanyl and diazepinyl.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)_3$) polar head group. For more information, see *Crystals and the Polarizing Microscope* by N. H. Hartshorne and A. Stuart, 4th Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino groups. The protecting groups used in the preparation of the compounds of the invention may be used in conventional manner. See, for example, those described in 'Greene's Protective Groups in Organic Synthesis' by Theodora W Greene and Peter G M Wuts, fourth edition, (John Wiley and Sons, 2006), in particular chapter 7 ("Protection for the Amino Group"), incorporated herein by reference, which also describes methods for the removal of such groups.

In the following general methods, $R^1$, $R^2$, $R^3$, $R^4$, $R^5$, $R^a$, $R^b$ and $Z^1$ are as previously defined for a derivative of the formula (I) unless otherwise stated. $Pg^1$ is a suitable amino protecting group, such as dimethoxybenzyl, methoxymethyl or ethoxyethyl. $Pg^2$ is H or is a suitable hydroxy protecting group, such as methoxy or benzyl. Lg is a suitable leaving group, such as halo (e.g. Br) or a sulphonate ester (e.g mesylate). M is an optionally substituted/ligated metal or boron group suitable for cross coupling reactions, such as trialkylstannane, dihydroxyborane, dialkoxyborane or halozinc.

Where ratios of solvents are given, the ratios are by volume.

According to a first process, compounds of formula (I) may be prepared by the process illustrated in Scheme 1.

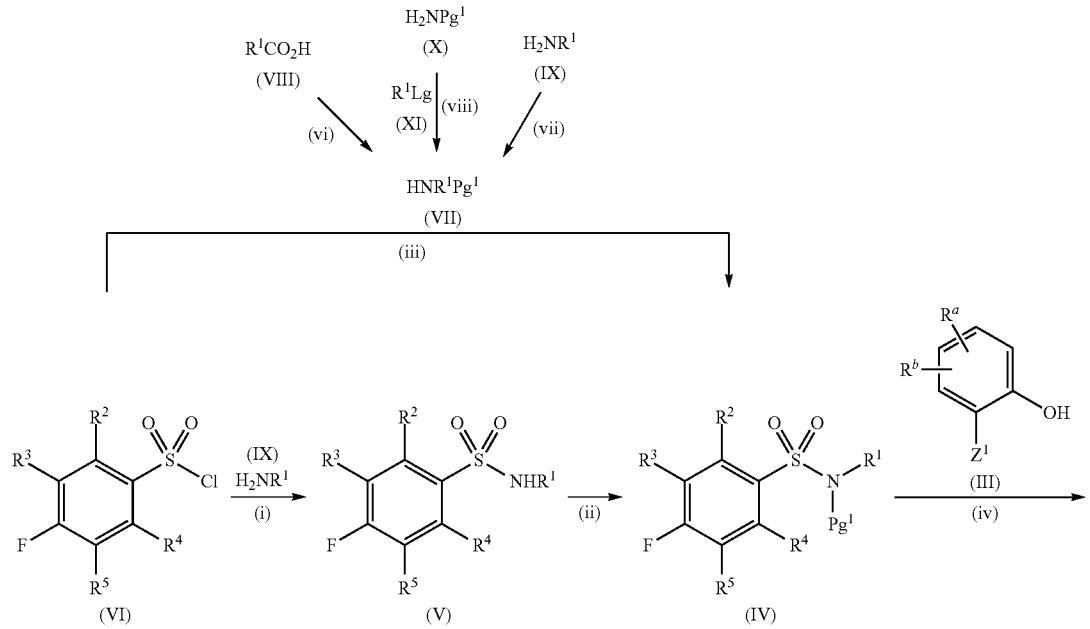

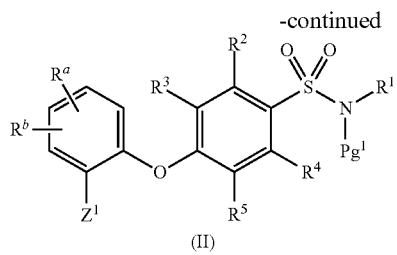 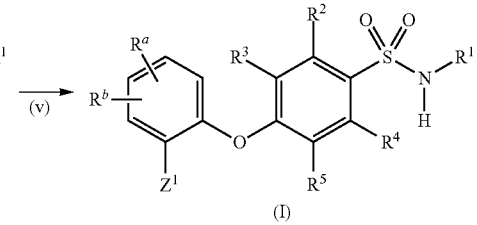

Compounds of formula (I) can be prepared from compounds of formula (II) according to reaction step (v) by deprotection methods under acidic conditions. Suitable acids include HCl, formic acid or trifluoroacetic acid. Preferred methods comprise HCl in 1,4-dioxane at room temperature.

Compounds of formula (II) can be prepared from compounds of formula (IV) according to reaction step (iv) by nucleophilic aromatic substitution reaction with a phenol of formula (III) under basic reaction conditions. Suitable conditions include potassium carbonate in DMF or DMSO, sodium hydride in NMP or DMF, sodium hydroxide or potassium hydroxide in 1,4-dioxane and water or DMSO or potassium tert-butoxide in THF at from room temperature to 150° C. Preferred conditions comprise 2 equivalents of potassium carbonate in DMSO at room temperature.

Compounds of formula (III) are either commercially available or can be prepared according to Schemes 5 and 6.

Compounds of formula (IV) can be prepared from compounds of formula (VI) according to reaction step (iii) by displacement of a sulfonyl chloride with compounds of formula (VII) under basic reaction conditions. Typical conditions comprise lithium hexamethyldisilazane in THF at −78° C.

Alternatively compounds of formula (IV) can be prepared from compounds of formula (V) according to reaction step (ii) by introduction of protecting group Pg1, such as dimethoxybenzyl or methoxymethyl, under basic reaction conditions or Mitsunobu conditions. Preferred conditions comprise N,N-diisopropylethylamine in dichloromethane at room temperature.

Compounds of formula (V) can be prepared from compounds of formula (VI) according to reaction step (i) by displacement of a sulfonyl chloride under basic reaction conditions with compounds of formula (IX), for example lithium hexamethyldisilazane, diazabicyclo(2.2.2)octane, triethylamine, NaOH or pyridine. Preferred conditions comprise NaOH in 1,4-dioxane and water at room temperature.

Compounds of formula (VII) can be prepared from compounds of formula (VIII) according to reaction step (vi) by Curtius rearrangement through generation of an acyl azide using diphenylphosphoryl azide.

Alternatively compounds of formula (VII) may be prepared from compounds of formula (IX) according to reaction step (vii) through the processes outlined for reaction step (ii) or by reductive amination with an aldehyde. Typical reaction conditions comprise dimethoxybenzaldehyde in toluene at 110° C. followed by reduction with sodium borohydride.

Alternatively compounds of formula (VII) may be prepared from compounds of formula (X) according to reaction step (viii) by nucleophilic aromatic substitution reaction on compounds of formula (XI). Typical reaction conditions comprise triethylamine in ethanol under microwave irradiation at 120° C. for 15 minutes.

According to a second process, compounds of formula (I) may be prepared by the process illustrated in Scheme 2.

Scheme 2

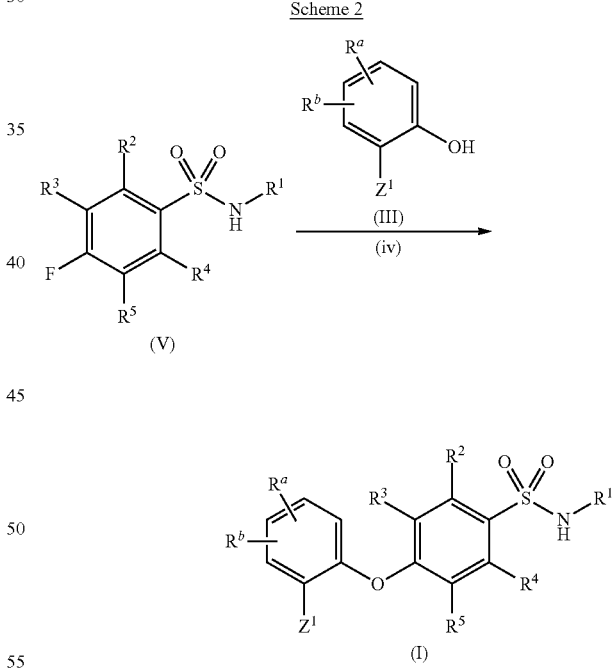

Compounds of formula (I) can be prepared from compounds of formula (V) by nucleophilic aromatic substitution reaction with compounds of formula (III) according to process step (iv), under conditions described above for Scheme 1 step (iv). Preferred conditions comprise potassium carbonate in dimethylformamide at 80-100° C.

According to a third process, compounds of formula (I) may be prepared by the process illustrated in Scheme 3.

Scheme 3

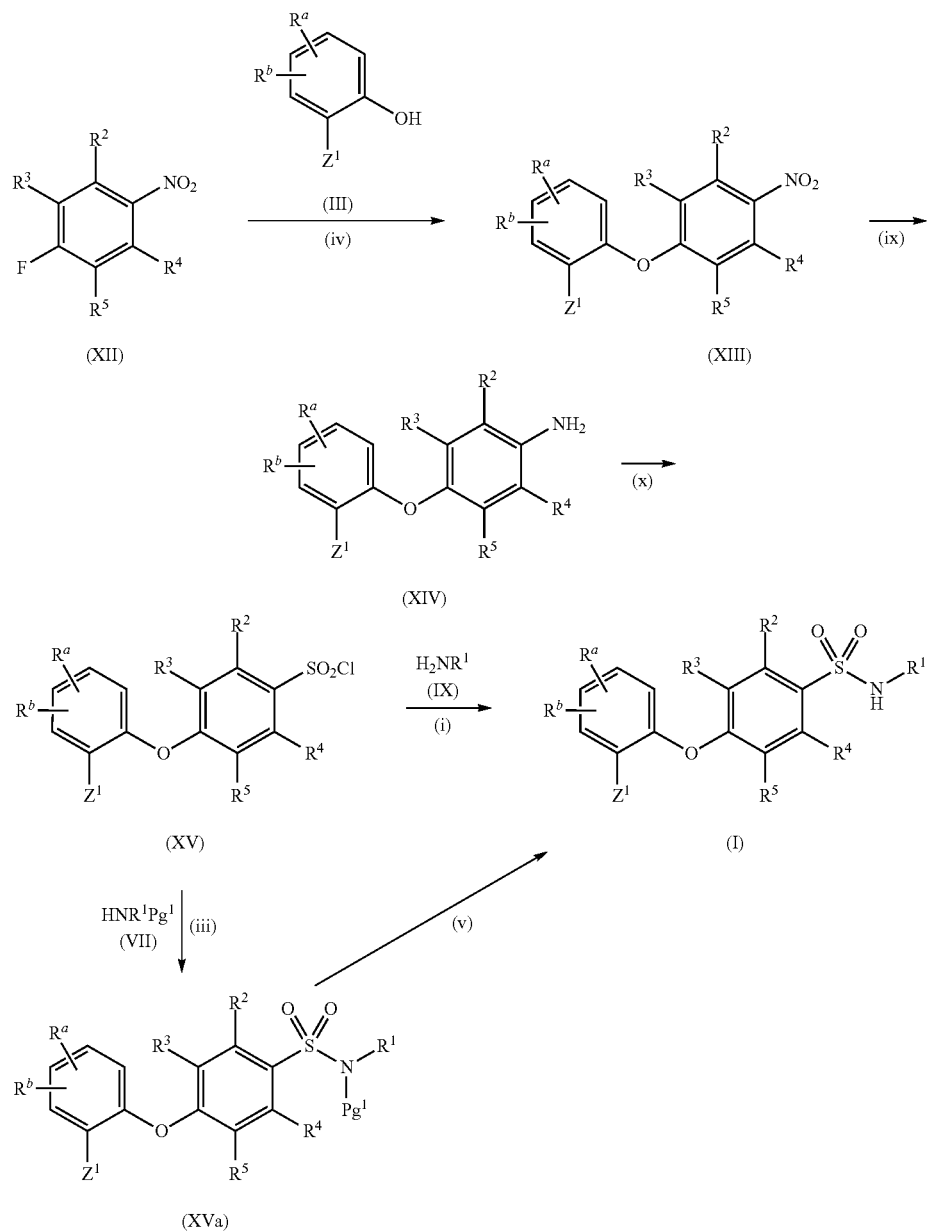

Compounds of formula (I) can be prepared from compounds of formula (XV) by reaction according to process step (i) by displacement of a sulfonyl chloride with compounds of formula (IX) under basic reaction conditions, such as those described above for Scheme 1 step (i).

Alternatively compounds of formula (I) can be prepared from compounds of formula (XV) by reaction according to process step (iii) by displacement of a sulfonyl chloride under basic reaction conditions with compounds of formula (VII) to yield compounds of formula (XVa), followed by a deprotection according to step (v) under conditions described above for Scheme 1 step (v).

Compounds of formula (XV) can be prepared from compounds of formula (XIV) according to process step (x) by a Sandmeyer reaction. Typical conditions comprise sodium nitrite in HCl, acetic acid and water, followed by sulfur dioxide in acetic acid with copper chloride at 0° C.

Compounds of formula (XIV) can be prepared from compounds of formula (XIII) by a reduction reaction according to process step (ix), for example hydrogenation, a suitable metal reduction or use of sodium dithionite. Preferred conditions comprise calcium chloride in the presence of iron in ethanol/water.

Compounds of formula (XIII) can be prepared from compounds of formula (XII) by nucleophilic aromatic substitution reaction with compounds of formula (III) according to process step (iv), as described above for Scheme 1 step (iv). Preferred conditions comprise potassium carbonate in dimethylformamide at 0° C.

According to a fourth process, compounds of formula (I) may be prepared by the process illustrated in Scheme 4.

Scheme 4

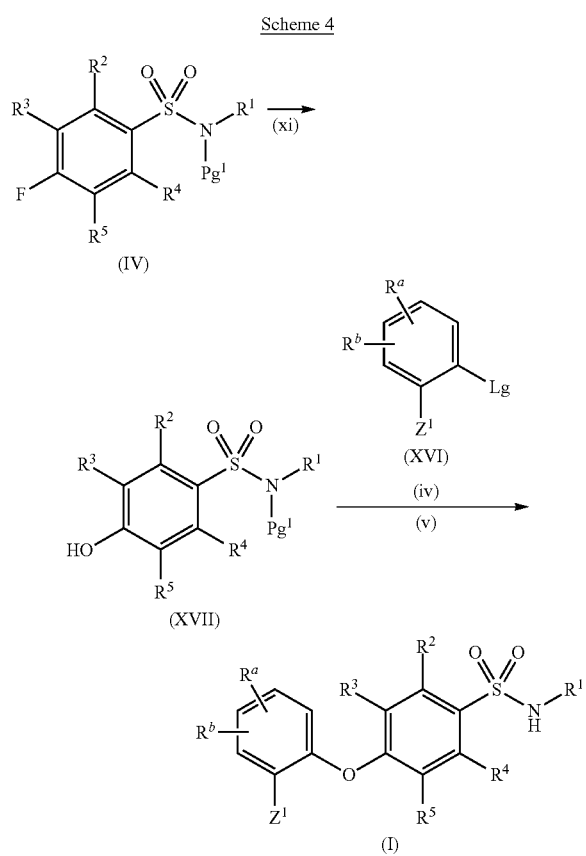

Compounds of formula (I) may be prepared from compounds of formulae (XVI) and (XVII) according to process step (iv) followed by process step (v), under conditions described in Scheme 1 steps (iv) and (v).

Compounds of formula (XVII) can be prepared from compounds of formula (IV) according to process step (xi) by nucleophilic aromatic substitution reaction under basic conditions. Preferred conditions comprise potassium tert-butoxide in THF followed by a suitable acid deprotection such as HCl in dioxane, or trimethylsilylethanol and potassium carbonate in DMSO at room temperature.

According to a fifth process, compounds of formula (III) may be prepared by the process illustrated in Scheme 5.

Scheme 5

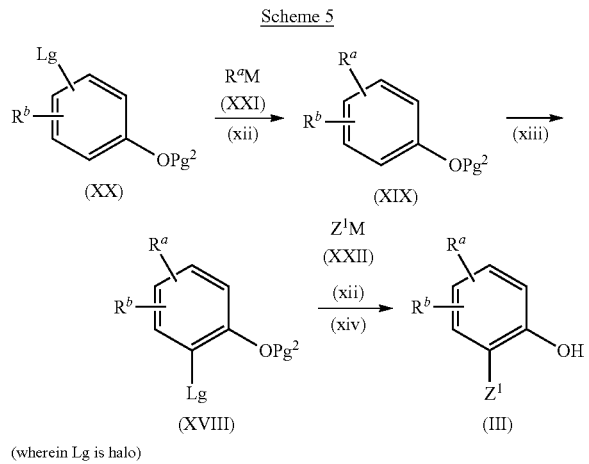

(wherein Lg is halo)

Compounds of formula (III) can be prepared by cross-coupling compounds of formula (XVIII) with compounds formula (XXII) according to process step (xii), followed, as appropriate, by deprotection of any protecting group present according to process step (xiv).

Cross-coupling is conveniently effected in the presence of a suitable catalyst system (e.g. palladium or nickel) and base. Typical Suzuki coupling conditions comprise 1.2-3 equivalents of boronic acid, and 0.01-0.25 equivalents of palladium catalyst with phosphine base ligands in an organic solvent at a temperature of from 50° C. to 100° C. Preferred Suzuki conditions comprise bis(tri-tert-butylphosphine) palladium (0) and potassium carbonate in 1,4-dioxane at 100° C. Alternatively, Stille coupling conditions may be employed. Preferred Stille conditions comprise a trialkylstannane and caesium fluoride in dimethylformamide at 45° C.

Deprotection according to process step (xiv) may be effected, as required, under conventional conditions. Where $Pg^2$ is benzyl, deprotection is conveniently effected by hydrogenation over palladium on carbon.

Compounds of formula (XVIII) can be prepared from compounds of formula (XIX) according to process step (xiii) by an electrophilic halogenation reaction. Preferred conditions comprise N-iodosuccinimide in acetic acid at 0° C.

Compounds of formula (XIX) can be prepared from compounds of formula (XX) according to process step (xii) by cross-coupling reaction with compounds for formula (XXI) under conditions described above in step (xii).

According to a sixth process, compounds of formula (III) may be prepared by the process illustrated in Scheme 6.

Scheme 6

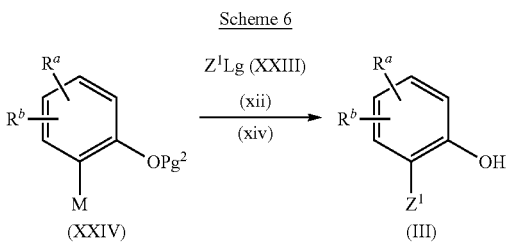

Compounds of formula (III) can be prepared from compounds of formulae (XXIII) and (XXIV) according to process step (xii) under conditions described for Scheme 5 step (xii) followed, as required, by deprotection under conventional conditions according to process step (xiv). Where $Pg^2$ is benzyl, deprotection is conveniently effected by hydrogenation over palladium on carbon.

According to a seventh process, compounds of formula (I) wherein $Z^1$ is a C-linked 5-membered heteroaryl comprising two nitrogen atoms optionally substituted by $R^8$ may be prepared by the process illustrated in Scheme 7.

Compounds of formula (I) can be prepared from compounds of formula (XXXI) according to process step (v) by a suitable deprotection under conditions described in Scheme 1 step (v).

Compounds of formula (XXXI) can be prepared from compounds of formula (XXVIII) according to process step (xvi) by cyclisation with compounds of formula (XXX) or hydrazine. Preferred conditions comprise heating to 70° C. in ethanol for 3 hours.

Compounds of formula (XXX) can be prepared from compounds of formula (XXIX) according to process step (xvii) by bimolecular nucleophilic substitution displacement of a mesylate of formula (XXIX) with hydrazine. Preferred conditions comprise heating the mesylate of formula (XXIX) in neat hydrazine at 95° C. for 18 hours.

Compounds of formula (XXVIII) can be prepared from compounds of formulae (IV) and (XXVII) according to reaction step (iv) under conditions described in Scheme 1 step (iv).

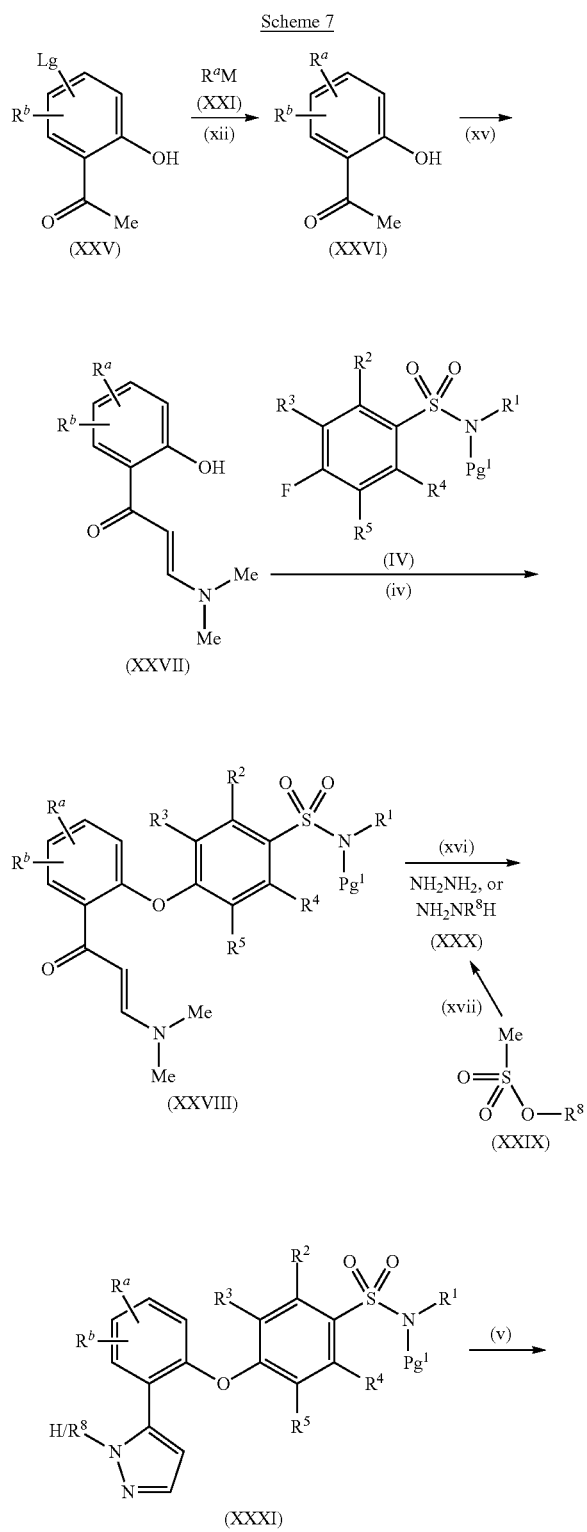

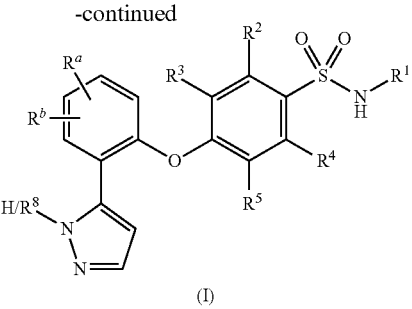

Compounds of formula (XXVII) can be prepared from compounds of formula (XXVI) according to reaction step (xv) by reaction with N,N-dimethylformamide dimethylacetal. Preferred conditions comprise N,N-dimethylformamide dimethylacetal in iso-propyl alcohol at 45° C.

Compounds of formula (XXVI) can be prepared from compounds of formulae (XXI) and (XXV) according to process step (xii) under conditions described for Scheme 5 step (xii). Preferred conditions comprise palladium tetrakis triphenyl phosphine and potassium carbonate in 1,4-dioxane and water at 60° C.

Compounds of formulae (III), (VI), (VIII), (IX), (X), (XI), (XII), (XVI), (XX), (XXI), (XXII), (XXIII), (XXIV), (XXV) and (XXIX) are either commercially available, known from the literature, easily prepared by methods well known to those skilled in the art, or can be made according to preparations described herein.

All new processes for preparing compounds of formula (I), and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmel lose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 μg to 100 mg of the compound of formula (I). The overall daily dose will typically be in the range 1 μg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., Nav1.7 channel inhibition. More particularly, the compounds of the invention are of use in the treatment of disorders for which a Nav1.7 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a Nav1.7 inhibitor is indicated.

In a further aspect of the invention there is provided use of a compound of the invention for the preparation of a medicament for the treatment of a disorder for which a Nav1.7 inhibitor is indicated.

In a further aspect of the invention there is provided a method of treating a disorder in an animal (preferably a mammal, more preferably a human) for which a Nav1.7 inhibitor is indicated, comprising administering to said animal a therapeutically effective amount of a compound of the invention.

Disorders for which a Nav1.7 inhibitor is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
  pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
  heart and vascular pain, including pain caused by angina, myocardical infarction, mitral stenosis, pericarditis, Raynaud's phenomenon, scleredoma and skeletal muscle ischemia;
  head pain, such as migraine (including migraine with aura and migraine without aura), cluster headache, tension-type headache mixed headache and headache associated with vascular disorders;
  erythermalgia; and
  orofacial pain, including dental pain, otic pain, burning mouth syndrome and temporomandibular myofascial pain.

A Nav1.7 inhibitor may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A Nav1.7 inhibitor of formula (I), or a pharmaceutically acceptable salt thereof, as defined above, may be administered in combination with one or more agents selected from:
  an alternative Nav1.7 channel modulator, such as another compound of the present invention or a compound disclosed in WO 2009/012242;
  an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
  an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;
  a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene)piperidene124-1-carboxamide);
  an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
  a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
  a barbiturate sedative, e.g. amobarbital, aprobarbital, butabarbital, butabital, mephobarbital, metharbital, methohexital, pentobarbital, phenobartital, secobarbital, talbutal, theamylal or thiopental;
  a benzodiazepine having a sedative action, e.g. chlordiazepoxide, clorazepate, diazepam, flurazepam, lorazepam, oxazepam, temazepam or triazolam;
  an $H_1$ antagonist having a sedative action, e.g. diphenhydramine, pyrilamine, promethazine, chlorpheniramine or chlorcyclizine;
  a sedative such as glutethimide, meprobamate, methaqualone or dichloralphenazone;
  a skeletal muscle relaxant, e.g. baclofen, carisoprodol, chlorzoxazone, cyclobenzaprine, methocarbamol or orphrenadine;
  an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
  an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;
  a tricyclic antidepressant, e.g. desipramine, imipramine, amitriptyline or nortriptyline;
  an anticonvulsant, e.g. carbamazepine, lamotrigine, topiratmate or valproate;
  a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
  a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-$HT_{1B/1D}$ agonist such as eletriptan, sumatriptan, naratriptan, zolmitriptan or rizatriptan;

a 5-$HT_{2A}$ receptor antagonist such as R(+)-alpha-(2,3-dimethoxy-phenyl)-1-[2-(4-fluorophenylethyl)]-4-piperidinemethanol (MDL-100907);

a 5-$HT_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, and a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl)acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a Nav1.7 inhibitor is indicated.

It is to be appreciated that all references herein to treatment include curative, palliative and prophylactic treatment.

In the non-limiting Examples and Preparations that are set out later in the description, and in the aforementioned Schemes, the following abbreviations, definitions and analytical procedures may be referred to:

AcOH is acetic acid,
$Cs_2CO_3$ is caesium carbonate;
$Cu(acac)_2$ is copper (II) acetylacetonate;
CuI is copper (I) iodide;
$Cu(OAc)_2$ is copper (II) acetate;
DAD is diode array detector;
DCM is dichloromethane; methylene chloride;
DIPEA is N-ethyldiisopropylamine, N,N-diisopropylethylamine;
DMAP is 4-dimethylaminopyridine;
DMF is N,N-dimethylformamide;
DMSO is dimethyl sulphoxide;
EDTA is ethylenediaminetetraacetic acid;
ELSD is evaporative light scattering detection;
$Et_2O$ is diethyl ether;
EtOAc is ethyl acetate;
EtOH is ethanol;
HCl is hydrochloric acid;
IPA is isopropanol;
$Ir_2(OMe)_2COD_2$ is bis(1,5-cyclooctadiene)di-µ-methoxydiiridium (I);

$K_2CO_3$ is potassium carbonate;
$KHSO_4$ is potassium hydrogen sulphate;
KOAc is potassium acetate;
KOH is potassium hydroxide;
$K_3PO_4$ is potassium phosphate tribasic;
LCMS is liquid chromatography mass spectrometry ($R_t$=retention time)
LiOH is lithium hydroxide;
MeOH is methanol;
$MgSO_4$ is magnesium sulphate;
NaH is sodium hydride;
$NaHCO_3$ is sodium hydrogencarbonate;
$Na_2CO_3$ is sodium carbonate;
$NaHSO_3$ is sodium bisulphate;
$NaHSO_4$ is sodium hydrogensulphate;
NaOH is sodium hydroxide;
$Na_2SO_4$ is sodium sulphate;
$NH_4Cl$ is ammonium chloride;
NMP is N-Methyl-2-pyrrolidone;
Pd/C is palladium on carbon;
$Pd(PPh_3)_4$ is palladium tetrakis;
$Pd(dppf)_2Cl_2$ is [1,1'-bis(diphenylphosphino)ferrocene]dichloropalladium(II), complex with dichloromethane;
THF is tetrahydrofuran;
THP is tetrahydropyran;
TLC is thin layer chromatography; and
WSCDI is 1-(3-dimethylaminopropyl)-3-ethylcarbodiimide hydrochloride.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: $CDCl_3$, deuterochloroform; $d_6$-DMSO, deuterodimethylsulphoxide; and $CD_3OD$, deuteromethanol.

Mass spectra, MS (m/z), were recorded using either electrospray ionisation (ESI) or atmospheric pressure chemical ionisation (APCI). When relevant, and unless stated otherwise, the m/z data provided are for isotopes $^{19}$F, $^{35}$Cl and $^{79}$Br.

Automated Preparative High Performance Liquid Chromatography (Auto-HPLC)

Certain compounds of the Examples and Preparations were purified using Automated Preparative High Performance Liquid Chromatography (HPLC). Reversed-phase HPLC conditions were either on Fraction Lynx systems or on a Trilution system.

In the case of the Fractionlynx system, Samples were submitted dissolved in 1 mL of DMSO. Depending on the nature of the compounds and the results of a pre-analysis, the purification was performed under either acidic ('A-HPLC'), or basic ('B-HPLC') conditions at ambient temperature. A-HPLC was carried out on a Sunfire Prep C18 OBD column (19×100 mm, 5 µm). B-HPLC was carried out on an Xterra Prep MS C18 (19×100 mm, 5 µm), both from Waters. A flow rate of 18 mL/min was used with mobile phase A: water+ 0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:
ES+ Cone voltage: 30 v Capillary: 3.20 kv
ES− Cone voltage: −30 v Capillary: −3.00 kv
Desolvation gas: 600 L/hr
Source Temp: 120° C.
Scan range 150-900 Da The fraction collection was triggered by both MS and ELSD.

Quality control (QC) analysis was performed using a LCMS method. Acidic runs were carried out on a Sunfire C18 (4.6×50 mm, 5 μm), basic runs were carried out on a Xterra C18 (4.6×50 mm, 5 μm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:
ES+ Cone voltage: 25 v Capillary: 3.30 kv
ES− Cone voltage: −30 v Capillary: −2.50 kv
Desolvation gas: 800 L/hr
Source Temp: 150° C.
Scan range 160-900 Da Where the reversed-phase Trilution system was used (T-HPLC) the conditions were as follows:
Mobile phase A: 0.1% formic acid in water
Mobile phase B: 0.1% formic acid in acetonitrile
Column: Phenomenex C18 Luna 21.5 mm×15 cm with 5 micron particule size
Gradient: 95-5% A over 15 min, 15 min hold, 15 ml/min flow rate
UV: 200 nm-400 nm
Temperature: Room temperature
Liquid Chromatography Mass Spectrometry Unless carried out by Auto-HPLC (under conditions of A-HPLC or B-HPLC) as just decriberd, LCMS conditions were run according to one of the conditions given below (where ratios of solvents are given, the ratios are by volume):
Acidic 2 Minute LCMS
Mobile phase A: 0.1% formic acid in water
Mobile phase B: 0.1% formic acid in 70% methanol: 30% isopropanol
Column: C18 phase Phenomenex 20×4.0 mm with 3 micron particle size
Gradient: 98-10% A over 1.5 min, 0.3 min hold, 0.2 re-equilbration, 2 ml/min flow rate
UV: 210 nm-450 nm DAD
Temperature: 75° C.
Or
Mobile phase A: 0.1% formic acid in water
Mobile phase B: 0.1% formic acid in acetonitrile
Column: C18 phase Phenomenex 20×4.0 mm with 3 micron particle size
Gradient: 70-2% A over 1.5 min, 0.3 min hold, 0.2 re-equilbration, 1.8 ml/min flow rate
UV: 210 nm-450 nm DAD
Temperature: 75° C.

Acidic 4.5 Minute LCMS
Mobile phase A: 0.05% formic acid in water
Mobile phase B: acetonitrile
Column: Phenomenex Gemini C18 45×45 mm with 5 micron particle size
Gradient: 80-50% A over 0.5 min, 50-2% A over 3 min, 1 min hold, 0.2 min re-equilibration, 2.0 ml/min flow rate
UV: 220 nm-254 nm DAD
Temperature: 40° C.

Acidic 8 Minute LCMS
Mobile phase A: 0.05% formic acid in water
Mobile phase B: acetonitrile
Column: Phenomenex Gemini C18 45×45 mm with 5 micron particle size
Gradient: 80-50% A over 0.5 min, 50-2% A over 3 min, 4.5 min hold, 0.2 min re-equilibration, 2.0 ml/min flow rate
UV: 220 nm-254 nm DAD
Temperature: 40° C.

Acidic 6 Minute LCMS
Mobile phase A: 0.1% formic acid in water
Mobile phase B: 0.1% formic acid in acetonitrile
Column: C18 phase Waters Sunfire 50×4.6 mm with 5 micron particle size
Gradient: 95-5% A over 3 min, 1 min hold, 2 min re-equilibration, 1.5 ml/min flow rate
UV: 210 nm-450 nm DAD
Temperature: 50° C.

Basic 6 Minute LCMS
Mobile phase A: 0.1% ammonium hydroxide in water
Mobile phase B: 0.1% ammonium hydroxide in acetonitrile
Column: C18 phase Fortis 50×4.6 mm with 5 micron particle size
Gradient: 95-5% A over 3 min, 1 min hold, 2 min re-equilibration, 1 ml/min flow rate
UV: 210 nm-450 nm DAD
Temperature: 50° C.

Acidic 30 Minute LCMS
Mobile phase A: 0.1% formic acid in water
Mobile phase B: 0.1% formic acid in acetonitrile
Column: Phenomenex C18 phase Gemini 150×4.6 mm with 5 micron particle size
Gradient: 98-2% A over 18 min, 2 min hold, 1 ml/min flow rate
UV: 210 nm-450 nm DAD
Temperature: 50° C.

Basic 30 Minute LCMS
Mobile phase A: 10 mM ammonium acetate in water
Mobile phase B: 10 mM ammonium acetate in methanol
Column: Phenomenex Phenyl Hexyl 150×4.6 mm with 5 micron particle size
Gradient: 98-2% A over 18 min, 2 min hold, 1 ml/min flow rate
UV: 210 nm-450 nm DAD
Temperature: 50° C.

EXAMPLE 1

3-Cyano-4-{[3-pyridazin-4-yl-3'-(trifluoromethyl)biphenyl-4-yl]oxy}-N-1,2,4-thiadiazol-5-ylbenzenesulfonamide

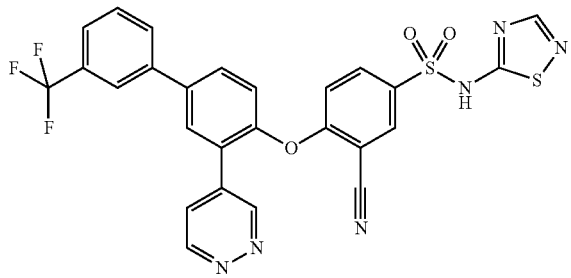 [SMILES: N#Cc1cc(S(=O)(=O)Nc2ncns2)ccc1Oc1ccc(-c2cccc(C(F)(F)F)c2)cc1-c1ccnnc1]

3-Cyano-N-(2,4-dimethoxybenzyl)-4-{[3-pyridazin-4-yl-3'-(trifluoromethyl)biphenyl-4-yl]oxy}-N-1,2,4-thiadiazol-5-ylbenzenesulfonamide (Preparation 20, 386 mg, 0.52 mmol) was dissolved in a 4M solution of hydrogen chloride in 1,4-dioxane (13 mL) and stirred at room temperature for 18 hours. The reaction was concentrated in vacuo and purified using silica gel column chromatography (1% acetic acid in dichloromethane to 10% methanol and 1% acetic acid in dichloromethane gradient elution) followed by a second purification using silica gel column chromatography (0%-15% methanol in dichloromethane gradient elution) to afford the title compound (76 mg, 25%).

$^1$HNMR (CD$_3$OD): δ 7.05 (m, 1H), 7.39 (m, 1H), 7.67 (m, 2H), 7.91-8.05 (m, 7H), 8.20 (m, 1H), 9.20 (m, 1H), 9.50 (m, 1H)

LCMS Rt=5.14 minutes MS m/z 581 [MH]+

EXAMPLE 2

5-Chloro-2-fluoro-4-{[3-pyridazin-4-yl-4'-(trifluoromethyl)biphenyl-4-yl]oxy}-N-pyrimidin-2-ylbenzenesulfonamide

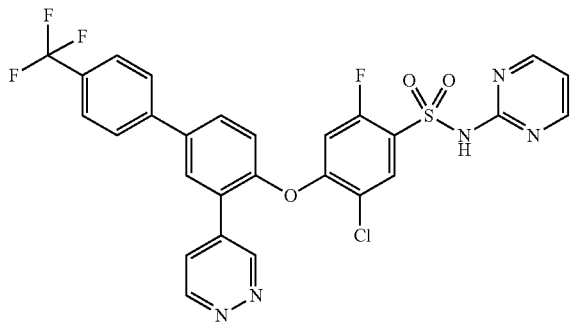 [SMILES: O=S(=O)(Nc1ncccn1)c1cc(Cl)c(Oc2ccc(-c3ccc(C(F)(F)F)cc3)cc2-c2ccnnc2)cc1F]

5-Chloro-N-(2,4-dimethoxybenzyl)-2-fluoro-4-{[3-pyridazin-4-yl-4'-(trifluoromethyl)biphenyl-4-yl]oxy}-N-pyrimidin-2-ylbenzenesulfonamide (Preparation 48) 356 mg, 0.47 mmol) was dissolved in 1,4-dioxane (1.5 mL) and a 4M solution of hydrogen chloride in 1,4-dioxane (2.4 mL) added. The mixture was stirred at room temperature for 18 hours. The reaction mixture was concentrated in vacuo and the resulting residue purified by reverse phase preparative HPLC (Trilution method) to afford the title compound as a white solid (120 mg, 42%).

$^1$HNMR (CD$_3$OD): δ 6.85 (m, 1H), 6.95 (m, 1H), 7.30 (m, 1H), 7.80 (m, 2H), 7.90 (m, 3H), 8.00 (m, 2H), 8.10 (m, 1H), 8.40 (m, 2H), 9.20 (m, 1H), 9.50 (m, 1H)

LCMS Rt=3.12 minutes MS m/z 602 [MH]+

EXAMPLE 3

3-Chloro-N-pyridazin-3-yl-4-{[3-pyridazin-4-yl-4'-(trifluoromethyl)biphenyl-4-yl]oxy}benzenesulfonamide

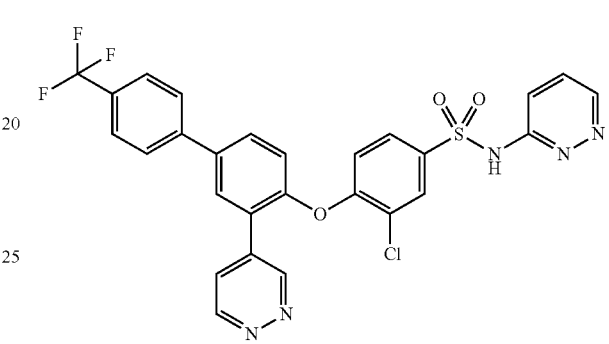

A mixture of 3-Chloro-N-(methoxymethyl)-N-pyridazin-3-yl-4-{[3-pyridazin-4-yl-4'-(trifluoromethyl)biphenyl-4-yl]oxy}benzenesulfonamide and 3-chloro-N-[(3E)-2-(methoxymethyl)pyridazin-3(2H)-ylidene]-4-{[3-pyridazin-4-yl-4'-(trifluoromethyl)biphenyl-4-yl]oxy}benzenesulfonamide (Preparation 49, 85 mg, 0.13 mmol) were dissolved in dichloromethane (1 mL) and a 4M solution of hydrogen chloride in 1,4-dioxane (0.34 mL) added. The mixture was stirred at room temperature for 15 minutes. The reaction mixture was concentrated in vacuo and the resulting residue purified by reverse phase preparative HPLC (Trilution method) to afford the title compound as a white solid (26 mg, 33%).

$^1$HNMR (CD$_3$OD): δ 7.10 (m, 1H), 7.20 (m, 1H), 7.60 (m, 1H), 7.80 (m, 3H), 7.90 (m, 4H), 8.05 (m, 3H), 8.30 (m, 1H), 9.20 (m, 1H), 9.55 (m, 1H).

LCMS Rt=3.20 minutes MS m/z 584 [MH]+, 582 [MH]−

EXAMPLE 4

5-Chloro-2-fluoro-4-{[3-pyridazin-4-yl-2'-(trifluoromethyl)biphenyl-4-yl]oxy}-N-1,3,4-thiadiazol-2-ylbenzenesulfonamide

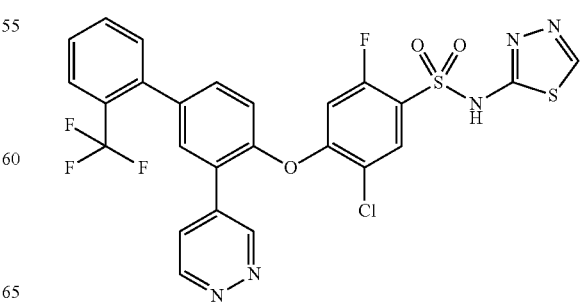

5-Chloro-N-(2,4-dimethoxybenzyl)-2-fluoro-4-{[3-pyridazin-4-yl-2'-(trifluoromethyl)biphenyl-4-yl]oxy}-N-1,3,4-thiadiazol-2-ylbenzenesulfonamide (Preparation 23, 339 mg, 0.45 mmol) was dissolved in a 4M solution of hydrogen chloride in 1,4-dioxane (10 mL). The mixture was stirred at room temperature for 2 hours. The reaction mixture was concentrated in vacuo and the resulting residue purified by reverse phase preparative HPLC (Trilution method) to afford the title compound as a white solid (75 mg, 27%).

$^1$HNMR (CD$_3$OD): δ 6.91 (d, 1H), 7.22 (d, 1H), 7.48-7.57 (m, 2H), 7.58 (t, 1H), 7.62 (t, 1H), 7.71 (t, 1H), 7.82 (d, 1H), 7.92-7.97 (m, 1H), 8.00 (d, 1H), 8.58 (s, 1H), 9.20 (d, 1H), 9.43 (s, 1H)

LCMS Rt=3.26 minutes MS m/z 608.1 [MH]+, 606.1 [MH]−

EXAMPLE 5

5-Chloro-2-fluoro-4-O-pyridazin-4-yl-3'-(trifluoromethyl)biphenyl-4-yl]oxy}-N-1,3,4-thiadiazol-2-yl-benzenesulfonamide

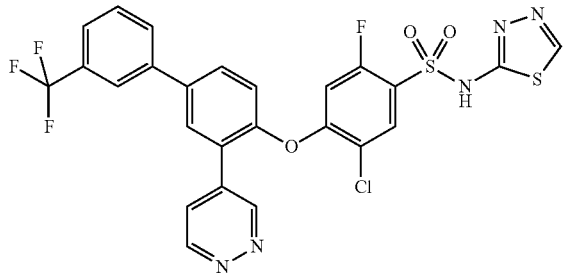 [SMILES: O=S(=O)(Nc1nncs1)c1cc(Cl)c(Oc2ccc(-c3cccc(C(F)(F)F)c3)cc2-c2ccnnc2)cc1F]

5-Chloro-N-(2,4-dimethoxybenzyl)-2-fluoro-4-{[3-pyridazin-4-yl-3'-(trifluoromethyl)biphenyl-4-yl]oxy}-N-1,3,4-thiadiazol-2-ylbenzenesulfonamide (Preparation 22, 266 mg, 0.35 mmol) was dissolved a in 4M solution of hydrogen chloride in 1,4-dioxane (10 mL) and stirred at room temperature for 3 hours. A precipitate formed which was collected by filtration and triturated with acetonitrile to afford a solid. The filtrate and solid were combined and concentrated in vacuo. The resulting residue was purified by silica gel column chromatography (0%-20% methanol in dichloromethane gradient elution) to afford the title compound as a solid (67 mg, 31%).

$^1$HNMR (CD$_3$OD): δ 6.95 (m, 1H), 7.40 (m, 1H), 7.70 (m, 2H), 7.90 (m, 1H), 7.95-8.05 (m, 5H), 8.60 (s, 1H), 9.25 (m, 1H), 9.55 (m, 1H)

LCMS Rt=3.43 minutes MS m/z 608 [MH]+, 606 [MH]−

EXAMPLE 6

5-Chloro-2-fluoro-4-{[3-pyridazin-4-yl-4'-(trifluoromethyl)biphenyl-4-yl]oxy}-N-1,3,4-thiadiazol-2-ylbenzenesulfonamide

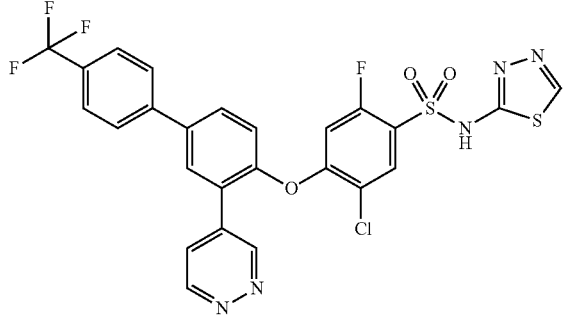 [SMILES: O=S(=O)(Nc1nncs1)c1cc(Cl)c(Oc2ccc(-c3ccc(C(F)(F)F)cc3)cc2-c2ccnnc2)cc1F]

5-Chloro-N-(2,4-dimethoxybenzyl)-2-fluoro-4-{[3-pyridazin-4-yl-4'-(trifluoromethyl)biphenyl-4-yl]oxy}-N-1,3,4-thiadiazol-2-ylbenzenesulfonamide (Preparation 24, 213 mg, 0.28 mmol) was dissolved a in 4M solution of hydrogen chloride in 1,4-dioxane (7 mL) and stirred at room temperature for 3 hours. A precipitate formed which was collected by filtration and purified by reverse phase preparative HPLC (Trilution method) to afford the title compound as a solid (44 mg, 26%).

$^1$HNMR (CD$_3$OD): δ 6.95 (m, 1H), 7.30 (m, 1H), 7.50-7.70 (m, 2H), 7.80 (m, 1H), 7.90-8.05 (m, 5H), 8.60 (s, 1H), 9.25 (m, 1H), 9.55 (m, 1H)

LCMS Rt=3.44 minutes MS m/z 608 [MH]+, 606 [MH]−

EXAMPLE 7

3-Cyano-4-{[3-pyridazin-4-yl-4'-(trifluoromethyl)biphenyl-4-yl]oxy}-N-1,2,4-thiadiazol-5-ylbenzenesulfonamide

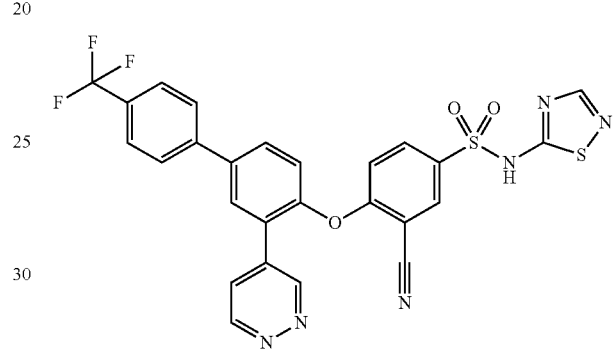

3-Cyano-N-(2,4-dimethoxybenzyl)-4-{[3-pyridazin-4-yl-4'-(trifluoromethyl)biphenyl-4-yl]oxy}-N-1,2,4-thiadiazol-5-ylbenzenesulfonamide (Preparation 26, 210 mg, 0.29 mmol) was dissolved a in 4M solution of hydrogen chloride in 1,4-dioxane (7 mL) and stirred at room temperature for 5 hours. A precipitate formed which was collected by filtration and purified by trituration with dichloromethane followed by silica gel column chromatography (0%-15% methanol in dichloromethane gradient elution) to afford the title compound as a solid (77 mg, yield).

$^1$HNMR (d$_6$-DMSO): δ 7.11 (d, 1H), 7.47 (d, 1H), 7.82 (d, 2H), 7.84-7.88 (m, 3H), 8.00-8.10 (m, 3H), 8.18 (d, 2H), 8.24 (s, 1H), 9.23 (d, 1H), 9.50 (s, 1H).

LCMS Rt=4.89 minutes MS m/z 581 [MH]+

EXAMPLE 8

3-Fluoro-4-{[3-(1-methyl-1H-pyrazol-5-yl)biphenyl-4-yl]oxy}-N-1,3-thiazol-2-ylbenzenesulfonamide

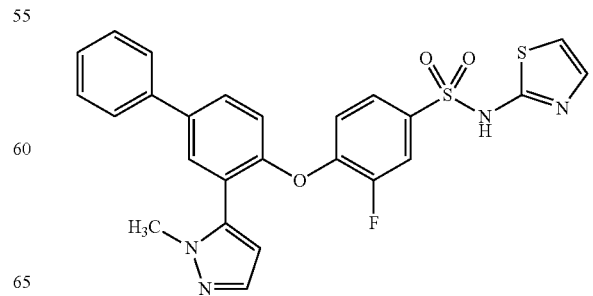

A solution of 3-fluoro-4-{[3-(1-methyl-1H-pyrazol-5-yl) biphenyl-4-yl]oxy}benzenesulfonyl chloride (Preparation 31, 350 mg, 0.79 mmol) and 2-amino thiazole (158 mg, 1.58 mmol) in pyridine (2 mL) was stirred at room temperature for 12 hours. The reaction mixture was concentrated in vacuo and the residue acidified to pH 4-5 with a 1M aqueous solution of hydrogen chloride. The mixture was extraction with ethyl acetate (3×10 mL). The organic layer was separated and washed sequentially with water (3×5 mL) and brine (1×5 mL), then dried over anhydrous sodium sulfate and concentrated in vacuo. The residue was purified by silica gel column chromatography (100-200 mesh silica gel, 35% ethyl acetate in hexane) followed by trituration with pentane to afford the title compound as an off white solid (75 mg, 19%).

$^1$HNMR (d$_6$-DMSO): δ 3.76 (s, 3H), 6.31 (s, 1H), 6.87 (d, 1H), 7.14 (t, 1H), 7.25 (d, 1H), 7.28 (d, 1H), 7.38-7.40 (m, 2H), 7.48 (t, 2H), 7.56 (d, 1H), 7.65 (d, 1H), 7.72-7.76 (m, 3H), 12.82 (s, 1H).

EXAMPLE 9

3-Chloro-4-[(3-pyridazin-4-ylbiphenyl-4-yl)oxy]-N-1,3,4-thiadiazol-2-ylbenzenesulfonamide

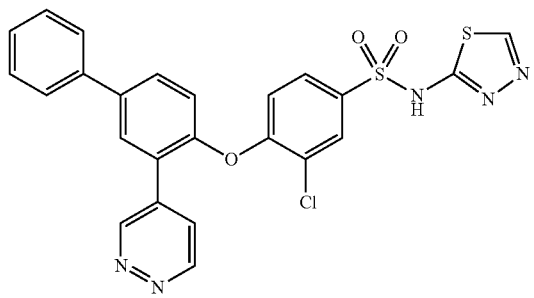 [SMILES: O=S(=O)(Nc1nncs1)c1ccc(Oc2ccc(-c3ccccc3)cc2-c2ccnnc2)c(Cl)c1]

3-Pyridazin-4-ylbiphenyl-4-ol (Preparation 4, 40 mg, 0.16 mmol) and 3-chloro-N-(2,4-dimethoxybenzyl)-4-fluoro-N-1,3,4-thiadiazol-2-ylbenzenesulfonamide (Preparation 17, 72 mg, 0.16 mmol) were dissolved in dimethylsulfoxide (2 mL). Potassium carbonate (67 mg, 0.5 mmol) was added and the reaction stirred at room temperature for 16 hours. The crude material was partitioned between ethyl acetate (20 mL) and water (20 mL), the organic layer separated, concentrated in vacuo, dissolved in trifluoroacetic acid (1 mL) and the solution stirred for 16 hours at room temperature. The reaction was then concentrated in vacuo and purified by silica gel column chromatography (ISCO™, 12 g silica, 50-100% ethyl acetate in heptane gradient elution). The appropriate fractions were combined and concentrated in vacuo to afford the title compound as a white solid (41 mg, 49%).

$^1$HNMR (CD$_3$OD): δ 7.18 (d, 1H), 7.21 (m, 2H), 7.39 (m, 1H), 7.45 (m, 2H) 7.69 (d, 1H) 7.78 (d, 1H), 7.84 (m, 2H) 7.95(m, 1H) 7.99 (m, 1H), 8.78(s, 1H) 9.24 (m, 1H) 9.51 (m, 1H).

LCMS Rt=1.66 minutes MS m/z 522 [MH]+

EXAMPLE 10

3-Cyano-4-[(3-Pyridazin-4-ylbiphenyl-4-yl)oxy]-N-1,3,4-thiadiazol-2-ylbenzenesulfonamide

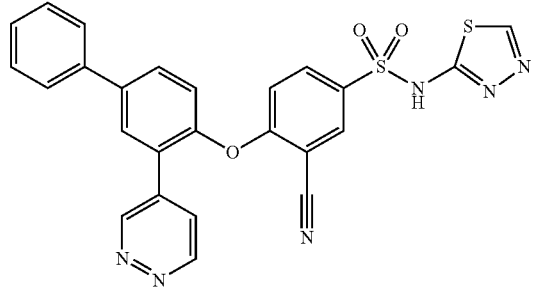 [SMILES: N#Cc1cc(S(=O)(=O)Nc2nncs2)ccc1Oc1ccc(-c2ccccc2)cc1-c1ccnnc1]

3-Pyridazin-4-ylbiphenyl-4-ol (Preparation 4, 50 mg, 0.2 mmol) and 3-cyano-N-(2,4-dimethoxybenzyl)-4-fluoro-N-1,3,4-thiadiazol-2-ylbenzenesulfonamide (Preparation 15, 87.3 mg, 0.2 mmol) were dissolved in dimethylsulfoxide (2 mL). Potassium carbonate (83 mg, 0.6 mmol) was added and the reaction stirred at room temperature for 16 hours. The crude material was partitioned between ethyl acetate (20 mL) and water (20 mL), the organic layer separated, concentrated in vacuo, dissolved in trifluoroacetic acid (1 mL) and the solution stirred for 16 hours at room temperature. The reaction was concentrated in vacuo then purified by reverse phase column chromatography (ISCO™, 12 g, C18, 20:1 water:acetonitrile to 1:4 water:acetonitrile). The appropriate fractions were combined and concentrated in vacuo to afford the title compound as a white solid (25 mg, 24%).

$^1$HNMR (CD$_3$OD): δ 7.04 (d, 1H), 7.41 (m, 2H), 7.49 (m, 2H) 7.73 (m, 2H) 7.90 (m, 1H) 7.97 (m, 3H), 8.17 (d, 1H) 8.54 (s, 1H), 9.19 (m, 1H) 9.45 (m, 1H)

LCMS Rt=1.61 minutes MS m/z 513 [MH]+

EXAMPLE 11

5-Chloro-2-fluoro-4-[(3-pyridazin-4-ylbiphenyl-4-yl)oxy]-N-1,3,4-thiadiazol-2-ylbenzenesulfonamide

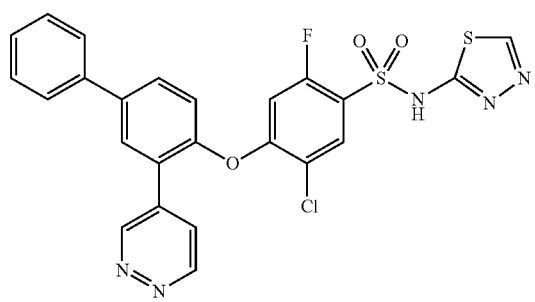 [SMILES: O=S(=O)(Nc1nncs1)c1cc(Cl)c(Oc2ccc(-c3ccccc3)cc2-c2ccnnc2)cc1F]

5-Chloro-N-(2,4-dimethoxybenzyl)-2-fluoro-4-[(3-pyridazin-4-ylbiphenyl-4-yl)oxy]-N-1,3,4-thiadiazol-2-ylbenzenesulfonamide (Preparation 25, 124 mg, 0.18 mmol) was dissolved in trifluoroacetic acid (1 mL) and the solution stirred for 16 hours at room temperature. The reaction was concentrated in vacuo then purified by reverse phase column chromatography (ISCO™, 12 g, C18, 20:1 water:acetonitrile to 1:4 water:acetonitrile). The appropriate fractions were combined and concentrated in vacuo to afford the title compound as a white solid (61 mg, 63%).

$^1$HNMR (CD$_3$OD): δ 7.20 (d, 1H) 7.28 (d, 1H), 7.39 (m, 1H), 7.48 (m, 2H) 7.78 (m, 2H) 7.84 (m, 1H) 7.90 (d, 1H), 7.94 (m, 1H) 7.98 (d, 1H) 8.78 (s, 1H), 9.27 (m, 1H) 9.50 (m, 1H).

LCMS Rt=1.71 minutes MS m/z 540 [MH]+

EXAMPLE 12

3-Cyano-4-[(3-pyridazin-4-ylbiphenyl-4-yl)oxy]-N-1,2,4-thiadiazol-5-ylbenzenesulfonamide

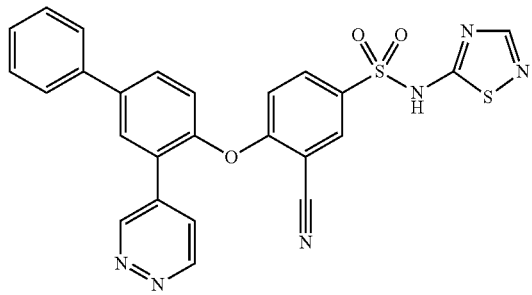 [SMILES: N#Cc1cc(S(=O)(=O)Nc2ncns2)ccc1Oc1ccc(-c2ccccc2)cc1-c1ccnnc1]

3-Pyridazin-4-ylbiphenyl-4-ol (Preparation 4, 50 mg, 0.2 mmol) and 3-cyano-4-fluoro-N-(1,2,4-thiadiazol-5-yl)benzenesulfonamide (Preparation 47, 50 mg, 0.2 mmol) were dissolved in dimethylsulfoxide (2 mL). Potassium carbonate (83 mg, 0.6 mmol) was added and the reaction heated to 90° C. for 16 hours. The crude material was then purified by reverse phase column chromatography (ISCO™, 4 g, C18, 20:1 water:acetonitrile to 3:2 water acetonitrile). The appropriate fractions were combined and concentrated in vacuo to afford the title compound as an off white solid (25 mg, 24%).

$^1$HNMR (CD$_3$OD): δ 6.98 (d, 1H) 7.33 (d, 1H), 7.37 (m, 1H), 7.46 (m, 2H) 7.70 (m, 2H) 7.84 (m, 1H) 7.93 (m, 3H), 8.00 (m, 1H) 8.16 (d, 1H), 9.17 (m, 1H) 9.45 (m, 1H)

LCMS Rt=1.23 minutes MS m/z 550 [MK]+

EXAMPLE 13

5-Chloro-2-fluoro-4-({3-[1-(1-methylazetidin-3-yl)-1H-pyrazol-5-yl]-2'-(trifluoromethyl)biphenyl-4-yl}oxy)-N-1,3,4-thiadiazol-2-ylbenzenesulfonamide

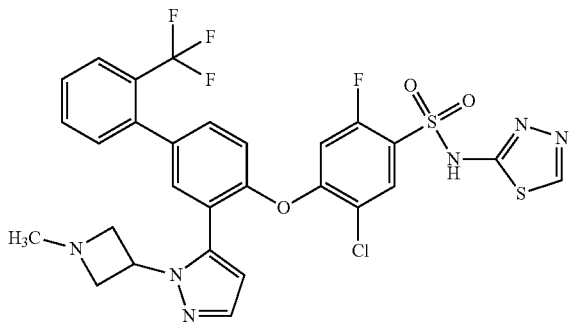 [SMILES: CN1CC(n2nccc2-c2cc(-c3ccccc3C(F)(F)F)ccc2Oc2cc(F)c(S(=O)(=O)Nc3nncs3)cc2Cl)C1]

To a suspension of 4-{[3-(1-azetidin-3-yl-1H-pyrazol-5-yl)-2'-(trifluoromethyl)biphenyl-4-yl]oxy}-5-chloro-2-fluoro-N-1,3,4-thiadiazol-2-ylbenzenesulfonamide (Preparation 46, 42.9 mg, 0.0659 mmol) in methanol (0.10 mL), dichloromethane (1.72 mL) and acetic acid (0.10 mL) was added formaldehyde (37% w/w, 16.7 µL, 0.224 mmol). The reaction was then stirred under nitrogen at room temperature for 45 minutes. Sodium triacetoxyborohydride (42.6 mg, 0.201 mmol) was added to the reaction which was stirred for 18 hours at room temperature. The reaction was diluted with dichloromethane (20 mL) and washed with water (3×2 mL). The combined aqueous phases were extracted with dichloromethane (3×5 mL). The combined organic phases were dried over anhydrous sodium sulfate, filtered and concentrated in vacuo to afford a white solid (58.0 mg). The solid was purified by B-HPLC to afford the title compound.

LCMS Rt=2.54 minutes (basic QC method) MS m/z 665 [MH]+, 663 [MH]−

EXAMPLE 14

5-Chloro-2-fluoro-4-({3-[1-(1-methylazetidin-3-yl)-1H-pyrazol-5-yl]-4'-(trifluoromethyl)biphenyl-4-yl}oxy)-N-1,3,4-thiadiazol-2-ylbenzenesulfonamide

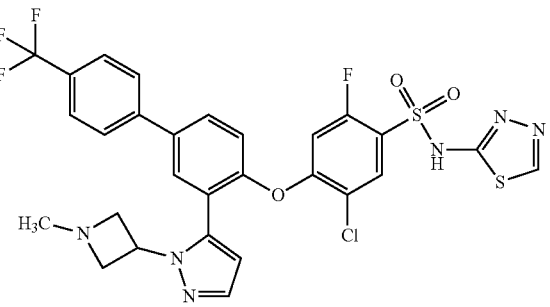

To a suspension of 4-{[3-(1-azetidin-3-yl-1H-pyrazol-5-yl)-4'-(trifluoromethyl)biphenyl-4-yl]oxy}-5-chloro-2-fluoro-N-1,3,4-thiadiazol-2-ylbenzenesulfonamide (Preparation 41, 46.3 mg, 0.0711 mmol) in methanol (0.11 mL), dichloromethane (1.86 mL) and acetic acid (0.11 mL) was added formaldehyde (37% w/w, 19.6 µL, 0.263 mmol). The reaction was then stirred under nitrogen at room temperature for 45 minutes. Sodium triacetoxyborohydride (45.9 mg, 0.217 mmol) was added to the reaction which was stirred for 18 hours at room temperature. The reaction was diluted with dichloromethane (20 mL) and washed with water (3×2 mL). The combined aqueous phases were extracted with dichloromethane (3×5 mL). The combined organic layers were dried over anhydrous sodium sulfate, filtered and concentrated in vacuo to afford a clear gum (58.0 mg). The clear gum was purified by B-HPLC to afford the title compound.

LCMS Rt=2.77 minutes (acidic QC method) MS m/z 665 [MH]+, 663 [MH]−

EXAMPLE 15

3-Cyano-N-(5-fluoro-1,3-thiazol-2-yl)-4-{[3-(1-methyl-1H-pyrazol-5-yl)biphenyl-4-yl]oxy}benzenesulfonamide

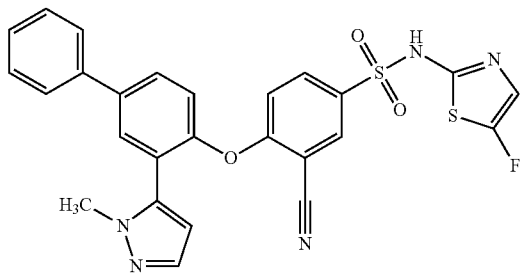 [SMILES: Cn1nccc1-c1cc(-c2ccccc2)ccc1Oc1ccc(S(=O)(=O)Nc2ncc(F)s2)cc1C#N]

To a stirred solution of 3-(1-methyl-1H-pyrazol-5-yl)biphenyl-4-ol (Preparation 28, 188 mg, 0.75 mmol) and potassium carbonate (173 mg, 1.25 mmol) in N,N-dimethylformamide (2.5 mL) was added 3-cyano-4-fluoro-N-(5-fluoro-1,3-thiazol-2-yl)benzenesulfonamide (Preparation 34, 151 mg, 0.5 mmol) and the reaction mixture was stirred at 80° C. After stirring for 16 hours, the reaction mixture was cooled to room temperature. Saturated aqueous ammonium chloride (10 mL) was added to the reaction mixture and the mixture was extracted with dichloromethane (3×10 mL). The collected organic layer was dried over anhydrous magnesium sulfate, filtered and concentrated in vacuo to obtain a crude residue. The residue was purified by silica gel column chromatography (40% ethyl acetate in dichloromethane elution) to afford the title compound as a white solid (127 mg, 48%).

$^1$HNMR (d$_6$-DMSO): δ 3.78 (s, 3H), 6.26 (d, 1H), 6.96 (d, 1H), 7.35-7.44 (m, 3H), 7.47-7.55 (m, 3H), 7.76-7.81 (m, 2H), 7.84 (d, 1H), 7.90-7.95 (m, 2H), 8.14 (d, 1H)

LCMS Rt=3.24 minutes MS m/z 532 [MH]+

EXAMPLE 16

3-Cyano-4-{[3-(1-methyl-1H-pyrazol-5-yl)biphenyl-4-yl]oxy}-N-1,2,4-thiadiazol-5-ylbenzenesulfonamide

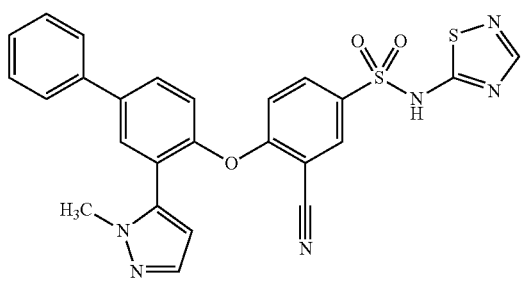 [SMILES: Cn1nccc1-c1cc(-c2ccccc2)ccc1Oc1ccc(S(=O)(=O)Nc2ncns2)cc1C#N]

To a stirred solution of 3-(1-methyl-1H-pyrazol-5-yl)biphenyl-4-ol (Preparation 28, 44.1 mg, 0.176 mmol) and potassium carbonate (30.4 mg, 0.22 mmol) in N,N-dimethylformamide (1 mL) was added 3-cyano-4-fluoro-N-(1,2,4-thiadiazol-5-yl)benzenesulfonamide (Preparation 47, 50.0 mg, 0.176 mmol) and the reaction mixture was stirred at 100° C. After stirring for 24 hours, the reaction mixture was cooled to room temperature. A 1M aqueous solution of hydrogen chloride (10 mL) was added to the reaction mixture and the mixture was extracted with dichloromethane (3×10 mL). The combined organic layer was concentrated in vacuo to obtain the title compound (90 mg, 99%).

LCMS Rt=3.22 minutes MS m/z 515 [MH]+

EXAMPLE 17

3-Cyano-4-{[3-pyridazin-4-yl-2'-(trifluoromethyl)biphenyl-4-yl]oxy}-N-1,2,4-thiadiazol-5-ylbenzenesulfonamide

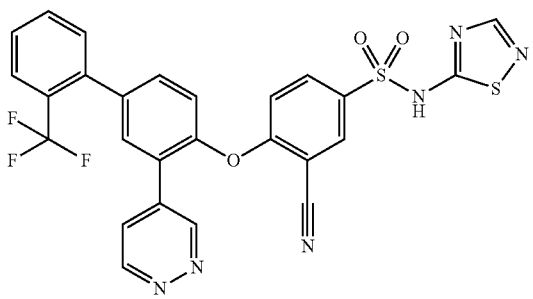 [SMILES: N#Cc1cc(S(=O)(=O)Nc2ncns2)ccc1Oc1ccc(-c2ccccc2C(F)(F)F)cc1-c1ccnnc1]

3-Cyano-N-(2,4-dimethoxybenzyl)-4-{[3-pyridazin-4-yl-2'-(trifluoromethyl)biphenyl-4-yl]oxy}-N-1,2,4-thiadiazol-5-ylbenzenesulfonamide (Preparation 21, 400 mg, 0.55 mmol) was dissolved in a 4M solution of HCl in 1,4-dioxane (9 mL). The mixture was stirred at room temperature for 2 hours and then concentrated in vacuo. The residue was purified by silica gel column chromatography (0%-15% methanol in dichloromethane gradient elution), followed by trituration in tert-butylmethyl ether. The residue was purified further by a silica plug column (0%-20% methanol in dichloromethane) to afford the title compound (73 mg, 23%) as a white solid.

$^1$HNMR (400 MHz, CD$_3$OD): δ 7.01 (d, 1H), 7.34 (d, 1H), 7.49 (d, 1H), 7.52-7.60 (m, 2H), 7.62-7.70 (m, 2H), 7.79 (d, 1H), 7.83-7.95 (m, 2H), 8.01 (d, 1H), 8.17 (s, 1H), 9.18 (d, 1H), 9.42 (s, 1H)

EXAMPLE 18

3-Cyano-4-{[3'-methoxy-3-(1-methyl-1H-pyrazol-5-yl)biphenyl-4-yl]oxy}-N-(1,3-thiazol-2-yl)benzenesulfonamide

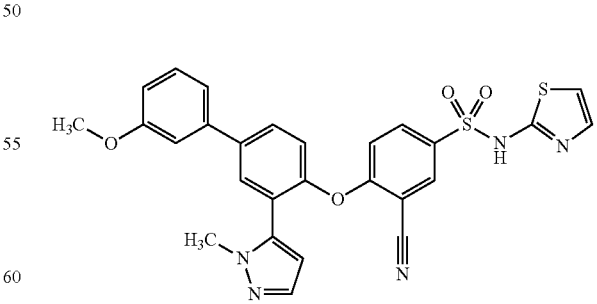

To a solution of 4-[4-bromo-2-(2-methyl-2H-pyrazol-3-yl)-phenoxy]-3-cyano-N-(2,4-dimethoxy-benzyl)-N-thiazol-2-yl-benzenesulfonamide (Preparation 88, 98.5 mg, 0.148 mmol), 3-methoxyphenylboronic acid (48 mg, 0.32 mmol), and potassium carbonate (62.5 mg, 0.452 mmol) in toluene (3 mL) was added tetrakistriphenylphosphine-palladium (0) (22.5 mg, 0.0195 mmol) and the mixture was sparged two times with argon. The reaction mixture was heated at reflux for 4.5 hours. After cooling to room temperature the reaction mixture was partitioned between ethyl acetate and water. The organic layer was separated and washed with saturated sodium chloride solution, dried over anhydrous MgSO$_4$, filtered, and concentrated in vacuo. The residue was purified by automated flash column chromatography using a 0-100% EtOAc/hexanes gradient to yield a clear oil. This oil was dissolved in methylene chloride (5 mL) and treated with trifluoroacetic acid (1 mL, 10 mmol). After stirring for 1 hour, the reaction mixture was concentrated in vacuo and purified by automated flash column chromatography (0%-5% methanol in dichloromethane gradient elution) to yield the title compound (49 mg, 61%) as a white solid.

$^1$HNMR (400 MHz, d6-DMSO): δ 3.70 (s, 3H), 3.86 (s, 3H), 6.28 (m, 1H), 6.90 (m, 2H), 6.96 (m, 1H), 7.36 (m, 2H), 7.38 (m, 2H), 7.43 (m, 1H), 7.54 (m, 1H), 7.89 (m, 1H), 7.94 (m, 2H), 8.14 (m, 1H), 12.80 (s, 1H).

LCMS Rt=1.70 minutes; MS m/z 544 [MH]$^+$

EXAMPLE 19

3-Cyano-4-{[2'-methoxy-3-(1-methyl-1H-pyrazol-5-yl)biphenyl-4-yl]oxy}-N-(1,3-thiazol-2-yl)benzenesulfonamide

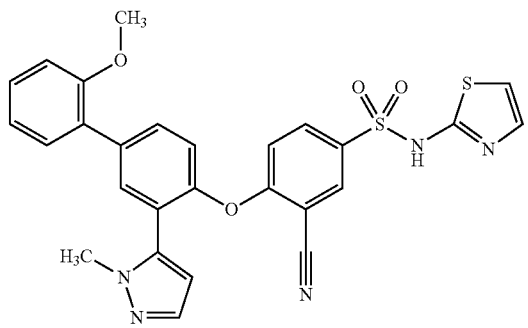 [SMILES: COc1ccccc1-c1ccc(Oc2ccc(S(=O)(=O)Nc3nccs3)cc2C#N)c(-c2ccnn2C)c1]

To a solution of 4-[4-bromo-2-(2-methyl-2H-pyrazol-3-yl)-phenoxy]-3-cyano-N-(2,4-dimethoxy-benzyl)-N-thiazol-2-yl-benzenesulfonamide (Preparation 88, 98.5 mg, 0.148 mmol), 2-methoxyphenylboronic acid (48 mg, 0.32 mmol), and potassium carbonate (62.5 mg, 0.452 mmol) in toluene (3 mL) was added tetrakis(triphenylphosphine)palladium(0) (22.5 mg, 0.0195 mmol) and the mixture was sparged two times with argon. The reaction mixture was then heated at reflux for 4.5 hours and then allowed to cool to room temperature. The reaction mixture was diluted with ethyl acetate and washed with water and saturated sodium chloride solution. The organic layer was dried over anhydrous MgSO$_4$, filtered, and concentrated in vacuo. The residue was purified by automated flash column chromatography using a 0-100% EtOAc/hexanes gradient to give a clear oil. This oil was dissolved in methylene chloride (5 mL) and treated with trifluoroacetic acid (1 mL, 10 mmol). After stirring for 1 hour, the reaction mixture was concentrated in vacuo and purified by automated flash column chromatography (0%-5% methanol in dichloromethane gradient elution) to yield the title compound (50 mg, 61%) as a white solid.

$^1$HNMR (400 MHz, d6-DMSO): δ 3.81 (s, 3H), 3.86 (s, 3H), 6.29 (m, 1H), 6.92 (m, 1H), 6.97 (m, 1H), 7.09 (m, 1H), 7.19 (m, 1H), 7.34 (m, 2H), 7.48 (m, 3H), 7.70 (m, 1H), 7.77 (m, 1H), 7.96 (m, 1H), 8.15 (m, 1H), 12.80 (s, 1H).

LCMS Rt=1.63 minutes; MS m/z 544 [MH]$^+$

EXAMPLE 20

3-Cyano-N-(5-fluoropyridin-2-yl)-4-{[3-(1-methyl-1H-pyrazol-5-yl)biphenyl-4-yl]oxy}benzenesulfonamide

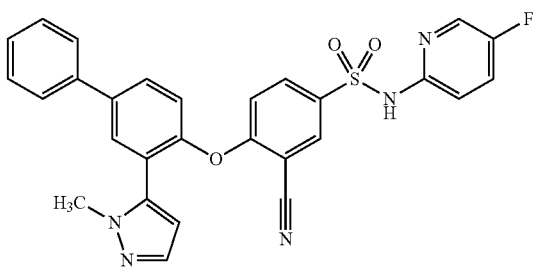 [SMILES: Cn1nccc1-c1cc(-c2ccccc2)ccc1Oc1ccc(S(=O)(=O)Nc2ccc(F)cn2)cc1C#N]

In a pressure sealed vial, 3-(1-methyl-1H-pyrazol-5-yl)biphenyl-4-ol (Preparation 107, mg, 0.19 mmol), 3-cyano-4-fluoro-N-(5-fluoropyridin-2-yl)benzenesulfonamide (WO2010079443, 50 mg, 0.17 mmol) and potassium carbonate (70 mg, 0.51 mmol) were stirred at 90° C. in dimethyl sulfoxide for 18 hours. The mixture was cooled down to room temperature and treated with 2M hydrochloric acid (5 mL). The mixture was stirred for 1 hour and the resulting precipitate was filtered and purified by preparative HPLC to afford the title compound (17 mg, 18%) as a white solid.

LCMS Rt=3.73 minutes, MS m/z 526 [MH]$^+$

EXAMPLE 21

4-{[3'-(Aminomethyl)-3-(1-methyl-1H-pyrazol-5-yl)biphenyl-4-yl]oxy}-3-cyano-N-(1,3-thiazol-2-yl)benzenesulfonamide, hydrochloride salt

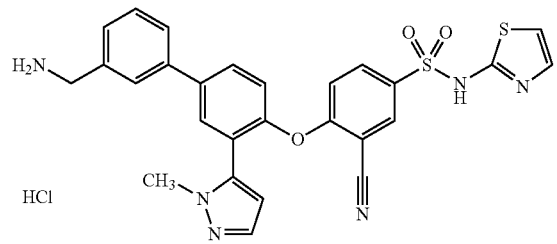 [SMILES: Cl ; Cn1nccc1-c1cc(-c2cccc(CN)c2)ccc1Oc1ccc(S(=O)(=O)Nc2nccs2)cc1C#N]

tert-Butyl-{[4'-{2-cyano-4-[(1,3-thiazol-2-ylamino)sulfonyl]phenoxy}-3'(1-methyl-1H-pyrazol-5-yl)biphenyl-3-yl]methyl}carbamate (Preparation 77, 380 mg, 0.59 mmol) was dissolved in dichloromethane (20 mL), 4M HCl in 1,4-dioxane (4 mL) was added and the reaction was stirred for 18 hours at room temperature. The reaction mixture was concentrated in vacuo, slurried in cold diethyl ether (20 ml) then filtered to afford the title compound (342 mg, 99%) as a yellow solid as the hydrochloride salt.

$^1$HNMR (400 MHz, d6-DMSO): δ 3.76 (s, 3H), 4.09 (m, 2H), 6.23 (d, 1H), 6.87 (d, 1H), 6.94 (d, 1H), 7.28 (d, 1H), 7.34 (d, 1H), 7.50 (m, 3H), 7.78 (m, 1H), 7.87 (d, 1H), 7.94 (m, 3H), 8.10 (d, 1H), 8.42 (br s, 3H).

LCMS Rt=1.02 minutes MS m/z 543 [MH]$^+$

EXAMPLE 22

5-Chloro-2-fluoro-N-(5-fluoropyridin-2-yl)-4-{[3-(1-methyl-1H-pyrazol-5-yl)biphenyl-4-yl]oxy}benzenesulfonamide

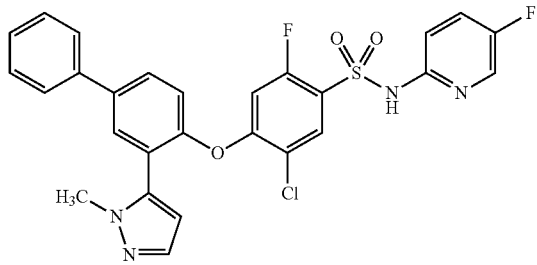 [SMILES: Cn1nccc1-c1cc(-c2ccccc2)ccc1Oc1cc(F)c(S(=O)(=O)Nc2ccc(F)cn2)cc1Cl]

5-Chloro-N-(2,4-dimethoxybenzyl)-2,4-difluoro-N-(5-fluoropyridin-2-yl)benzenesulfonamide (Preparation 105, 23 mg, 0.04 mmol), 3-(1-methyl-1H-pyrazol-5-yl)biphenyl-4-ol (Preparation 107, 9 mg, 0.04 mmol) and potassium carbonate (15 mg, 0.11 mmol) in dimethyl sulfoxide (1 mL) were stirred at room temperature for 2 hours. The mixture was treated with aqueous 2M HCl (3 mL). The resulting mixture was extracted with dichloromethane (3 mL). The dichloromethane layer was dried through a phase separating cartridge followed by treatment with trifluoroacetic acid (500 µL). The mixture was stirred for 2 hours and allowed to stand at room temperature for 18 hours. The mixture was then treated with a saturated solution of ammonium chloride (5 mL). The dichloromethane layer was separated, dried through a phase separating cartridge and evaporated in vacuo. The residue was purified by preparative HPLC to afford the title compound (14 mg, 45%).

LCMS Rt=2.55 minutes, MS m/z 551 [M-H]$^-$.

EXAMPLE 23

3-Cyano-4-({2'-[(methylamino)methyl]-3-(1-methyl-1H-pyrazol-5-yl)biphenyl-4-yl}oxy)-N-(1,3-thiazol-2-yl)benzenesulfonamide, trifluoroacetate salt

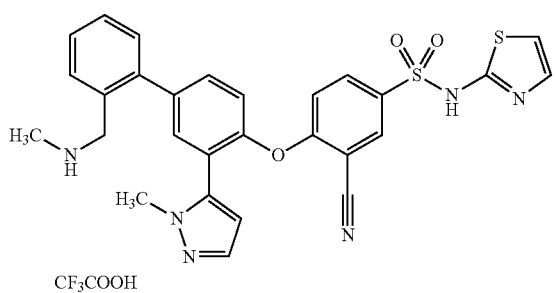 [SMILES: "CF3COOH" ; CNCc1ccccc1-c1ccc(Oc2ccc(S(=O)(=O)Nc3nccs3)cc2C#N)c(-c2ccnn2C)c1]

tert-Butyl-{[4'-{2-cyano-4-[(1,3-thiazol-2-ylamino)sulfonyl]phenoxy}-3'(1-methyl-1H-pyrazol-5-yl)biphenyl-2-yl]methyl}methylcarbamate (Preparation 65, 64 mg, 0.01 mmol) was dissolved in dichloromethane (5 mL), trifluoroacetic acid (0.2 mL) was added and the reaction was stirred for 18 hours at room temperature. The reaction mixture was concentrated in vacuo and purified by reverse phase preparative HPLC to afford the title compound (22 mg, 37%) as a white solid as the trifluoroacetate salt.

LCMS Rt=2.29 minutes MS m/z 557 [MH]$^+$, 555 [M-H]$^-$

EXAMPLE 24

5-Chloro-4-{[2-chloro-4'-fluoro-5-(pyridazin-4-yl)biphenyl-4-yl]oxy}-2-fluoro-N-(1,3,4-thiadiazol-2-yl)benzenesulfonamide

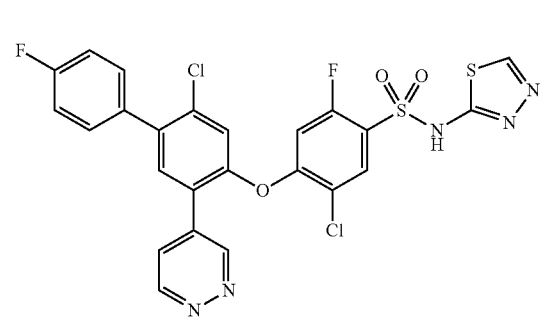 [SMILES: O=S(=O)(Nc1nncs1)c1cc(Cl)c(Oc2cc(Cl)c(-c3ccc(F)cc3)cc2-c2ccnnc2)cc1F]

5-Chloro-4-(2-chloro-4'-fluoro-5-(pyridazin-4-yl)biphenyl-4-yloxy)-N-(2,4-dimethoxybenzyl)-2-fluoro-N-(1,3,4-thiadiazol-2-yl)benzenesulfonamide (Preparation 70, 220 mg, 0.30 mmol) was dissolved in dichloromethane (2 mL) and trifluoroacetic acid (1 mL) was added. The reaction was stirred at room temperature for 3 hours. Methanol (5 mL) was added to quench the reaction and the suspension was stirred vigorously for 1 hour. The resulting precipitate was filtered through Celite™ and washed with methanol and the filtrate concentrated in vacuo. The residue was suspended in hot methanol (5 mL) and the remaining solids filtered off. The filtrate was concentrated in vacuo and the residue triturated with ethyl acetate and filtered to give the title compound (77 mg, 43%) as a white solid.

$^1$HNMR (400 MHz, d6-DMSO): δ 7.33 (m, 3H), 7.52 (s, 1H), 7.58 (dd, 2H), 7.78 (s, 1H), 7.92 (d, 2H), 8.80 (s, 1H), 9.26 (d, 1H), 9.46 (s, 1H).

LCMS Rt=3.34 minutes MS m/z 592 [M$^{35}$ClH]$^+$.

EXAMPLE 25

4-{[3-(3-Amino-1H-pyrazol-4-yl)-3'-(trifluoromethyl)biphenyl-4-yl]oxy}-5-chloro-2-fluoro-N-(1,3,4-thiadiazol-2-yl)benzenesulfonamide

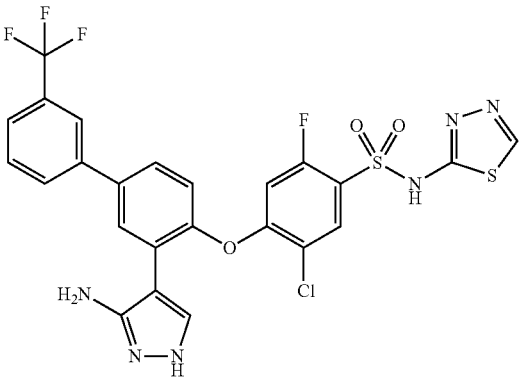 [SMILES: Nc1n[nH]cc1-c1cc(-c2cccc(C(F)(F)F)c2)ccc1Oc1cc(F)c(S(=O)(=O)Nc2nncs2)cc1Cl]

5-Chloro-N-(2,4-dimethoxybenzyl)-2-fluoro-4-(3-(3-nitro-1-(tetrahydro-2H-pyran-2-yl)-1H-pyrazol-4-yl)-3-(trifluoromethyl)biphenyl-4-yloxy)-N-(1,3,4-thiadiazol-2-yl)benzene sulfonamide (Preparation 86, 0.15 g, 0.17 mmol) was dissolved in acetonitrile (2 mL). Potassium carbonate (117 mg, 0.85 mmol), sodium dithionite (0.15 g, 0.85 mmol) and water (1 mL) were added and the reaction was heated at 40° C. for 3 hours. After cooling to room temperature, the reaction was partitioned between ethyl acetate (50 mL) and water (30 mL). The organic layer was dried over magnesium sulphate, filtered and concentrated in vacuo. The crude residue was dissolved in a 4M solution of hydrogen chloride in 1,4-dioxane (2.5 mL). The reaction was stirred at room temperature for 18 hours, concentrated in vacuo and the residue was purified by reverse phase HPLC using acetonitrile/water (5/95 to 95/5 with 0.05% formic acid as eluent to give the title compound (5.2 mg, 7%) as a white solid.

$^1$HNMR (400 MHz, CDCl$_3$): δ 3.30 (s, 2H), 6.55 (d, 1H), 7.22 (d, 1H), 7.62 (m, 4H), 7.90 (m, 4H), 8.55 (s, 1H).

LCMS Rt=2.75 minutes, MS m/z 611 [MH]$^+$

EXAMPLE 26

5-Chloro-4-{[2-chloro-3'-fluoro-5-(pyridazin-4-yl)biphenyl-4-yl]oxy}-2-fluoro-N-(1,3,4-thiadiazol-2-yl)benzenesulfonamide

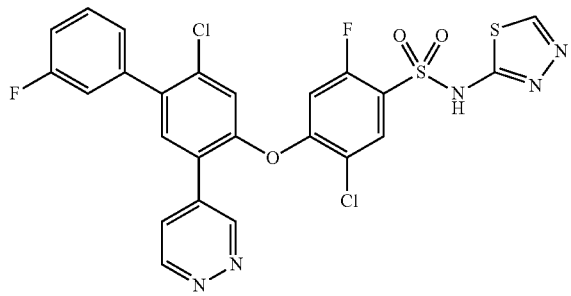 [SMILES: O=S(=O)(Nc1nncs1)c1cc(Cl)c(Oc2cc(Cl)c(-c3cccc(F)c3)cc2-c2ccnnc2)cc1F]

5-Chloro-4-(2-chloro-3'-fluoro-5-(pyridazin-4-yl)biphenyl-4-yloxy)-N-(2,4-dimethoxybenzyl)-2-fluoro-N-(1,3,4-thiadiazol-2-yl)benzenesulfonamide (Preparation 66, 165 mg, 0.22 mmol) was dissolved in dichloromethane (2 mL) and trifluoroacetic acid (1 mL) was added. The reaction was stirred at room temperature for 3 hours. Methanol (5 mL) was added to quench the reaction and the suspension stirred vigorously for 18 hours. The mixture was diluted with dichloromethane (5 mL) and the resulting precipitate was filtered through Celite™ and washed with dichloromethane (2×5 mL) and the filtrate concentrated in vacuo. The residue was dissolved in dichloromethane and methanol and passed through a short silica plug eluting with dichloromethane/methanol (98:2). The material obtained was further purified by silica gel column chromatography using (dichloromethane/methanol/acetic acid 97:3:0.5) to give the title compound (17 mg, 13%) as a white solid.

$^1$HNMR (400 MHz, d6-DMSO): δ 6.28 (t, 1H), 7.40 (m, 3H), 7.53 (m, 2H), 7.82 (s, 1H), 7.94 (m, 2H), 8.82 (s, 1H), 9.28 (d, 1H), 9.52 (s, 1H).

LCMS Rt=3.36 minutes MS m/z 592 [MH]$^+$

EXAMPLE 27

5-Chloro-4-{[2-chloro-2'-fluoro-5-(pyridazin-4-yl)biphenyl-4-yl]oxy}-2-fluoro-N-(1,3,4-thiadiazol-2-yl)benzenesulfonamide

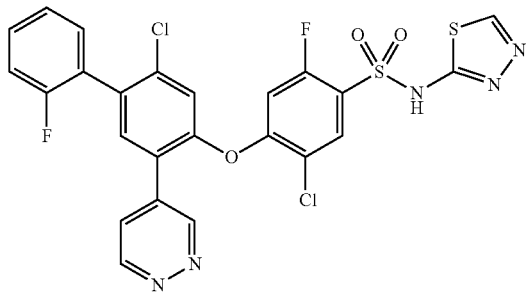 [SMILES: O=S(=O)(Nc1nncs1)c1cc(Cl)c(Oc2cc(Cl)c(-c3ccccc3F)cc2-c2ccnnc2)cc1F]

2-Chloro-2'-fluoro-5-(pyridazin-4-yl)biphenyl-4-ol (Preparation 74, 100 mg, 0.4 mmol) was dissolved in DMSO (2 mL) and potassium carbonate (92 mg, 0.66 mmol) was added followed by 5-chloro-N-(2,4-dimethoxybenzyl)-2,4-difluoro-N-(1,3,4-thiadiazol-2-l)benzenesulfonamide (Preparation 16, 154 mg, 0.33 mmol). The reaction was stirred at room temperature for 18 hours and then partitioned between ethyl acetate (50 mL) and water (40 mL). The ethyl acetate was separated, dried over anhydrous MgSO$_4$ filtered, and evaporated to give 5-chloro-4-(2-chloro-2'-fluoro-5-(pyridazin-4-yl)biphenyl-4-yloxy)-N-(2,4-dimethoxybenzyl)-2-fluoro-N-(1,3,4-thiadiazol-2-yl)benzenesulfonamide (220 mg) which was used without further purification in the next stage.

LCMS Rt=3.70 minutes, MS m/z 742 [MH]$^+$.

The crude 5-chloro-4-(2-chloro-2'-fluoro-5-(pyridazin-4-yl)biphenyl-4-yloxy)-N-(2,4-dimethoxybenzyl)-2-fluoro-N-(1,3,4-thiadiazol-2-yl)benzenesulfonamide (220 mg) was dissolved in a 4M solution of HCl in 1,4-dioxane (10 mL) and stirred at room temperature for 3 hours. The resulting precipitate was collected and purified by reverse phase chromatography using acetonitrile:water:0.05% formic acid followed by chromatography on silica gel eluting with dichloromethane/methanol 9:1 to give the title compound (8.5 mg, 3.5%) as a white solid.

LCMS Rt=2.94 minutes, MS m/z 592 [MH]$^+$.

EXAMPLE 28

5-Chloro-4-{[2-chloro-5-(pyridazin-4-yl)-3'-(trifluoromethyl)biphenyl-4-yl]oxy}-2-fluoro-N-(1,3,4-thiadiazol-2-yl)benzenesulfonamide

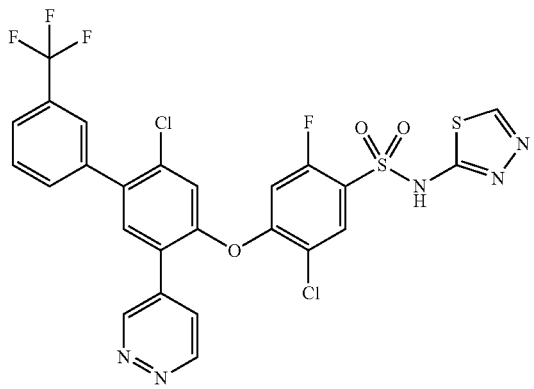 [SMILES: O=S(=O)(Nc1nncs1)c1cc(Cl)c(Oc2cc(Cl)c(-c3cccc(C(F)(F)F)c3)cc2-c2ccnnc2)cc1F]

5-Chloro-4-(2-chloro-5-(pyridazin-4-yl)-3'-(trifluoromethyl)biphenyl-4-yloxy)-N-(2,4-dimethoxybenzyl)-2-fluoro-N-(1,3,4-thiadiazol-2-yl)benzenesulfonamide (Preparation 53, 231 mg, 0.29 mmol) was dissolved in dichloromethane (2 mL) and trifluoroacetic acid (1 mL) added. The resulting solution was stirred at room temperature for 18 hours. Methanol (2 mL) was added and the reaction was stirred for 10 minutes. The resulting mixture was evaporated and azeotroped with methanol (2×10 mL). The residue was partitioned between ethyl acetate (50 mL) and water (20 mL). The ethyl acetate was separated and dried over MgSO$_4$ and evaporated. The residue was chromatographed on silica eluting with dichloromethane:methanol:acetic acid 100:0:0 to 95:5:0.5 in 1% stages of methanol. The column product was stirred in dichloromethane (10 mL) for 20 minutes, the solid filtered off, and stirred in dichloromethane (5 mL) at reflux for 10 minutes. The solid was filtered to give the title compound (45 mg, 25%) as a white solid.

$^1$HNMR (400 MHz, d-6DMSO): δ 7.38 (d, 1H), 7.56 (s, 1H), 7.74 (m, 1H), 7.80 (m, 1H), 7.84-7.94 (m, 6H), 8.80 (s, 1H), 9.27 (d, 1H), 9.50 (s, 1H).

LCMS (5.0 min) Rt=3.52 minutes, MS m/z 642 [MH]$^+$.

EXAMPLE 29

5-Chloro-4-{[4'-chloro-3-(pyridazin-4-yl)-3'-(trifluoromethyl)biphenyl-4-yl]oxy}-2-fluoro-N-(1,3,4-thiadiazol-2-yl)benzenesulfonamide

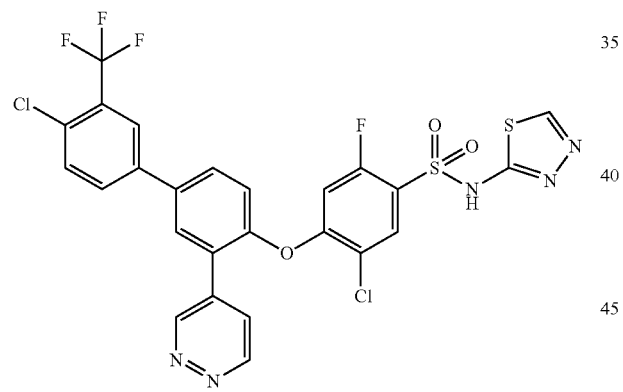

5-Chloro-4-(4'-chloro-3-(pyridazin-4-yl)-3'-(trifluoromethyl)biphenyl-4-yloxy)-N-(2,4-dimethoxybenzyl)-2-fluoro-N-(1,3,4-thiadiazol-2-yl)benzenesulfonamide (Preparation 57, 135 mg, 0.17 mmol) was dissolved in a 4M solution of HCl in dioxane (5 mL), methanol (5 mL) added and the resulting mixture was stirred at 50° C. for 6 hours. The reaction mixture was evaporated and the residue partitioned between ethyl acetate (50 mL) and water (50 mL). The ethyl acetate was separated, dried over MgSO$_4$, filtered and evaporated. The residue was chromatographed on silica eluting with a gradient of dichloromethane:methanol:acetic acid 100:0:0 to 95:4:0.4 to give the title compound (75 mg, 68%) as a white solid.

$^1$HNMR (400 MHz, CDCl$_3$): δ 7.23 (d, 1H), 7.27 (d, 1H), 7.84, (d 1H), 7.94 (m, 3H), 8.10 (m, 1H), 8.13 (s, 1H), 8.20 (s, 1H), 8.80 (s, 1H), 9.31 (d, 1H), 9.55 (s, 1H).

LCMS (5.0 min) Rt=3.56 minutes, MS m/z 642 [MH]$^+$.

EXAMPLE 30

5-Chloro-2-fluoro-4-{2-(pyridazin-4-yl)-4-[6-(trifluoromethyl)pyridin-3-yl]phenoxy}-N-(1,3,4-thiadiazol-2-yl)benzenesulfonamide

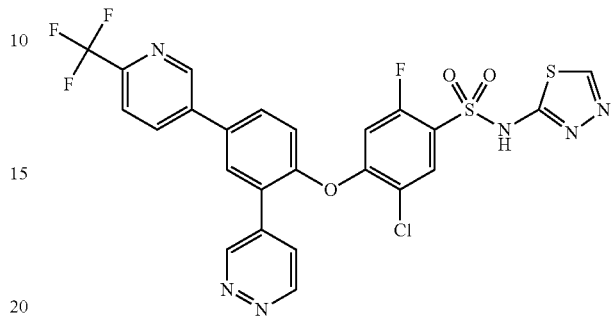

5-Chloro-N-(2,4-dimethoxybenzyl)-2-fluoro-4-(2-(pyridazin-4-yl)-4-(6-(trifluoromethyl)pyridin-3-yl)phenoxy)-N-(1,3,4-thiadiazol-2-yl)benzenesulfonamide (Preparation 58, 250 mg, 0.329 mmol) was dissolved in a 4M solution of HCl in 1,4-dioxane (0.9 mL, 3.29 mmol). The reaction mixture was stirred at room temperature for 18 hours and then concentrated in vacuo. The resulting residue was purified by reverse phase chromatography on the ISCO system using acetonitrile:water 0.1% formic acid to afford the title compound (160 mg, 80%) as a white solid.

$^1$HNMR (400 MHz, d-6DMSO): δ 7.30 (dd, 2H), 7.80 (d, 1H), 7.89-8.02 (m, 3H), 8.20 (d, 1H), 8.50 (d, 1H), 8.75 (s, 1H), 9.20 (d, 1H), 9.31 (d, 1H), 9.56 (s, 1H).

$^{19}$F NMR (400 MHz, d-6DMSO): δ −66.2, −106.7

LCMS Rt=3.13 minutes, MS m/z 609 [MH]$^+$.

EXAMPLE 31

5-Chloro-2-fluoro-4-{2-(pyridazin-4-yl)-4-[6-(trifluoromethyl)pyridin-2-yl]phenoxy}-N-(1,3,4-thiadiazol-2-yl)benzenesulfonamide

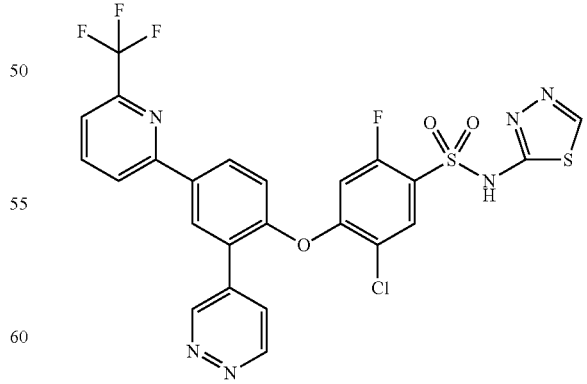

5-Chloro-N-(2,4-dimethoxybenzyl)-2-fluoro-4-(2-pyridazin-4-yl)-6-(trifluoromethyl)pyridine-2-yl)phenoxy-N-(1,3,4-thiadiazol-2-yl)benzenesulfonamide (Preparation 82, 50 mg, 0.06 mmol) was dissolved in 4M solution of HCl in 1,4-dioxane (2 mL). The reaction was stirred at room temperature for 5 hours, concentrated in vacuo and the residue was purified by reverse phase HPLC using acetonitrile:water:0.5% formic acid to give the title compound (9.8 mg, 25%) as a white solid.

¹HNMR (400 MHz, d6-DMSO): δ 7.35 (d, 1H), 7.38 (d, 1H), 7.90 (m, 3H), 8.24 (m, 1H), 8.30 (m, 1H), 8.40 (s, 1H), 8.45 (d, 1H), 8.80 (s, 1H), 9.36 (d, 1H), 9.58 (s, 1H).

LCMS Rt=3.27 minutes, MS m/z 609 [MH]⁺.

EXAMPLE 32

4-{[3-(5-Amino-1H-pyrazol-4-yl)-3'-cyanobiphenyl-4-yl]oxy}-5-chloro-2-fluoro-N-(1,3,4-thiadiazol-2-yl)benzenesulfonamide

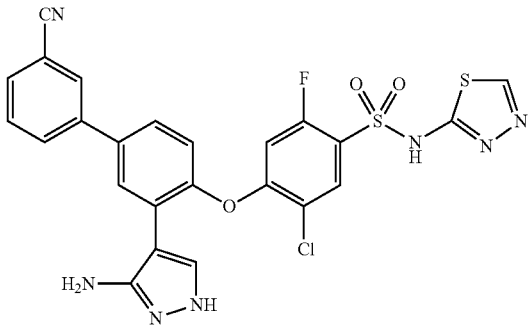

5-Chloro-4-(3'-cyano-3-(3-nitro-1H-pyrazol-4-yl)biphenyl-4-yloxy)-2-fluoro-N-(1,3,4-thiadiazol-2-yl)benzenesulfonamide (Preparation 62, 51 mg, 0.0853 mmol) was dissolved in acetonitrile (1 mL) and heated at 50° C. Potassium carbonate (58.8 mg, 0.426 mmol) followed by sodium dithionite (59.4 mg, 0.341 mmol) and water (1 mL) were added. The reaction mixture was heated at 50° C. for 2 hours, cooled to room temperature and partitioned between EtOAc (10 mL) and water (5 mL). The aqueous phase was separated and extracted with EtOAc (2×3 mL) and the combined organic phases were washed with a saturated solution of brine (3 mL), dried over MgSO₄ and concentrated in vacuo. The crude residue was purified by reverse phase HPLC.

LCMS Rt=2.44 minutes, MS m/z 568 [MH]⁺.

EXAMPLE 33

5-Chloro-2-fluoro-4-{2-(pyridazin-4-yl)-4-[2-(trifluoromethyl)pyridin-4-yl]phenoxy}-N-1,3,4-thiadiazol-2-yl)benzenesulfonamide

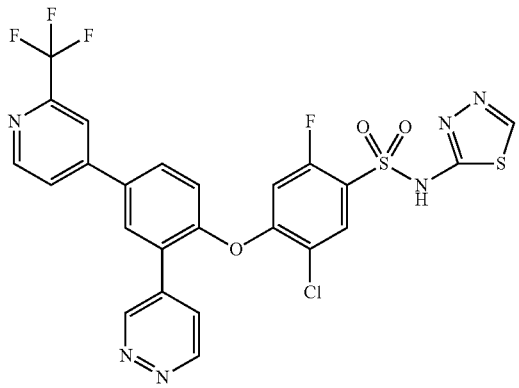 [SMILES: O=S(=O)(Nc1nncs1)c1cc(Cl)c(Oc2ccc(-c3cccc(C(F)(F)F)n3)cc2-c2ccnnc2)cc1F]

5-Chloro-N-(2,4-dimethoxybenzyl)-2-fluoro-4-(2-pyridazin-4-yl)-4-(2-trifluoromethyl)-pyridine-4-yl)phenoxy)-N-1,3,4-thidiazol-2-yl)benzenesulfonamide (Preparation 78, 0.2 g, 0.26 mmol) was dissolved in a mixture of a 4M solution of HCl in 1,4-dioxane (4 mL) and methanol (3 mL). The reaction was stirred at room temperature for 5 hours, concentrated in vacuo and residue was purified by reverse phase HPLC using acetonitrile:water:0.5% formic acid to give the title compound (26 mg, 16%) as a white solid.

¹HNMR (400 MHz, CD₃OD): δ 7.02 (d, 1H), 7.14 (d, 1H), 8.02 (m, 4H), 8.10 (d, 2H), 8.60 (s, 1H), 8.80 (d, 1H), 9.12 (d, 1H), 9.57 (s, 1H).

LCMS Rt=3.10 minutes, MS m/z 609 [MH]⁺.

EXAMPLE 34

5-Chloro-2-fluoro-4-({3-[2-(piperazin-1-yl)pyridin-4-yl]-4'-(trifluoromethyl)biphenyl-4-yl}oxy)-N-(1,3,4-thiadiazol-2-yl)benzenesulfonamide, hydrochloride

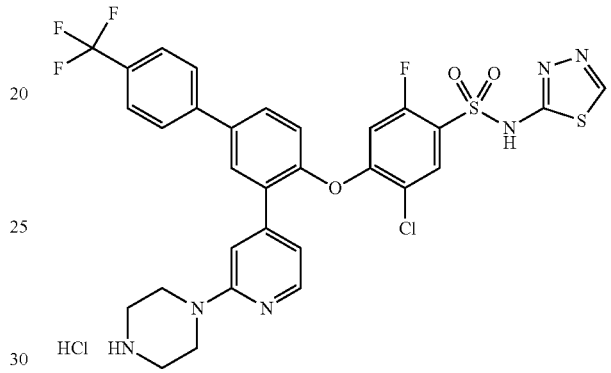

tert-Butyl 4-(4-(4-(2-chloro-4-(N-(2,4-dimethoxybenzyl)-N-(1,3,4-thiadiazol-2-yl)sulfamoyl)-5-fluorophenoxy)-4'-(trifluoromethyl)biphenyl-3-yl)pyridin-2-yl)piperazine-1-carboxylate (Preparation 113, 340 mg, 0.361 mmol) was dissolved in methanol (1 mL) and a 4M solution of hydrogen chloride in 1,4-dioxane (3 mL) was added. The reaction mixture was stirred at room temperature for 3 hours and then concentrated in vacuo. The resulting residue was purified by reverse phase chromatography using the ISCO™ system and acetonitrile/water 5/95-95/5 with 0.1% formic acid as eluent to afford the title compound (90 mg, 34%) as a white solid.

¹HNMR (400 MHz, d-6DMSO): δ 3.08 (m, 4H), 3.69 (m, 4H), 6.74 (d, 1H), 6.91 (d, 1H), 7.00 (s, 1H), 7.32 (d, 1H), 7.69 (d, 1H), 7.80-7.95 (m, 4H), 7.98 (d, 2H), 8.11 (d, 1H), 8.56 (s, 1H), 9.06 (br s, 1H).

¹⁹F NMR (376 MHz, DMSO-d6): δ −107.4, −60.9.

LCMS Rt=2.53 minutes. MS m/z 691 [MH]⁺.

EXAMPLE 35

5-Chloro-2-fluoro-4-({3-[2-(piperazin-1-yl)pyridin-4-yl]-4'-(trifluoromethyl)biphenyl-4-yl}oxy)-N-(pyrimidin-4-yl)benzenesulfonamide hydrochloride salt

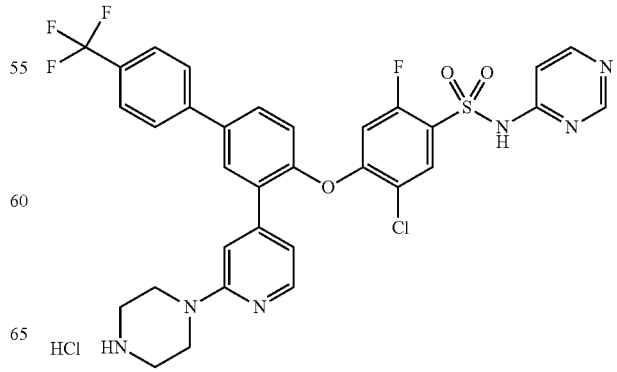

A 4M solution of hydrogen chloride in 1,4-dioxane (10 mL) was added to a solution of tert-butyl 4-(4-(4-(2-chloro-4-(N-(2,4-dimethoxybenzyl)-N-(pyrimidin-4-yl)sulfamoyl)-5-fluorophenoxy)-4'-(trifluoromethyl)biphenyl-3-yl)pyridin-2-yl)piperazine-1-carboxylate (Preparation 109, 310 mg, 0.332 mmol) in methanol (2 mL). The reaction mixture was stirred at room temperature for 3 hours and then concentrated in vacuo. The residue was purified by reverse phase chromatography (acetonitrile/water with 0.1% formic acid) to afford the title compound (196 mg, 82%) as a white solid.

$^1$HNMR (400 MHz, d-6DMSO): δ 3.08 (br s, 4H), 3.72 (br s, 4H), 6.61 (d, 1H), 6.70 (d, 1H), 6.94 (d, 1H), 7.04 (s, 1H), 7.30 (d, 1H), 7.78-7.87 (m, 5H), 7.95-7.99 (m, 3H), 8.12 (d, 1H), 8.26 (s, 1H).

$^{19}$FNMR (376 MHz, d6-DMSO): δ −108.02 (F), −60.91 (CF$_3$).

LCMS Rt=2.95 minutes, m/z 685 [MH]$^+$.

EXAMPLE 36

5-Chloro-4-[(6-chloro-3'-fluoro-4-pyridazin-4-ylbiphenyl-3-yl)oxy]-2-fluoro-N-1,3,4-thiadiazol-2-yl-benzenesulfonamide

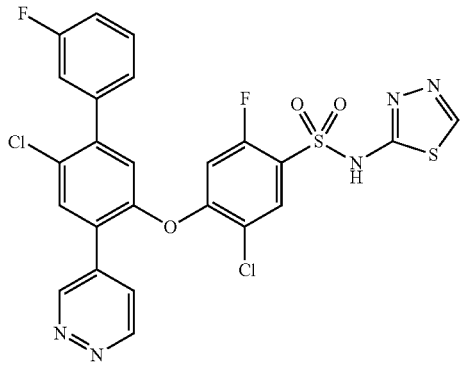 [SMILES: O=S(=O)(Nc1nncs1)c1cc(Cl)c(Oc2cc(-c3cccc(F)c3)c(Cl)cc2-c2ccnnc2)cc1F]

5-Chloro-4-(6-chloro-3'-fluoro-4-(pyridazin-4-yl)biphenyl-3-yloxy)-N-(2,4-dimethoxybenzyl)-2-fluoro-N-(1,3,4-thiadiazol-2-yl)benzenesulfonamide (Preparation 97, 60 mg, 0.08 mmol) was dissolved in a 4M solution of HCl in dioxane (5 mL). The reaction was stirred for 18 hours at room temperature and then evaporated in vacuo. The residue was dissolved in ethyl acetate (5 mL) washed with water (2×5 mL), dried over MgSO$_4$, filtered and concentrated in vacuo. The residue was purified by flash chromatography eluting with dichloromethane:methanol:acetic acid (97:2.7:0.3) to give 30 mg of the title compound. The compound was further purified by preparative HPLC to give the title compound (3.6 mg, 7.5%) as a solid.

$^1$H NMR (400 MHz, CDCl$_3$): δ 7.21-7.36 (m, 4H), 7.40 (s, 1H), 7.49-7.55 (m, 1H), 7.83 (d, 1H), 7.87-7.89 (m, 1H), 8.02 (s, 1H), 8.75 (s, 1H), 9.28-9.29 (m, 1H), 9.44-9.45 (m, 1H).

$^{19}$F NMR (400 MHz, CDCl$_3$): δ −107, −113.

LCMS (4.5 min acidic run) Rt=3.34 minutes, m/z 592 [MH]$^+$.

EXAMPLE 37

5-Chloro-4-[(6-chloro-4'-fluoro-4-pyridazin-4-ylbiphenyl-3-yl)oxy]-2-fluoro-N-1,3,4-thiadiazol-2-yl-benzenesulfonamide

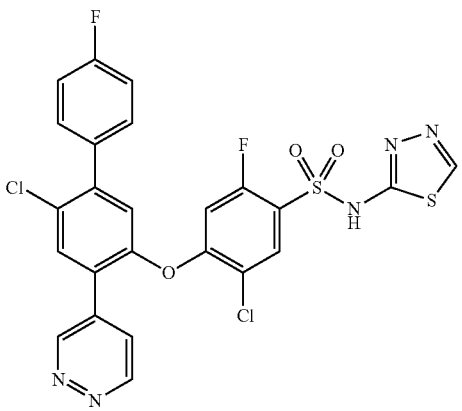 [SMILES: O=S(=O)(Nc1nncs1)c1cc(Cl)c(Oc2cc(-c3ccc(F)cc3)c(Cl)cc2-c2ccnnc2)cc1F]

5-Chloro-4-(6-chloro-4'-fluoro-4-(pyridazin-4-yl)biphenyl-3-yloxy)-N-(2,4-dimethoxybenzyl)-2-fluoro-N-(1,3,4-thiadiazol-2-yl)benzenesulfonamide (Preparation 101, 100 mg, 0.13 mmol) was dissolved in a 4M solution of HCl in dioxane (10 mL). The reaction mixture was stirred for 18 hours at room temperature. Methanol (50 mL) was added to the reaction mixture and the suspension was concentrated in vacuo. The crude residue was purified by reverse phase semi preparative HPLC (solvent A: 0.05% formic acid in acetonitrile, solvent B: 0.05% formic acid in water; flow rate: 12.5 ml/min; gradient: 0 min 10% A, 2.5 min 10% A, 32.5 min 95% A, 37.5 min 95% A then return to initial conditions) to afford the title compound (46 mg, 60%) as a solid.

$^1$H NMR (400 MHz, CDCl$_3$): δ 6.94 (m, 1H), 7.22 (m, 3H), 7.52 (m, 2H), 7.90 (s, 1H), 7.95 (m, 2H), 8.55 (s, 1H), 9.23 (m, 1H), 9.47 (m, 1H).

$^{19}$F NMR (400 MHz, CD$_3$OD+CD$_3$CN drops): δ −107.7, −115.3

LCMS Rt=3.31 minutes MS m/z 592 [MH]$^+$.

EXAMPLE 38

5-Chloro-4-[(6-chloro-2'-fluoro-4-pyridazin-4-ylbiphenyl-3-yl)oxy]-2-fluoro-N-1,3,4-thiadiazol-2-yl-benzenesulfonamide

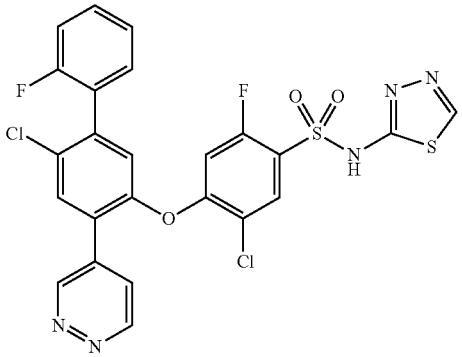 [SMILES: O=S(=O)(Nc1nncs1)c1cc(Cl)c(Oc2cc(-c3ccccc3F)c(Cl)cc2-c2ccnnc2)cc1F]

Hydrogen chloride in dioxane (4M, 1.5 mL, 6.00 mmol) was added to a solution of 5-chloro-4-(6-chloro-2'-fluoro-4-(pyridazin-4-yl)biphenyl-3-yloxy)-N-(2,4-dimethoxybenzyl)-2-fluoro-N-(1,3,4-thiadiazol-2-yl)benzenesulfonamide (Preparation 92, 220 mg, 0.27 mmol) in methanol (1.5 mL) and the reaction stirred at room temperature for 18 hours. The mixture was evaporated to dryness and dissolved in dimethylsulfoxide (4.0 mL) and methanol (2.0 mL). The resulting precipitate was filtered, washed with methanol (2.0 mL) and the filtrate purified by preparative HPLC using a Phenomenex Luna C18 5 u 110 A 21.2×150 mm using acetonitrile:water as eluent to give the title compound (92 mg, 56%) as a beige coloured solid.

$^1$H-NMR (400 MHz, CDCl$_3$): δ 7.26 (d, 1H), 7.32 (m, 1H), 7.34 (m, 1H), 7.40 (m, 1H), 7.44 (m, 1H), 7.52 (m, 1H), 7.87 (d, 1H), 7.93 (dd, 1H), 8.02 (s, 1H), 8.78 (s, 1H), 9.31 (dd, 1H), 9.49 (t, 1H).

$^{19}$F-NMR (400 MHz, CDCl$_3$): δ −106.66, −114.13

LCMS (4.5 min) Rt=3.26 minutes MS m/z 592 [MH]$^+$.

EXAMPLE 39

5-chloro-4-[(3'-cyano-3-pyridazin-4-ylbiphenyl-4-yl)oxy]-2-fluoro-N-1,3,4-thiadiazol-2-ylbenzenesulfonamide

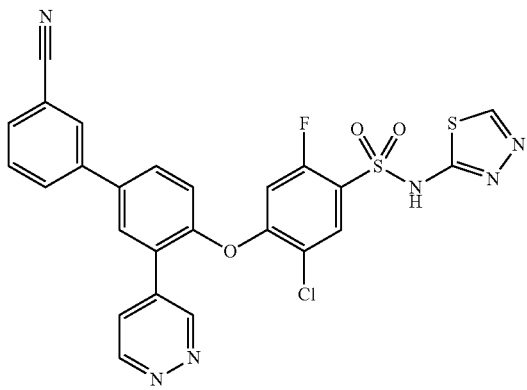 [SMILES: N#Cc1cccc(-c2ccc(Oc3cc(F)c(S(=O)(=O)Nc4nncs4)cc3Cl)c(-c3ccnnc3)c2)c1]

5-Chloro-4-(3'-cyano-3-(pyridazin-4-yl)biphenyl-4-yloxy)-N-(2,4-dimethoxybenzyl)-2-fluoro-N-(1,3,4-thiadiazol-2-yl)benzenesulfonamide (Preparation 118, 550 mg, 0.77 mmol) was dissolved in methanol (2 mL) and a 4M solution of hydrogen chloride in 1,4-dioxane (10 mL) was added. The reaction mixture was stirred at room temperature for 18 hours and then concentrated in vacuo. The residue was co-evaporated with methanol and then purified by reverse phase chromatography (acetonitrile/water both with 0.1% formic acid) to give the title compound (303 mg, 70%) as a white solid.

LCMS Rt=2.62 minutes, MS m/z 565 [MH]$^+$.

$^1$HNMR (400 MHz, d-6DMSO): δ 7.31-7.25 (m, 2H), 7.68 (t, 1H), 7.86 (d, 1H), 7.94-7.91 (m, 2H), 7.99-7.97 (m, 1H), 8.16-8.13 (m, 2H), 8.35 (s, 1H), 8.80 (s, 1H), 9.30 (d, 1H), 9.55 (s, 1H).

$^{19}$FNMR (376 MHz, d-6DMSO): δ −106.67 (s, 1 F)

EXAMPLE 40

5-chloro-2-fluoro-4-{[3-(2-piperazin-1-ylpyridin-4-yl)-4'-(trifluoromethyl)biphenyl-4-yl]oxy}-N-pyrimidin-2-ylbenzenesulfonamide

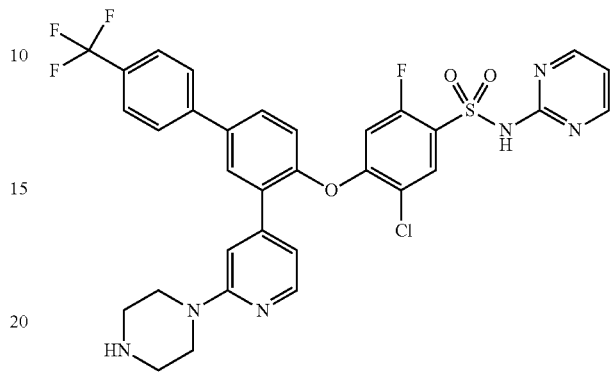

tert-Butyl 4-(4-(4-(2-chloro-4-(N-(2,4-dimethoxybenzyl)-N-(pyrimidin-2-yl)sulfamoyl)-5-fluorophenoxy)-4'-(trifluoromethyl)biphenyl-3-yl)pyridin-2-yl)piperazine-1-carboxylate (Preparation 122, 360 mg, 0.385 mmol) was dissolved in a 4M solution of hydrogen chloride in 1,4-dioxane (5 mL). The reaction mixture was stirred at room temperature for 20 hours and then concentrated in vacuo. The residue was purified by reverse phase chromatography (acetonitrile/water both with 0.1% formic acid) to give the title compound (30 mg, 11%) as a white solid.

$^1$HNMR (400 MHz, d6-acetone): δ 3.12 (br s, 4H), 3.72 (br s, 4H), 6.25 (d, 1H), 6.60 (s, 1H), 6.74-6.72 (m, 1H), 7.17-7.13 (m, 1H), 7.61-7.56 (m, 5H), 8.02-7.99 (m, 2H), 8.34-8.32 (m, 3H), 8.65 (br s, 2H)

$^{19}$FNMR (376 MHz, acetone-d6): δ −108.65 (F), −62.52 (CF$_3$)

LCMS Rt=2.36 minutes, MS m/z 685 [MH]$^+$.

The following Examples may be prepared by the methods described in the aforementioned Schemes, foregoing Examples and the corresponding Preparations, or by processes similar to either:

5-chloro-2-fluoro-4-{[3-(2-piperazin-1-ylpyridin-4-yl)-4'-(trifluoromethyl)biphenyl-4-yl]oxy}-N-1,3-thiazol-4-ylbenzenesulfonamide;

4-{[3-(5-amino-1H-pyrazol-4-yl)-4'-(trifluoromethyl)biphenyl-4-yl]oxy}-5-chloro-2-fluoro-N-1,3-thiazol-4-ylbenzenesulfonamide; and 5-chloro-2-fluoro-4-{[3-pyridazin-4-yl-4'-(trifluoromethyl)biphenyl-4-yl]oxy}-N-1,3-thiazol-4-ylbenzenesulfonamide.

PREPARATION 1

3'-(trifluoromethyl)biphenyl-4-ol

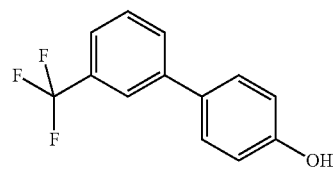 [SMILES: Oc1ccc(-c2cccc(C(F)(F)F)c2)cc1]

An aqueous solution of sodium hydrogen carbonate (6.9 g in 18 mL water, 82 mmol) was added to a stirred solution of 3-trifluoromethylbenzeneboronic acid (7.77 g, 41 mmol) and 4-iodophenol (6.0 g, 30 mmol) in 1,4-dioxane (90 mL). The reaction mixture was degassed, then tetrakis(triphenylphosphine) palladium (0) (1.58 g, 1.36 mmol) was added and the reaction mixture heated at 100° C. for 18 hours. The mixture was diluted with a 2M aqueous solution of HCl and extracted with ethyl acetate (50 mL). The organic layer was separated, dried over anhydrous magnesium sulfate, filtered and concentrated in vacuo. The residue was purified by silica gel column chromatography (5%-40% ethyl acetate in heptane gradient elution) to afford the title compound (2.17 g, 30%) as an oil.

$^1$HNMR (d6-DMSO): δ 4.95 (br s, 1H), 6.95 (m, 2H), 7.45-7.60 (m, 4H), 7.70 (m, 1H), 7.80 (m, 1H).

PREPARATION 2

3-Iodo-3'-(trifluoromethyl)biphenyl-4-ol

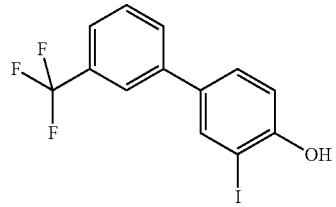 [SMILES: Oc1ccc(-c2cccc(C(F)(F)F)c2)cc1I]

To a solution of 3'-(trifluoromethyl)biphenyl-4-ol (Preparation 1, 2.17 g, 9.11 mmol) in acetic acid (20 mL) at 0° C. was added N-iodosuccinimide (2.05 g, 9.11 mmol). The reaction was allowed to warm to room temperature and stirred for 48 hours before the addition of water (20 mL). The reaction mixture was extracted with dichloromethane (2×20 mL) and the combined extracts were washed with saturated aqueous sodium thiosulfate solution, dried over anhydrous magnesium sulfate, filtered and concentrated in vacuo. The residue was purified by silica gel column chromatography (2%-20% ethyl acetate in heptane gradient elution) to afford the title compound (1.30 g, 39%).

LCMS Rt=3.54 minutes MS m/z 363 [M-H]

PREPARATION 3

3-Pyridazin-4-yl-3'-(trifluoromethyl)biphenyl-4-ol

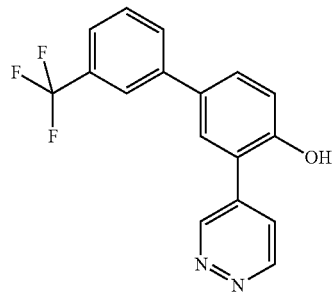 [SMILES: Oc1ccc(-c2cccc(C(F)(F)F)c2)cc1-c1ccnnc1]

To a solution of 4-(tributylstannyl)pyridazine (1.71 g, 4.64 mmol) and 3-iodo-3'-(trifluoromethyl)biphenyl-4-ol (Preparation 2, 1.30 g, 3.57 mmol) in N,N-dimethylformamide (20 mL) was added caesium fluoride (1.10 g, 7.14 mmol). The mixture was degassed before the addition of tetrakis(triphenylphosphine) palladium (0) (412 mg, 0.357 mmol), then heated to 45° C. for 4 hours. The reaction was concentrated in vacuo and purified by silica gel column chromatography (0%-20% methanol in dichloromethane gradient elution). The residue was triturated with acetonitrile and filtered to afford the title compound (420 mg, 37%) as a solid.

$^1$HNMR (d6-DMSO): δ 7.23 (m, 1H), 7.60-7.75 (m, 3H), 7.83 (m, 1H), 7.96-8.10 (m, 3H), 9.23 (s, 1H), 10.48 (m, 1H)

LCMS Rt=2.93 minutes MS m/z 317 [MH]+

PREPARATION 4

3-Pyridazin-4-ylbiphenyl-4-ol

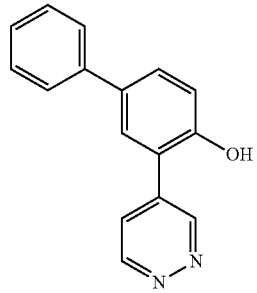 [SMILES: Oc1ccc(-c2ccccc2)cc1-c1ccnnc1]

3-Iodobiphenyl-4-ol (1 g, 3.4 mmol) was mixed with 4-(tributylstannyl)pyridazine (1.25 g 3.4 mmol), caesium fluoride (1.03 g 6.8 mmol), tetrakis(triphenylphosphine) palladium (0) (195 mg, 0.17 mmol) and copper iodide (128 mg 0.68 mmol) in acetonitrile (10 mL). The reaction was degassed 3 times before being placed under nitrogen and heated to 45° C. for 16 hours. The reaction was diluted with acetonitrile (20 mL), washed with heptane (2×20 mL) then absorbed onto silica and purified by silica gel column chromatography (ISCO™, 40 g, 50%-100% ethyl acetate in heptane gradient elution) to afford the title compound (270 mg, 32%) as a pale yellow solid.

$^1$HNMR (CDCl$_3$): δ 7.11 (d, 1H), 7.31 (m, 1H), 7.42 (m, 2H) 7.63 (m, 1H) 7.68 (m, 2H) 7.78 (m, 1H), 7.98 (m, 1H) 9.23 (m, 1H), 9.57 (m, 1H) 10.38 (br s, 1H)

LCMS Rt=1.52 minutes MS m/z 249 [MH]$^+$

PREPARATION 5

4-Bromopyridazine hydrobromide

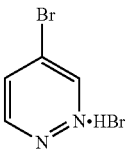

3-Bromofuran (15 g, 102 mmol) and potassium acetate (27.6 g, 281 mmol) were suspended in acetic acid (90 mL). Bromine (5.26 mL, 102 mmol) in acetic acid (45 mL) was added dropwise. The reaction mixture was then stirred for one hour and then concentrated in vacuo and azeotropically dried with toluene (×3). The residue was dissolved in ethanol (150 mL) and hydrazine hydrate (15 mL, 309 mmol) was added dropwise to the solution, which was then stirred at room temperature for two hours. The reaction was diluted with tert-butylmethyl ether (300 mL) and a solution of saturated aqueous brine (200 mL). The aqueous layer was separated and extracted with further tert-butylmethyl ether and then with ethyl acetate (×2). The organic layers were combined, dried over anhydrous sodium sulfate, filtered, and concentrated in vacuo. The resulting residue was dissolved in 1,4-dioxane (500 mL) and hydrobromic acid in acetic acid (15 mL) was added dropwise. A brown solid formed. The reaction mixture was concentrated in vacuo and the resulting solid triturated with acetone and filtered to yield the title compound (11 g, 46%) as a brown solid.

$^1$HNMR (d$_6$-DMSO): δ 8.11 (m, 1H), 9.11 (d, 1H), 9.49 (s, 1H)

LCMS Rt=0.75 minutes MS m/z 159 [MH]+

PREPARATION 6

4-(5-Chloro-2-methoxyphenyl)pyridazine

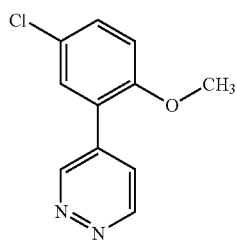

To an argon purged flask containing toluene (187 mL), ethanol (20.6 mL) and a 2M aqueous solution of sodium carbonate (132.3 mL) was added 4-bromopyridazine hydrobromide (Preparation 5, 15 g, 64 mmol), 5-chloro-2-methoxybenzeneboronic acid (13.4 g, 72 mmol) and tetrakis(triphenylphosphine) palladium (0) (3.2 g, 2.8 mmol). The flask was purged with argon again, then the reaction mixture heated to 110° C. for 4 hours. The mixture was filtered through Celite™ and the filtrate concentrated in vacuo. The residue was partitioned between ethyl acetate and water. The organic layer was washed with water and brine, then dried over anhydrous sodium sulfate, filtered and concentrated in vacuo. The crude residue was dissolved in ethyl acetate and extracted with a 2M aqueous solution of hydrogen chloride (×3). The aqueous layer was basified with sodium hydrogen carbonate and extracted with ethyl acetate. The organic layer was then washed with water and brine, dried over anhydrous sodium sulfate, filtered and concentrated in vacuo to afford the title compound (8 g, 58%).

$^1$HNMR (CDCl$_3$): δ 3.84 (s, 3H), 6.96 (d, 1H), 7.34 (s, 1H), 7.38-7.41 (dd, 1H), 7.61 (d, 1H), 9.20-9.21 (d, 1H), 9.37 (s, 1H).

LCMS Rt=2.89 minutes MS m/z 221 [MH]+

PREPARATION 7

4-Chloro-2-pyridazin-4-ylphenol

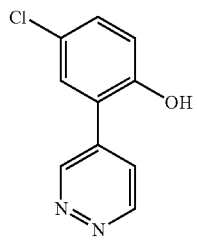 [SMILES: Oc1ccc(Cl)cc1-c1ccnnc1]

To a stirred solution of 4-(5-chloro-2-methoxyphenyl)pyridazine (Preparation 6, 22 g, 100 mmol) in dichloromethane (200 mL) at 0° C. was added drop wise a solution of boron tribromide (48 mL, 499 mmol) in dichloromethane (200 mL). The reaction mixture was stirred at room temperature for 18 hours. The reaction was quenched by pouring onto crushed ice and basifying the mixture to pH 8 with sodium hydrogen carbonate. The mixture was extracted with dichloromethane. The aqueous layer was extracted further with ethyl acetate. The organics were combined and dried over anhydrous sodium sulfate, filtered and concentrated in vacuo. The crude residue was purified by silica gel column chromatography (0%-4% methanol in dichloromethane gradient elution) to afford the title compound (16.5 g, 80%)

$^1$HNMR (d$_6$-DMSO): δ 6.99 (d, 1H), 7.31 (dd, 1H), 7.53 (d, 1H), 7.86 (m, 1H), 9.20 (d, 1H), 9.41 (s, 1H), 10.45 (s, 1H).

LCMS Rt=2.81 minutes Ms m/z 207 [MH]+

PREPARATION 8

3-Pyridazin-4-yl-4'-(trifluoromethyl)biphenyl-4-ol

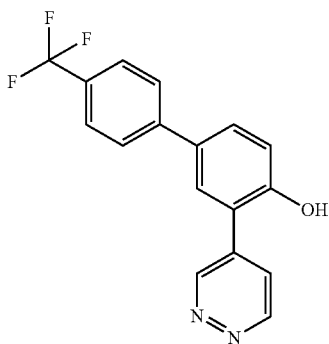 [SMILES: Oc1ccc(-c2ccc(C(F)(F)F)cc2)cc1-c1ccnnc1]

To a solution of 4-chloro-2-pyridazin-4-ylphenol (Preparation 7, 1.5 g, 7.26 mmol) and 4-trifluoromethylbenzene boronic acid (3.45 g, 18.1 mmol) in 1,4-dioxane (20 mL) was added a solution of potassium carbonate (2.0 g, 14.5 mmol) in water (4 mL). The reaction mixture was degassed, then bis (tri-t-butylphosphine) palladium (0) (371 mg, 0.726 mmol) added and the reaction mixture heated to 100° C. for 18 hours. The mixture was diluted with a 2M aqueous solution of hydrogen chloride and brine, then extracted with ethyl acetate. The organic layer was separated and dried over anhydrous magnesium sulfate, filtered and concentrated in vacuo. The residue was purified by silica gel column chromatography (0%-100% ethyl acetate in dichloromethane gradient elution) to afford the title compound as a solid (940 mg, 41%).

¹HNMR (d₆-DMSO): δ 7.13 (d, 1H), 7.68-7.77 (m, 3H), 7.83-8.02 (m, 4H), 9.23 (s, 1H), 9.58 (s, 1H), 10.52 (br s, 1H).

LCMS Rt=2.36 minutes MS m/z 317 [MH]+

PREPARATION 9

3-Pyridazin-4-yl-2'-(trifluoromethyl)biphenyl-4-ol

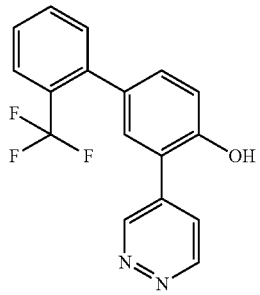 [SMILES: Oc1ccc(-c2ccccc2C(F)(F)F)cc1-c1ccnnc1]

To a solution of 4-chloro-2-pyridizin-4-ylphenol (Preparation 7, 1.5 g, 7.26 mmol) and 2-trifluoromethylbenzene boronic acid (3.45 g, 18.1 mmol) in 1,4-dioxane (20 mL) was added a solution of potassium carbonate (2.0 g, 14.5 mmol) in water (4 mL). The reaction mixture was degassed, then bis (tri-t-butylphosphine) palladium (0) (371 mg, 0.726 mmol) added and the reaction mixture heated to 100° C. for 18 hours. Further 2-trifluoromethylbenzene boronic acid (2.76 g, 14.5 mmol), potassium carbonate (2.0 g, 14.5 mmol) and bis(tri-t-butylphosphine)palladium (0) (371 mg, 0.726 mmol) were added and the mixture heated for a further 24 hours at 115° C. The reaction still did not reach completion, therefore tetrakistriphenylphosphine palladium (0) (200 mg, 0.173 mmol) was added. As no further progression of the reaction was observed the mixture was diluted with a 2M aqueous solution of hydrogen chloride and extracted with ethyl acetate. The organic layer was separated and dried over anhydrous magnesium sulfate, filtered and concentrated in vacuo. The residue was purified by silica gel column chromatography (0%-100% ethyl acetate in dichloromethane gradient elution) to afford the title compound as a solid (466 mg, 20%).

¹HNMR (CDCl₃): δ 7.25 (d, 1H), 7.31-7.38 (m, 3H), 7.41-48 (m, 1H), 7.52-7.60 (m, 1H), 7.75 (d, 1H), 7.90-7.95 (m, 1H), 9.10-9.18 (m, 1H), 9.68 (s, 1H)

LCMS Rt=2.37 minutes MS m/z 317 [MH]+

PREPARATION 10

3-Chloro-4-fluoro-N-(pyridazin-3-yl)benzenesulfonamide

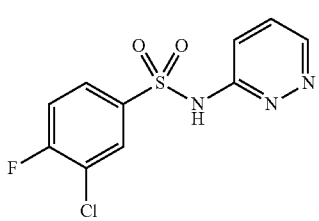 [SMILES: O=S(=O)(Nc1cccnn1)c1ccc(F)c(Cl)c1]

To a solution of pyridazin-3-amine (5.0 g, 52.63 mmol) in anhydrous acetonitrile (250 mL) was added 3-chloro-4-fluorobenzenesulfonyl chloride (12.05 g, 52.63 mmol) followed by 1,4-diazabicyclo[2,2,2]octane (5.9 g, 52.63 mmol). The reaction was stirred at room temperature for 18 hours. A solid was observed which was collected by filtration and washed with acetonitrile. The filtrate was concentrated in vacuo and the resulting residue purified by silica gel column chromatography (0%-10% methanol in chloroform gradient elution) to afford the title compound (5.3 g, 35%)

¹HNMR (d₆-DMSO): δ 7.58 (m, 1H), 7.74 (m, 1H), 7.85 (m, 1H), 7.93 (m, 1H), 8.02 (m, 1H), 8.35 (br m, 1H), 14.62 (br, s 1H).

PREPARATION 11

3-Chloro-4-fluoro-N-(methoxymethyl)-N-(pyridazin-3-yl)benzenesulfonamide and 3-chloro-4-fluoro-N-[(3E)-2-(methoxymethyl)pyridazin-3(2H)-ylidene]benzenesulfonamide

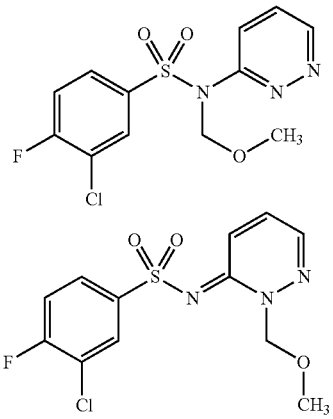

To 3-chloro-4-fluoro-N-(pyridazin-3-yl)benzenesulfonamide (Preparation 10, 850 mg, 3.0 mmol) in dichloromethane (20 mL) at 0° C. was added N,N-diisopropylethylamine (0.77 mL, 4.4 mmol) and chloromethyl methyl ether (0.25 mL, 3.2 mmol). The reaction mixture was stirred at room temperature for 3 hours. The mixture was diluted with ethyl acetate, and washed sequentially with a 1N aqueous solution of sodium hydroxide, water and brine. The organics were dried over anhydrous anhydrous sodium sulfate, filtered and concentrated in vacuo to afford the title compounds as a brown foam (910 mg, 91%). The product was isolated as a mixture of regioisomers that were used without separation in the next step.

LCMS Rt=1.26 minutes and 1.52 minutes MS m/z 332 [MH]+

PREPARATION 12

N-(2,4-dimethoxybenzyl)pyrimidin-2-amine

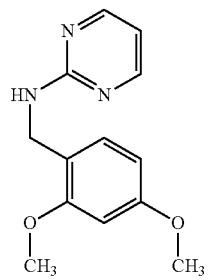

A mixture of 2-chloropyrimidine (1.37 g, 12 mmol), 2,4-dimethoxybenzylamine (2.61 g, 15.6 mmol) and triethylamine (2.51 mL, 18 mmol) in ethanol (8 mL) was heated in a Biotage Initiator™ microwave at 120° C. for 15 minutes. The reaction mixture was diluted with water and extracted with dichloromethane (×3). The combined organic layers were washed with brine, dried over anhydrous magnesium sulfate, filtered and concentrated in vacuo. The residue was purified by silica gel column chromatography (20-50% ethyl acetate in heptane gradient elution) to afford the title compound as a white solid (2.14 g, 72%).

$^1$HNMR (CD$_3$OD): δ 3.76 (s, 3H), 3.83 (s, 3H), 4.47 (s, 2H), 6.42 (m, 1H), 6.52 (m, 1H), 6.58 (m, 1H), 7.14 (m, 1H), 8.24 (m, 2H)

PREPARATION 13

5-Chloro-N-(2,4-dimethoxybenzyl)-2,4-difluoro-N-pyrimidin-2-yl-benzenesulfonamide

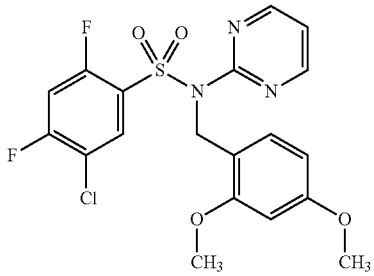 [SMILES: COc1ccc(CN(c2ncccn2)S(=O)(=O)c2cc(Cl)c(F)cc2F)c(OC)c1]

A solution of (2,4-dimethoxybenzyl)-pyrimidin-2-yl-amine (Preparation 12, 736 mg, 3 mmol) in anhydrous tetrahydrofuran (20 mL) was cooled to −78° C. before the addition of a 1M solution of lithium bis(trimethylsilyl)amide in tetrahydrofuran (3.30 mL, 3.30 mmol). The reaction was allowed to warm to 0° C. for 30 minutes before cooling again to −78° C. The resulting solution was added to a solution of 3-chloro-4,6-difluorobenzenesulfonyl chloride (890 mg, 3.6 mmol) in tetrahydrofuran (10 mL) at −78° C. After 30 minutes at this temperature the reaction was warmed to room temperature and stirred for 24 hours. The reaction was quenched by the addition of saturated aqueous ammonium chloride solution and extracted into ethyl acetate. The organic layer was washed with brine, dried over anhydrous magnesium sulfate and concentrated in vacuo. The residue was purified by silica gel column chromatography (50-100% dichloromethane in heptane gradient elution) to afford the title compound as a white solid (260 mg, 19%).

$^1$HNMR (d$_6$-DMSO): δ 3.73 (s, 3H), 3.75 (s, 3H), 5.27 (s, 2H), 6.47 (m, 1H), 6.57 (m, 1H), 7.01 (m, 1H), 7.18 (m, 1H), 7.82 (m, 1H), 8.10 (m, 1H), 8.57 (m, 2H).

LCMS Rt=1.77 minutes MS m/z 456 [MH]+

PREPARATION 14

N-(2,4-Dimethoxybenzyl)-1,3,4-thiadiazol-2-amine

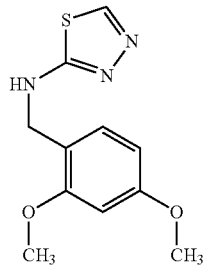

2,4-Dimethoxybenzaldehyde (771 g, 4.64 mol) was added to a suspension of 2-amino-1,3,4-thiadiazole (391.2 g, 3.87 mol) in xylene (5.87 L) and heated to reflux for 18 hours. Dean-Stark apparatus was used to remove the water. The reaction mixture was cooled to 5° C. and diluted with 2-methyltetrahydrofuran (2.93 L). Sodium tetrahydroborate (73.17 g, 1.93 mol) was added as a single portion. Methanol (782.8 mL) was then added slowly over 30 minutes, maintaining the temperature below 15° C. After a further 30 minutes, water (1 L) was added followed by saturated aqueous sodium bicarbonate solution (1 L) and the mixture stirred at ambient temperature for 18 hours. The biphasic mixture was diluted with 2-methyltetrahydrofuran and heated to 43° C. to aid dissolution. The layers were separated and the organic layer washed with water (3 L) before concentrating in vacuo. The resulting solid was slurried in heptanes (2.5 L), homogenised, filtered, washed with tert-butylmethyl ether and dried to afford the title compound (715 g).

$^1$HNMR (d$_6$-DMSO): δ 3.75 (s, 3H), 3.80 (s, 3H), 4.37 (d, 2H), 6.49 (m, 1H), 6.58 (s, 1H), 7.19 (d, 1H), 7.97 (m, 1H), 8.59 (s, 1H).

LCMS Rt=1.36 minutes MS m/z 252 [MNa]+

PREPARATION 15

3-Cyano-N-(2,4-dimethoxybenzyl)-4-fluoro-N-1,3,4-thiadiazol-2-ylbenzenesulfonamide

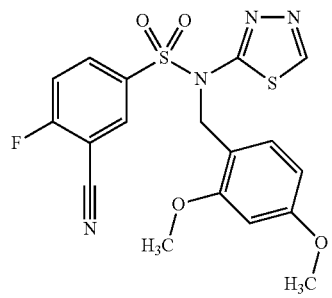 [SMILES: COc1ccc(CN(c2nncs2)S(=O)(=O)c2ccc(F)c(C#N)c2)c(OC)c1]

N-(2,4-Dimethoxybenzyl)-1,3,4-thiadiazol-2-amine (Preparation 14, 5.72 g, 22.8 mmol) was dissolved in 2-methyltetrahydrofuran (100 mL) and the suspension cooled to −50° C. A 1M solution of lithium bis(trimethylsilyl)amide in tetrahydrofuran (34.1 mL, 34.1 mmol) was added slowly over 15 minutes. This suspension was stirred at −50° C. for 5 minutes, warmed to 10° C. then cooled again to −78° C. A solution of 3-cyano-4-fluorobenzene-1-sulfonyl chloride (10 g, 45.5 mmol) in tetrahydrofuran (20 mL) was then added drop wise. The pale orange solution was allowed to warmed to 20° C. for 18 hours. The reaction was quenched with an aqueous solution of saturated ammonium chloride (50 mL) and stirred vigorously for 5 minutes. Ethyl acetate (100 mL) was added and the layers separated. The organic layer was washed with water (100 mL) and concentrated in vacuo to give an orange gum. The gum was dissolved in ethyl acetate and eluted through a silica plug before being purified by silica gel column chromatography (ISCO™, 50% ethyl acetate in heptane) to afford the title compound as a pale yellow oil (2.96 g).

$^1$HNMR (CDCl$_3$): δ 3.59 (s, 3H), 3.78 (s, 3H), 5.14 (s, 2H), 6.24 (s, 1H), 6.35 (m, 1H), 7.14 (m, 1H), 7.25 (m, 1H), 7.85 (m, 1H), 8.04 (m, 1H), 8.88 (s, 1H).

LCMS Rt=3.21 minutes MS m/z 435 [MH]+

PREPARATION 16

5-Chloro-N-(2,4-dimethoxybenzyl)-2,4-difluoro-N-1,3,4-thiadiazol-2-ylbenzenesulfonamide

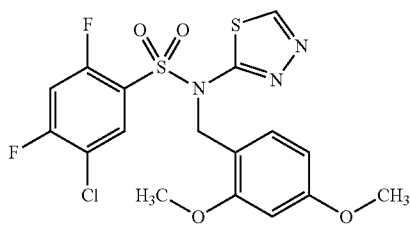 [SMILES: COc1ccc(CN(c2nncs2)S(=O)(=O)c2cc(Cl)c(F)cc2F)c(OC)c1]

N-(2,4-Dimethoxybenzyl)-1,3,4-thiadiazol-2-amine (Preparation 14, 203.4 g, 0.809 mol) was dissolved in 2-methyltetrahydrofuran (1.63 L) and the yellow suspension cooled to between −38° C. and −45° C. A 1M solution of lithium bis(trimethylsilyl)amide in tetrahydrofuran (890 mL, 0.890 mol) was added slowly over 15 minutes keeping the temperature between −38° C. and −45° C. to give an orange suspension. This orange suspension was stirred at −38° C. to −45° C. for 45 minutes and then a solution of 5-chloro-2,4-difluorobenzenesulfonyl chloride, (200 g, 0.809 mol) in 2-methyltetrahydrofuran (407 mL) added slowly over 20 minutes keeping the temperature between −38° C. and −45° C. The mixture was warmed to 15° C. over 1 hour. The reaction was quenched with a solution of ammonium chloride (203.4 g, 3.80 mol) in water (1.02 L) and stirred vigorously for 5 minutes. The layers were separated and the organic layer washed with water (813.6 mL) and concentrated in vacuo to give an orange solid which was triturated with isopropyl acetate (1.22 L) to afford the title compound as a yellow-orange solid (218.6 g).

$^1$HNMR (CDCl$_3$): δ 3.71 (s, 3H), 3.78 (s, 3H), 5.35 (m, 2H), 6.26 (m, 1H), 6.38 (m, 1H), 6.99 (m, 1H), 7.27 (m, 1H), 7.83 (m, 1H), 8.87 (m, 1H).

LCMS Rt=1.76 minutes MS m/z 484 [MNa]+

PREPARATION 17

3-Chloro-N-(2,4-dimethoxybenzyl)-4-fluoro-N-1,3,4-thiadiazol-2-ylbenzenesulfonamide

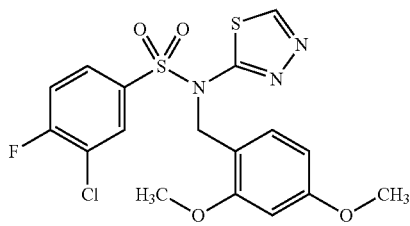 [SMILES: COc1ccc(CN(c2nncs2)S(=O)(=O)c2ccc(F)c(Cl)c2)c(OC)c1]

The title compound was prepared according to the procedure used in Preparation 16, using 3-chloro-4-fluorobenzene-1-sulfonyl chloride (0.91 g) to obtain the title compound as a white solid (1.3 g).

LCMS Rt=1.70 minutes MS m/z 466 [MNa]+

PREPARATION 18

N-(2,4-dimethoxybenzyl)-1,2,4-thiadiazol-5-amine

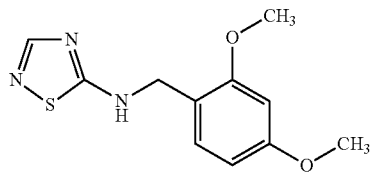 [SMILES: COc1ccc(CNc2ncns2)c(OC)c1]

A mixture of 5-amino-1,2,4-thiadiazole (1 g, 9.89 mmol) and 2,4-dimethoxybenzaldehyde (1.81 g, 10.9 mmol) in toluene (30 mL) was refluxed under Dean-Stark conditions for 2 hours. The reaction mixture was evaporated and the residue taken up in methanol (25 mL), sodium borohydride (600 mg, 15.9 mmol) was added carefully in small portions (vigorous effervescence after each addition), and the reaction was left to stir for 18 hours at ambient temperature. A 2M aqueous solution of hydrogen chloride (1 mL) was added followed by a 2M aqueous solution of sodium hydroxide (10 mL). The bulk of the methanol was evaporated, water (20 mL) was added and the mixture extracted with ethyl acetate (2×30 mL). The combined organic phase was washed with brine (20 mL), dried, and concentrated in vacuo. The residue was purified by silica gel column chromatography (ISCO™ column 120 g; 25-60% ethyl acetate in heptane gradient elution) to furnish a semi-solid residue that was re-evaporated from heptane. tert-Butylmethyl ether (2-3 mL) was added, followed by heptane (2-3 mL). The resulting solid was collected by filtration, washed with heptane and dried to afford the title compound (1.22 g).

$^1$HNMR (d$_6$-DMSO): δ 3.73 (s, 3H), 3.78 (s, 3H), 4.36 (d, 2H), 6.47 (dd, 1H), 6.56 (d, 1H), 7.15 (d, 1H), 7.88 (s, 1H), 8.65 (br. s, 1H)

PREPARATION 19

3-Cyano-N-(2,4-dimethoxybenzyl)-4-fluoro-N-1,2,4-thiadiazol-5-ylbenzenesulfonamide

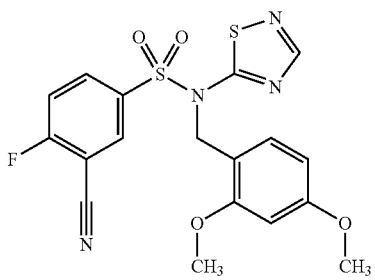 [SMILES: COc1ccc(CN(c2ncns2)S(=O)(=O)c2ccc(F)c(C#N)c2)c(OC)c1]

N-(2,4-Dimethoxybenzyl)-1,2,4-thiadiazol-5-amine (Preparation 18, 42.8 g, 170 mmol) was dissolved in anhydrous tetrahydrofuran (600 mL) and stirred under a nitrogen atmosphere at −78° C. A 1M solution of lithium bis(trimethylsilyl)amide in tetrahydrofuran (238 mL, 238 mmol) was added drop wise over 30 minutes maintaining the temperature between −65° C. and −70° C. The reaction mixture was left at −78° C. for 5 minutes, then allowed to warm to −10° C. over 1.5 hours. Upon reaching −10° C., the brown reaction mixture was cooled to −78° C. again, and a solution of 3-cyano-4- fluorobenzene sulfonyl chloride (48.6 g, 221 mmol) in tetrahydrofuran (200 mL) was added drop wise over 30 minutes maintaining the temperature between −65° C. and −70° C. The brown solution was allowed to warm gradually to ambient temperature and stirred for 18 hours. The reaction mixture was diluted with ethyl acetate, washed with a saturated ammonium chloride solution, and extracted with further ethyl acetate. The combined organics were dried over anhydrous magnesium sulfate, filtered and concentrated in vacuo to afford a brown residue. The residue was purified by silica gel column chromatography (10%-30% ethyl acetate in heptane gradient elution) to afford the title compound as a white solid (52.3 g, 71%).

$^1$HNMR (CDCl$_3$): δ 3.60 (s, 3H), 3.79 (s, 3H), 5.32 (s, 2H), 6.22 (s, 1H), 6.32-6.48 (m, 1H), 7.05-7.09 (m, 1H), 7.18-7.24 (m, 1H), 7.70-7.73 (m, 1H), 7.92-7.99 (m, 1H), 8.22 (s, 1H).

LCMS Rt=3.47 minutes

PREPARATION 20

3-Cyano-N-(2,4-dimethoxybenzyl)-4-{[3-pyridazin-4-yl-3'-(trifluoromethyl)biphenyl-4-yl]oxy}-N-1,2,4-thiadiazol-5-ylbenzenesulfonamide

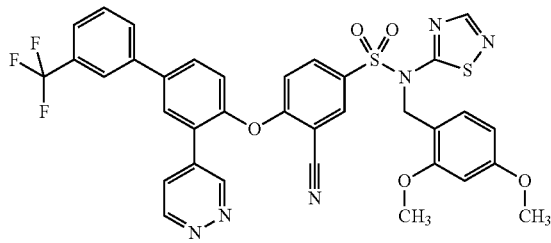 [SMILES: COc1ccc(CN(c2ncns2)S(=O)(=O)c2ccc(Oc3ccc(-c4cccc(C(F)(F)F)c4)cc3-c3ccnnc3)c(C#N)c2)c(OC)c1]

To a solution of 3-cyano-N-(2,4-dimethoxybenzyl)-4-fluoro-N-1,2,4-thiadiazol-5-ylbenzenesulfonamide (Preparation 19, 206 mg, 0.474 mmol) and 3-pyridazin-4-yl-3'-(trifluoromethyl)biphenyl-4-ol (Preparation 3, 150 mg, 0.474 mmol) in dimethylsulfoxide (5 mL) was added potassium carbonate (196 mg, 1.42 mmol). The reaction mixture was stirred at room temperature for 18 hours. The reaction mixture was quenched with a 1M aqueous solution of sodium hydroxide whereupon a fine precipitate formed. The mixture was extracted with ethyl acetate. The organic layer was separated, dried over anhydrous magnesium sulfate, filtered and concentrated in vacuo to afford the title compound as an oil (380 mg, 111%, contains residual dimethylsulfoxide). The material was used without purification in the next step.

$^1$HNMR (CDCl$_3$): δ 3.70-3.80 (m, 6H), 5.25 (m, 2H), 6.30 (m, 2H), 6.65 (d, 1H), 7.0 (m, 2H), 7.55-7.90 (m, 9H), 8.15 (s, 1H), 9.25 (m, 1H), 9.35 (m, 1H).

PREPARATION 21

3-Cyano-N-(2,4-dimethoxybenzyl)-4-{[3-pyridazin-4-yl-2'-(trifluoromethyl)biphenyl-4-yl]oxy}-N-1,2,4-thiadiazol-5-ylbenzenesulfonamide

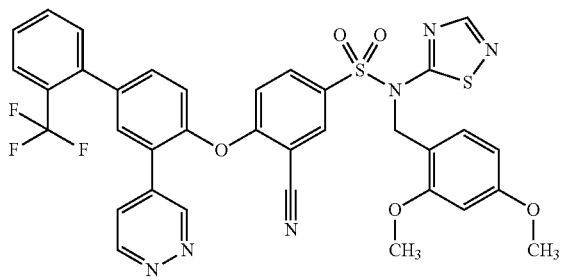 [SMILES: COc1ccc(CN(c2ncns2)S(=O)(=O)c2ccc(Oc3ccc(-c4ccccc4C(F)(F)F)cc3-c3ccnnc3)c(C#N)c2)c(OC)c1]

To a solution of 3-cyano-N-(2,4-dimethoxybenzyl)-4-fluoro-N-1,2,4-thiadiazol-5-ylbenzenesulfonamide (Preparation 19, 206 mg, 0.474 mmol) and 3-pyridazin-4-yl-2'-(trifluoromethyl)biphenyl-4-ol (Preparation 9, 150 mg, 0.474 mmol) in dimethylsulfoxide (5 mL) was added potassium carbonate (196 mg, 1.42 mmol). The reaction mixture was stirred at room temperature for 18 hours. The reaction mixture was quenched with a 1M aqueous solution of sodium hydroxide whereupon a precipitate formed. The precipitate was collected by filtration and washed with water to afford the title compound as a solid (400 mg, 115%, contains residual dimethylsulfoxide). The material was used without purification in the next step.

$^1$HNMR (CDCl$_3$): δ 3.42 (s, 3H), 3.72 (s, 3H), 5.22 (s, 2H), 6.03 (s, 1H), 6.23 (d, 1H), 6.62 (d, 1H), 7.00 (d, 1H), 7.10 (d, 1H), 7.31 (d, 1H), 7.42-7.53 (m, 3H), 7.55 (t, 1H), 7.61 (s, 1H), 7.63-7.78 (m, 3H), 8.10 (s, 1H), 9.27 (d, 1H), 9.30 (s, 1H).

LCMS Rt=3.97 minutes MS m/z 731 [MH]+

PREPARATION 22

5-Chloro-N-(2,4-dimethoxybenzyl)-2-fluoro-4-{[3-pyridazin-4-yl-3'-(trifluoromethyl)biphenyl-4-yl]oxy}-N-1,3,4-thiadiazol-2-ylbenzenesulfonamide

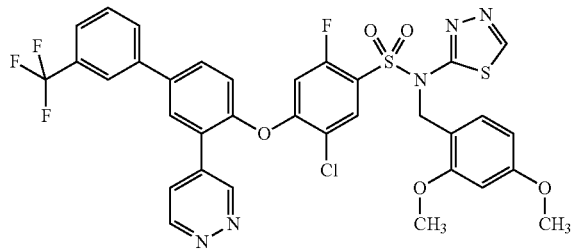 [SMILES: COc1ccc(CN(c2nncs2)S(=O)(=O)c2cc(Cl)c(Oc3ccc(-c4cccc(C(F)(F)F)c4)cc3-c3ccnnc3)cc2F)c(OC)c1]

To a solution of 5-chloro-N-(2,4-dimethoxybenzyl)-2,4-difluoro-N-1,3,4-thiadiazol-2-ylbenzenesulfonamide (Preparation 16, 219 mg, 0.474 mmol) and 3-pyridazin-4-yl-3'-(trifluoromethyl)biphenyl-4-ol (Preparation 3, 150 mg, 0.474 mmol) in dimethylsulfoxide (5 mL) was added potassium carbonate (196 mg, 1.42 mmol). The reaction mixture was stirred at room temperature for 18 hours. The reaction mixture was quenched with a 1M aqueous solution of sodium hydroxide whereupon a precipitate formed. The solid was collected by filtration, washed with water and freeze dried to afford the title compound as a solid (266 mg, 74%).

$^1$HNMR (CD$_3$OD): δ 3.58 (s, 3H), 3.70 (s, 3H), 5.21 (s, 2H), 6.17 (s, 1H), 6.37 (dd, 1H), 6.83 (d, 1H), 7.17 (d, 1H), 7.28 (d, 1H), 7.64-7.71 (m, 3H), 7.91 (d, 1H), 7.97-8.02 (m, 4H), 9.08 (s, 1H), 9.23 (d, 1H), 9.50 (s, 1H).

LCMS Rt=3.55 minutes MS m/z 758 [MH]+

PREPARATION 23

5-Chloro-N-(2,4-dimethoxybenzyl)-2-fluoro-4-{[3-Pyridazin-4-yl-2'-(trifluoromethyl)biphenyl-4-yl]oxy}-N-1,3,4-thiadiazol-2-ylbenzenesulfonamide

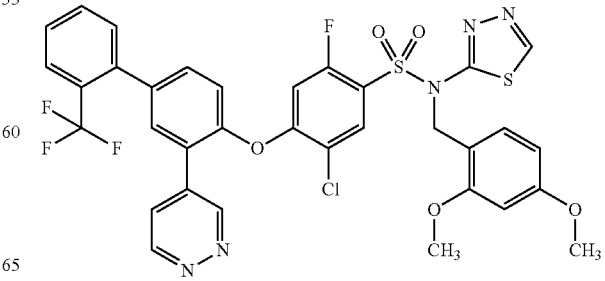

Prepared according to Preparation 22 using 5-chloro-N-(2,4-dimethoxybenzyl)-2,4-difluoro-N-1,3,4-thiadiazol-2-yl-benzenesulfonamide (Preparation 16, 291 mg, 0.63 mmol) and 3-pyridazin-4-yl-2'-(trifluoromethyl)biphenyl-4-ol (Preparation 9, 200 mg, 0.63 mmol) to afford the title compound as a solid (339 mg, 71%).

$^1$HNMR (CDCl$_3$): δ 3.57 (s, 3H), 3.64 (s, 3H), 5.21 (s, 2H), 6.17 (s, 1H), 6.25 (d, 1H), 6.42 (d, 1H), 7.03 (d, 1H), 7.17 (d, 1H), 7.28-7.31 (m, 2H), 7.41-7.50 (m, 3H), 7.55 (t, 1H), 7.60-7.63 (m, 1H), 7.72 (t, 1H), 8.78 (s, 1H), 9.17 (d, 1H), 9.38 (s, 1H).

LCMS Rt=4.13 minutes MS m/z 758 [MH]+

PREPARATION 24

5-Chloro-N-(2,4-dimethoxybenzyl)-2-fluoro-4-{[3-Pyridazin-4-yl-4'-(trifluoromethyl)biphenyl-4-yl]oxy}-N-1,3,4-thiadiazol-2-ylbenzenesulfonamide

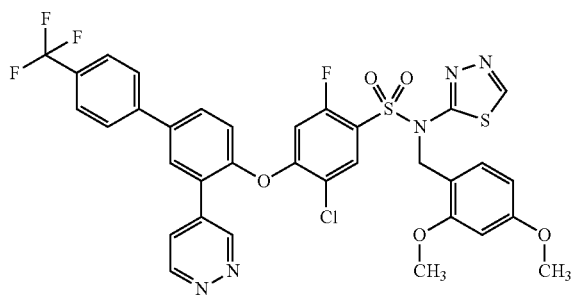 [SMILES: COc1ccc(CN(c2nncs2)S(=O)(=O)c2cc(Cl)c(Oc3ccc(-c4ccc(C(F)(F)F)cc4)cc3-c3ccnnc3)cc2F)c(OC)c1]

Prepared according to Preparation 22 using 5-chloro-N-(2,4-dimethoxybenzyl)-2,4-difluoro-N-1,3,4-thiadiazol-2-yl-benzenesulfonamide (Preparation 16, 175 mg, 0.379 mmol) and 3-pyridazin-4-yl-4'-(trifluoromethyl)biphenyl-4-ol (Preparation 8, 120 mg, 0.379 mmol) to afford the title compound as a solid (213 mg, 74%).

$^1$HNMR (CD$_3$OD): δ 3.59 (s, 3H), 3.73 (s, 3H), 5.25 (s, 2H), 6.18 (s, 1H), 6.37 (d, 1H), 6.84 (d, 1H), 7.17 (d, 1H), 7.30 (d, 1H), 7.66-8.01 (m, 8H), 9.10 (s, 1H), 9.23 (d, 1H), 9.50 (s, 1H).

LCMS Rt=3.79 minutes MS m/z 758 [MH]+

PREPARATION 25

5-Chloro-N-(2,4-dimethoxybenzyl)-2-fluoro-4-[(3-pyridazin-4-ylbiphenyl-4-yl)oxy]-N-1,3,4-thiadiazol-2-ylbenzenesulfonamide

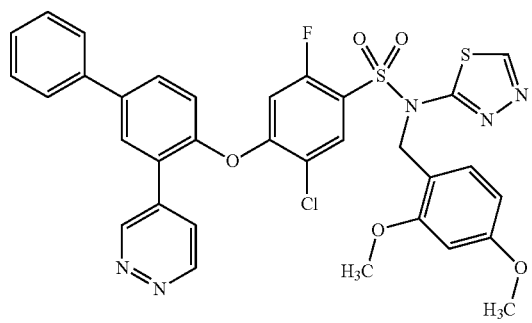 [SMILES: COc1ccc(CN(c2nncs2)S(=O)(=O)c2cc(Cl)c(Oc3ccc(-c4ccccc4)cc3-c3ccnnc3)cc2F)c(OC)c1]

3-Pyridazin-4-ylbiphenyl-4-ol (Preparation 4, 50 mg, 0.2 mmol) and 5-chloro-N-(2,4-dimethoxybenzyl)-2,4-difluoro-N-1,3,4-thiadiazol-2-ylbenzenesulfonamide (Preparation 16, 93 mg, 0.2 mmol) were dissolved in dimethylsulfoxide (2 mL). Potassium carbonate (83 mg, 0.6 mmol) was added and the reaction stirred at room temperature for 16 hours. The crude material was partitioned between ethyl acetate (20 mL) and water (20 mL), the organic layer separated, concentrated in vacuo and purified by silica gel column chromatography (ISCO™, 12 g silica, 0-100% ethyl acetate in heptane gradient elution). The appropriate fractions were combined and concentrated in vacuo to afford the title compound as a gum (100 mg, 72%).

$^1$HNMR (CDCl3): δ 3.66 (s, 3H) 3.73 (s, 3H) 5.28 (s, 2H) 6.24 (m, 1H), 6.35 (m, 1H), 6.51 (d, 1H) 7.18 (d, 1H) 7.22 (d, 1H) 7.45 (m, 4H), 7.60 (m, 2H) 7.78 (m, 3H) 8.81 (s, 1H) 9.23 (m, 1H), 9.45 (m, 1H)

LCMS Rt=1.82 minutes MS m/z 690 [MH]+

PREPARATION 26

3-Cyano-N-(2,4-dimethoxybenzyl)-4-{[3-pyridazin-4-yl-4'-(trifluoromethyl)biphenyl-4-yl]oxy}-N-1,2,4-thiadiazol-5-ylbenzenesulfonamide

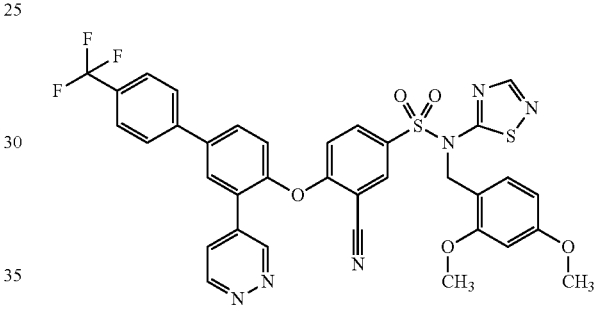

Prepared according to Preparation 22 using 3-cyano-N-(2,4-dimethoxybenzyl)-4-fluoro-N-1,2,4-thiadiazol-5-ylbenzenesulfonamide (Preparation 19, 165 mg, 0.379 mmol) and 3-Pyridazin-4-yl-4'-(trifluoromethyl)biphenyl-4-ol (Preparation 8, 120 mg, 0.379 mmol) to afford the title compound as a solid (219 mg, 79%).

$^1$HNMR (d$_6$-DMSO): δ 3.57 (s, 3H), 3.70 (s, 3H), 5.19 (s, 2H), 6.37 (s, 1H), 6.41 (d, 1H), 6.99 (d, 1H), 7.09 (d, 1H), 7.53 (d, 1H), 7.84 (m, 2H), 7.87-7.91 (m, 1H), 7.97-8.08 (m, 4H), 8.18 (d, 2H), 8.40 (s, 1H), 9.25 (d, 1H), 9.44 (s, 1H).

LCMS Rt=3.76 minutes MS m/z 731 [MH]+

PREPARATION 27

5-[4-(Benzyloxy)biphenyl-3-yl]-1-methyl-1H-pyrazole

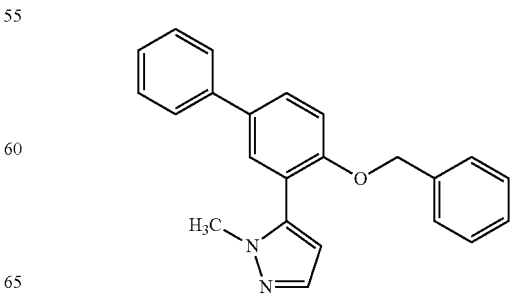

Solution A: A stirred mixture of 4-(benzyloxy)-3-bromo-biphenyl (7.5 g, 22.1 mmol, J. Med. Chem. 1988, 31, 1437-1445) and (1-methyl-1H-pyrazol-5-yl)boronic acid (2.8 g, 22.1 mmol) in 1,4-dioxane (59 mL) was purged with argon for 20 minutes. Tris(dibenzylideneacetone)dipalladium (0) (810 mg, 0.88 mmol) and tricyclohexyl phosphine (495 mg, 1.8 mmol) were added.

Solution B: In a separate flask dipotassium phosphate (9.4 g, 44.2 mmol) was dissolved in water (29 mL) and was also purged with argon for 20 minutes.

Solution B was added to solution A and the resulting mixture was heated at 100° C. for 18 hours. After cooling to room temperature, the mixture was filtered through a pad of silica gel, and washed with ethyl acetate. The filtrate was concentrated in vacuo, diluted with ethyl acetate, washed with water and brine, dried over anhydrous magnesium sulfate, filtered and concentrated in vacuo. The crude residue was purified by silica gel column chromatography (20% $Et_2O$ in hexane) to afford the title compound (5.0 g, 67%).

$^1$HNMR ($d_6$-DMSO): δ 3.67 (s, 3H), 5.21 (s, 2H), 6.35 (s, 1H), 7.31-7.46 (m, 10H), 7.55 (s, 1H), 7.67 (d, 2H), 7.73-7.76 (m, 1H)

PREPARATION 28

3-(1-Methyl-1H-pyrazol-5-yl)biphenyl-4-ol

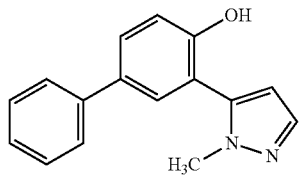

To a stirred solution of 5-[4-(benzyloxy)biphenyl-3-yl]-1-methyl-1H-pyrazole (Preparation 27, 3.0 g, 8.8 mmol) in methanol (26 mL) was added palladium on carbon (300 mg). The mixture was stirred under hydrogen gas for 16 hours. The reaction mixture was filtered through Celite™, and washed with tetrahydrofuran. The resulting filtrate was concentrated in vacuo. The residue was dissolved in ethyl acetate (26 mL) and degassed with argon prior to addition of palladium on carbon (300 mg). The reaction mixture was stirred under hydrogen gas for 6 hours. The reaction mixture was filtered through Celite™ and the filtrate concentrated in vacuo to give a solid. The solid was triturated with hexane to afford the title compound as a white solid (1.7 g, 77%).

$^1$HNMR ($d_6$-DMSO): δ 3.71 (s, 3H), 6.30 (d, 1H), 7.06 (d, 1H), 7.29 (t, 1H), 7.39-7.44 (m, 4H), 7.57-7.62 (m, 3H), 10.13 (br s, 1H)

LCMS Rt=3.23 minutes MS m/z 251 [MH]+

PREPARATION 29

5-[4-(2-Fluoro-4-nitrophenoxy)biphenyl-3-yl]-1-methyl-1H-pyrazole

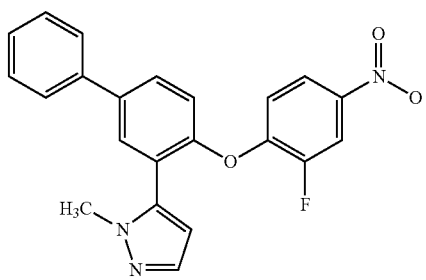

To a stirred solution of 3-(1-Methyl-1H-pyrazol-5-yl)biphenyl-4-ol (Preparation 28, 600 mg, 2.39 mmol) in N,N-dimethylformamide (6 mL) at 0° C. was added potassium carbonate (332 mg, 2.39 mmol). The mixture was stirred for 30 minutes at 0° C. 3,4-Difluoronitrobenzene (318 mg, 1.99 mmol) was added drop wise to the reaction mixture and allowed to stir at room temperature for 16 hours. The reaction mixture was diluted with ethyl acetate (20 mL). The organic layer was washed sequentially with water (3×10 mL) and brine (1×10 ml), then dried over anhydrous sodium sulfate, filtered and concentrated in vacuo to afford the title compound (870 mg, quantitative). This material was used without purification in the next step.

$^1$HNMR ($d_6$-DMSO): δ 3.78 (s, 3H), 6.32 (d, 1H), 7.13 (t, 1H), 7.38-7.42 (m, 3H), 7.49 (t, 2H), 7.76 (d, 2H), 7.82 (d, 1H), 7.88 (dd, 1H), 8.01 (d, 1H), 8.27 (dd, 1H).

PREPARATION 30

3-Fluoro-4-{[3-(1-methyl-1H-pyrazol-5-yl)biphenyl-4-yl]oxy}aniline

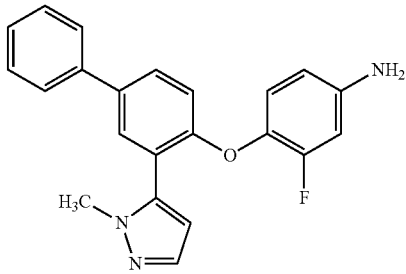 [SMILES: Cn1nccc1-c1cc(-c2ccccc2)ccc1Oc1ccc(N)cc1F]

5-[4-(2-Fluoro-4-nitrophenoxy)biphenyl-3-yl]-1-methyl-1H-pyrazole (Preparation 29, 870 mg, 2.33 mmol) was dissolved in ethanol (8 mL) and water (2 mL). Iron powder (624 mg, 11.17 mmol) and $CaCl_2$ (248 mg, 2.33 mmol) were then added and the reaction mixture was refluxed for 3 hours. After filtration through Celite™, the filtrate was concentrated in vacuo. The residue was partitioned between dichloromethane and water. The organic layer was separated, washed with brine, dried over anhydrous sodium sulfate, filtered and concentrated in vacuo. The residue was purified by silica gel column chromatography (100-200 mesh silica gel, 15% ethyl acetate in hexane) to afford the title compound (700 mg, 84%).

$^1$HNMR ($d_6$-DMSO): δ 3.79 (s, 3H), 5.40 (br s, 1H), 6.40 (dd, 1H), 6.43 (d, 1H), 6.50 (dd, 1H), 6.76 (d, 1H), 6.94 (t, 1H), 7.34 (t, 1H), 7.44 (t, 2H), 7.49 (d, 1H), 7.61-7.68 (m, 4H).

PREPARATION 31

3-Fluoro-4-{[3-(1-methyl-1H-pyrazol-5-yl)biphenyl-4-yl]oxy}benzenesulfonyl chloride

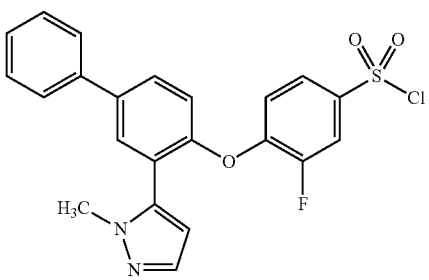 [SMILES: Cn1nccc1-c1cc(-c2ccccc2)ccc1Oc1ccc(S(=O)(=O)Cl)cc1F]

Solution A: To a stirred suspension of 3-fluoro-4-{[3-(1-methyl-1H-pyrazol-5-yl)biphenyl-4-yl]oxy}aniline (Preparation 30, 700 mg, 1.94 mmol) in a mixture of concentrated hydrogen chloride (1.75 mL) and acetic acid (1.75 mL) at 0° C. was added a solution of sodium nitrite (148 mg, 2.14 mmol) in water (0.87 mL) and the mixture stirred at 0° C. for 30 minutes.

Solution B: In another flask, acetic acid (3.5 mL) was saturated with sulfur dioxide at 0° C. followed by the addition of copper (II) chloride dihydrate (133 mg, 0.779 mmol) portion wise.

Solution A was added drop wise to solution B at 0° C. and stirred at room temperature for 14 hours. The reaction mixture was then diluted with water (10 mL) and extracted with ethyl acetate (3×20 mL). The combined organic layer was neutralized with saturated aqueous sodium hydrogen carbonate solution. The organic layer was separated, washed with brine, dried over anhydrous sodium sulfate, filtered and concentrated in vacuo. The residue was purified by silica gel column chromatography (100-200 mesh silica gel, 10% ethyl acetate in hexane) to afford the title compound (350 mg, 41%).

$^1$HNMR (d$_6$-DMSO): δ 3.80 (s, 3H), 6.41 (s, 1H), 7.02 (d, 1H), 7.09 (t, 1H), 7.35-7.48 (m, 6H), 7.70-7.76 (m, 4H)

PREPARATION 32

3-Cyano-4-fluoro-N-1,3-thiazol-2-ylbenzenesulfonamide

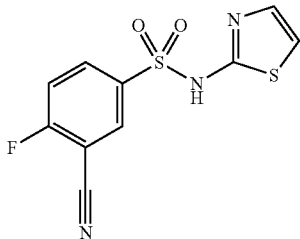 [SMILES: N#Cc1cc(S(=O)(=O)Nc2nccs2)ccc1F]

3-Cyano-4-fluorobenzenesulfonyl chloride (10 g, 45.53 mmol) was added portion wise to a solution of 2-aminothiazole (5 g, 50.13 mmol) in dichloromethane (50 mL) and pyridine (18.4 mL, 228 mmol) at 0° C. The reaction mixture was allowed to warm to room temperature. After 1 hour a precipitate was observed. The mixture was stirred for 18 hours at room temperature. The mixture was sonicated for 2.5 hours until the solid had dissolved, then left to stir at room temperature for 18 hours. The reaction mixture was then concentrated in vacuo and azeotropically dried with toluene (2×100 mL). The residue was diluted carefully with a 1M aqueous solution of hydrogen chloride and stirred for 1 hour at room temperature whereupon a precipitate formed. The brown solid was collected by filtration and triturated with dichloromethane to afford the title compound as a brown solid (7.8 g, 60%).

$^1$HNMR (d$_6$-DMSO): δ 6.90 (m, 1H), 7.30 (m, 1H), 7.65 (t, 1H), 8.15 (m, 1H), 8.30 (m, 1H), 12.90 (br s, 1H).

LCMS Rt=2.18 minutes MS m/z 284 [MH]+, 282 [MH]−

PREPARATION 33

3-Cyano-4-fluoro-N-[(4S,5R)-5-fluoro-4-hydroxy-4,5-dihydro-1,3-thiazol-2-yl]benzenesulfonamide

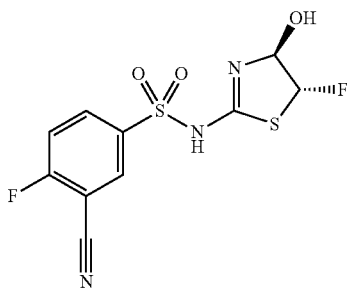 [SMILES: N#Cc1cc(S(=O)(=O)NC2=N[C@@H](O)[C@H](F)S2)ccc1F]

3-Cyano-4-fluoro-N-1,3-thiazol-2-ylbenzenesulfonamide (Preparation 32, 1.99 g, 7.02 mmol) and 1-chloromethyl-4-fluoro-1,4-diazoniabicyclo[2.2.2]octane bis(tetrafluoroborate) (3.12 g, 8.81 mmol) were dissolved in acetonitrile (25 mL) and water (1 mL) and heated to 45° C. under an atmosphere of nitrogen for 24 hours. A precipitate was observed which was collected by filtration to afford the title compound as a white solid which was used without purification in the next step (1.32 g, 59%).

$^1$HNMR (d$_6$-DMSO): δ 5.42 (m, 1H), 6.25-6.40 (d, 1H), 7.00 (br m, 1H), 7.75 (m, 1H), 8.15 (m, 1H), 8.30 (m, 1H), 10.50 (s, 1H).

LCMS Rt=1.16 minutes MS m/z 320 [MH]+, 318 [MH]−

PREPARATION 34

3-Cyano-4-fluoro-N-(5-fluoro-1,3-thiazol-2-yl)benzenesulfonamide

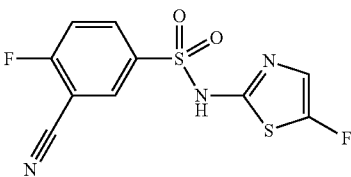 [SMILES: N#Cc1cc(S(=O)(=O)Nc2ncc(F)s2)ccc1F]

To a suspension of 3-cyano-4-fluoro-N-[(4S,5R)-5-fluoro-4-hydroxy-4,5-dihydro-1,3-thiazol-2-yl]benzenesulfonamide (Preparation 33, 1.42 g, 4.45 mmol) in dichloromethane (150 mL) was added triethylamine (6.20 mL, 44.5 mmol) and acetic anhydride (1.30 mL, 13.8 mL). The reaction mixture was stirred at room temperature under an atmosphere of nitrogen for 18 hours. The mixture was washed with a 2M aqueous solution of hydrogen chloride. The organics were separated, dried over anhydrous sodium sulfate, filtered and concentrated in vacuo. The resulting residue was triturated with dichloromethane to afford the title compound as a pale yellow solid (825 mg, 62%).

$^1$HNMR (d$_6$-DMSO): δ 7.40 (s, 1H), 7.70 (t, 1H), 8.15 (m, 1H), 8.30 (m, 1H)

LCMS Rt=1.22 minutes MS m/z 302 [MH]+, 300 [MH]−

PREPARATION 35 tert-Butyl 3-[(methylsulfonyl)oxy]azetidine-1-carboxylate

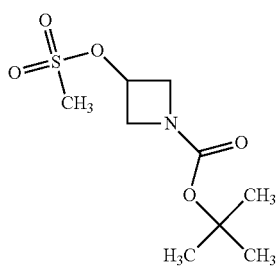 [SMILES: CC(C)(C)OC(=O)N1CC(OS(C)(=O)=O)C1]

A mixture of tert-butyl 3-hydroxyazetidine-1-carboxylate (4.98 g, 28.7 mmol) and triethylamine (4.82 mL, 62.3 mmol) in tetrahydrofuran (75 mL) was cooled to 0° C. using an ice bath. Methanesulfonyl chloride (2.46 mL, 31.8 mmol) in tetrahydrofuran (12.5 mL) was added slowly to the reaction. Once the addition was complete, the ice bath was removed and the reaction was stirred at room temperature for 4 hours. Water (100 mL) was added to the reaction, and the mixture extracted with ethyl acetate (2×150 mL). The combined organic phase was washed with brine (2×100 mL), dried over anhydrous sodium sulfate, filtered and concentrated in vacuo to afford the title compound as a pale yellow oil (7.11 g, 98%).

$^1$HNMR (CDCl$_3$): δ 1.45 (s, 9H), 3.07 (s, 3H), 4.08-4.12 (m, 2H), 4.26-4.30 (m, 2H), 5.18-5.23 (m, 1H).

LCMS Rt=2.53 minutes MS m/z 151.98 [M−Boc+H]$^+$.

PREPARATION 36 tert-Butyl 3-hydrazinoazetidine-1-carboxylate

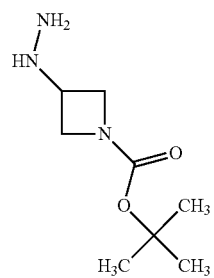

A suspension of tert-butyl 3-[(methylsulfonyl)oxy]azetidine-1-carboxylate (Preparation 35, 7.11 g, 28.3 mmol) in neat hydrazine monohydrate (13.7 mL, 283 mmol) was heated to 95° C. for 18 hours. The reaction was cooled to room temperature, then water (100 mL) was added and the mixture extracted with dichloromethane (5×100 mL). The combined organic phase was dried over anhydrous sodium sulfate, filtered and concentrated in vacuo to afford a the title compound as a clear oil (4.71 g, 89%). The compound was used without further purification in the next step.

$^1$HNMR (CDCl$_3$): δ 1.44 (s, 9H), 3.31 (br.s, 3H), 3.73-3.79 (m, 3H), 4.01-4.08 (m, 2H).

PREPARATION 37

1-[4-Hydroxy-4'-(trifluoromethyl)biphenyl-3-yl]ethanone

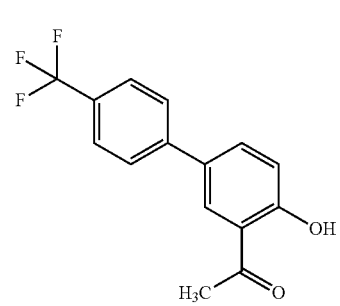

A mixture of 5-bromo-2-hydroxy acetophenone (1.00 g, 4.65 mmol), 4-(trifluoromethyl)phenylboronic acid (1.32 g, 6.97 mmol), potassium carbonate (1.30 g, 9.38 mmol), tetrakis(triphenylphosphine)palladium (0) (538 mg, 0.465 mmol) in 1,4-dioxane (30.0 mL) and water (18.0 mL) was heated to 60° C. for 18 hours under nitrogen. The reaction was allowed to cool to room temperature and concentrated in vacuo to afford a dark brown oil which was dissolved in ethyl acetate (50 mL) and filtered through Arbocel™. The Arbocel™ was washed with ethyl acetate (100 mL). The combined organics were washed sequentially with a 0.5M aqueous solution of hydrogen chloride (2×50 mL) and brine (2×100 mL), dried over anhydrous sodium sulfate, filtered and concentrated in vacuo to afford a brown oil (2.12 g). The oil was then purified by silica gel column chromatography (5%-10% ethyl acetate in heptane gradient elution) to afford the title compound as a yellow solid (795 mg, 61%).

$^1$HNMR (CDCl$_3$): δ 2.72 (s, 3H), 7.11 (d, 1H), 7.65 (d, 2H), 7.71-7.75 (m, 3H), 7.94 (d, 1H), 12.34 (s, 1H).

LCMS Rt=3.63 minutes MS m/z 279.45 [MH]$^-$.

PREPARATION 38

(2E)-3-(Dimethylamino)-1-[4-hydroxy-4'-(trifluoromethyl)biphenyl-3-yl]prop-2-en-1-one

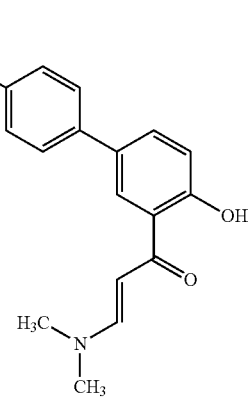

N,N-Dimethylformamide dimethyl acetal (0.76 mL, 5.701 mmol) was added to a solution of 1-[4-hydroxy-4'-(trifluoromethyl)biphenyl-3-yl]ethanone (Preparation 37, 795 mg, 2.84 mmol) in isopropyl alcohol (4.7 mL). The reaction mixture was heated for 18 hours at 45° C. under an atmosphere of nitrogen. After 1 hour, crystallization was observed therefore the stirring was stopped. After 18 hours at 45° C., a yellow precipitate had formed. The reaction mixture was allowed to cool, the yellow precipitate was collected by filtration and washed with cold isopropyl alcohol to afford the title compound as fine yellow needle crystals (669 mg, 70%).

$^1$HNMR (d$_6$-DMSO): δ 3.06 (s, 3H), 3.23 (s, 3H), 6.15 (d, 1H), 6.95 (d, 1H), 7.75 (dd, 1H), 7.78 (d, 2H), 7.91 (d, 2H), 7.97 (d, 1H), 8.21 (d, 1H)

LCMS Rt=3.57 minutes MS m/z 336.44 [MH]$^+$

PREPARATION 39

5-Chloro-N-(2,4-dimethoxybenzyl)-4-({3-[(2E)-3-(dimethylamino)prop-2-enoyl]-4'-(trifluoromethyl)biphenyl-4-yl}oxy)-2-fluoro-N-1,3,4-thiadiazol-2-ylbenzenesulfonamide

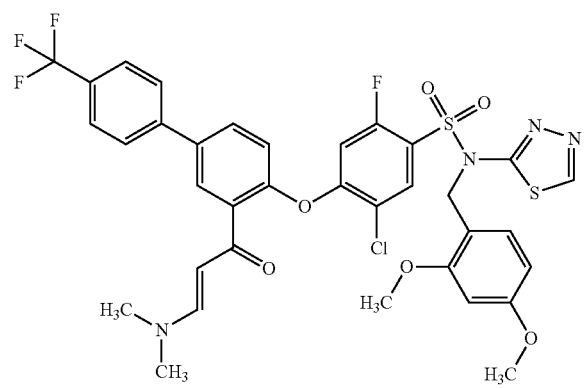 [SMILES: COc1ccc(CN(c2nncs2)S(=O)(=O)c2cc(Cl)c(Oc3ccc(-c4ccc(C(F)(F)F)cc4)cc3C(=O)/C=C/N(C)C)cc2F)c(OC)c1]

To a suspension of (2E)-3-(dimethylamino)-1-[4-hydroxy-4'-(trifluoromethyl)biphenyl-3-yl]prop-2-en-1-one (Preparation 38, 657 mg, 1.96 mmol) and 5-chloro-N-(2,4-dimethoxybenzyl)-2,4-difluoro-N-1,3,4-thiadiazol-2-ylbenzenesulfonamide (Preparation 16, 879 mg, 1.90 mmol) in dimethylsulfoxide (8.0 mL) was added potassium carbonate (656 mg, 4.75 mmol). The reaction mixture was stirred for 18 hours at room temperature under an atmosphere of nitrogen. The reaction was poured into a saturated solution of aqueous ammonium chloride (20 mL) and extracted with dichloromethane (3×40 mL). The combined organic phase was washed with brine (3×40 mL), dried over anhydrous sodium sulfate, filtered and concentrated in vacuo to afford a thick yellow-brown oil (1.56 g). The oil was purified by silica gel column chromatography (25%-75% ethyl acetate in heptane gradient elution) to afford the title compound as an off white foam (504 mg, 34%).

$^1$HNMR (d$_6$-DMSO): δ 2.78 (br.s, 3H), 3.06 (br.s, 3H), 3.68 (s, 3H), 3.73 (s, 3H), 5.13 (s, 2H), 5.37 (br.s, 1H), 6.45 (dd, 1H), 6.48 (d, 1H), 6.90 (br.d, 1H), 7.09 (d, 1H), 7.35 (d, 1H), 7.52 (br.s, 1H), 7.83-7.92 (m, 5H), 7.97 (d, 2H), 9.30 (s, 1H).

$^{19}$F NMR (d$_6$-DMSO): δ −60.78 (s).

LCMS Rt=4.31 minutes MS m/z 777.18 [MH]$^+$, 779.20 [MH]$^+$.

PREPARATION 40 tert-Butyl 3-{5-[4-(2-chloro-4-{[(2,4-dimethoxybenzyl)(1,3,4-thiadiazol-2-yl)amino]sulfonyl}-5-fluorophenoxy)-4'-(trifluoromethyl)biphenyl-3-yl]-1H-pyrazol-1-yl}azetidine-1-carboxylate

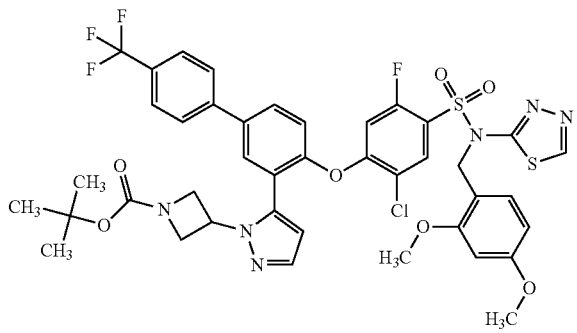 [SMILES: COc1ccc(CN(c2nncs2)S(=O)(=O)c2cc(Cl)c(Oc3ccc(-c4ccc(C(F)(F)F)cc4)cc3-c3ccnn3C3CN(C(=O)OC(C)(C)C)C3)cc2F)c(OC)c1]

5-Chloro-N-(2,4-dimethoxybenzyl)-4-({3-[(2E)-3-(dimethylamino)prop-2-enoyl]-4'-(trifluoromethyl)biphenyl-4-yl}oxy)-2-fluoro-N-1,3,4-thiadiazol-2-ylbenzenesulfonamide (Preparation 39, 504 mg, 0.648 mmol) in ethanol (10 mL) was slowly added a solution of tert-butyl 3-hydrazinoazetidine-1-carboxylate (Preparation 36, 536 mg, 2.86 mmol) in ethanol (10 mL) and acetic acid (0.23 mL) at 0° C. under nitrogen. The reaction was heated to 70° C. for 3 hours and then cooled to room temperature. The reaction mixture was neutralised to pH 7 with saturated aqueous sodium hydrogen carbonate solution (2 mL) and concentrated in vacuo to afford a yellow oil. The oil was partitioned between water (100 mL) and ethyl acetate (100 mL). The aqueous layer was extracted with ethyl acetate (2×100 mL). The combined organic layers were washed with brine (2×100 mL) dried over anhydrous sodium sulfate, filtered and concentrated in vacuo to afford a yellow oil (1.64 g). The oil was partially purified by silica gel column chromatography (0%-10% methanol in dichloromethane) to afford the title compound as a brown oil (419 mg) of 39% purity via LCMS. The compound was used without further purification in the next step.

LCMS Rt=4.08 minutes MS m/z 651.13 [M−Boc−DMB+H]$^+$, 653.14 [M−Boc−DMB+H]$^+$, 801.25 [M−Boc+H]$^+$, 803.24 [M−Boc+H]$^+$, 923.35 [MNa]$^+$, 925.33 [MNa]$^+$.

PREPARATION 41

4-{[3-(1-Azetidin-3-yl-1H-pyrazol-5-yl)-4'-(trifluoromethyl)biphenyl-4-yl]oxy}-5-chloro-2-fluoro-N-1,3,4-thiadiazol-2-ylbenzenesulfonamide

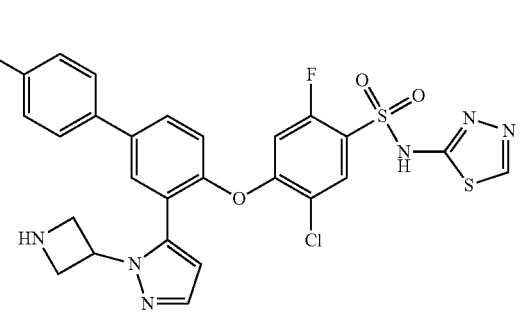

Trifluoroacetic acid (0.50 mL, 6.53 mmol) was added to a solution of tert-butyl 3-{5-[4-(2-chloro-4-{[(2,4-dimethoxybenzyl)(1,3,4-thiadiazol-2-yl)amino]sulfonyl}-5-fluorophenoxy)-4'-(trifluoromethyl)biphenyl-3-yl]-1H-pyrazol-1-yl}azetidine-1-carboxylate (Preparation 40, 419 mg, 0.465 mmol) in dichloromethane (20 mL). The mixture was then heated to 40° C. for 18 hours under an atmosphere of nitrogen. The reaction was then cooled to room temperature and concentrated in vacuo to afford a brown residue (385.4 mg). The residue was purified by preparative HPLC (Trilution method) to afford the title compound as a white solid (46.3 mg, 11% over 2 steps).

$^1$HNMR (d$_6$-DMSO): δ 4.26 (d, 4H), 5.27 (t, 1H), 6.49 (s, 1H), 7.08 (d, 1H), 7.19 (d, 1H), 7.73 (d, 1H), 7.77 (d, 1H), 7.80-7.83 (m, 3H), 7.89 (dd, 1H), 7.94, (d, 2H), 8.58 (s, 1H)

LCMS Rt=2.44 minutes MS m/z 651.05 [MH]$^+$, 653.03 [MH]$^+$.

PREPARATION 42

1-[4-Hydroxy-2'-(trifluoromethyl)biphenyl-3-yl]ethanone

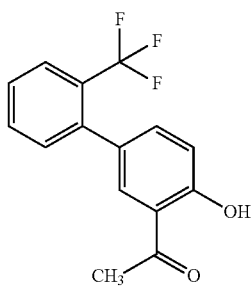 [SMILES: CC(=O)c1cc(-c2ccccc2C(F)(F)F)ccc1O]

A mixture of 5-bromo-2-hydroxy acetophenone (3.00 g, 13.9 mmol), 2-(trifluoromethyl)benzeneboronic acid (3.97 g, 20.9 mmol), potassium carbonate (3.86 g, 27.9 mmol) and tetrakistriphenylphosphinepalladium (0) (1.61 g, 1.39 mmol) in 1,4-dioxane (90 mL) and water (18.0 mL) was heated to 50° C. over 2 days under an atmosphere of nitrogen. The reaction was allowed to cool to room temperature and poured into a 1M aqueous solution of hydrogen chloride (50 mL). The aqueous layer was then extracted with ethyl acetate (3×50 mL). The combined organics were washed with water (50 mL), dried over anhydrous magnesium sulfate, filtered and concentrated in vacuo to afford a brown oil. The oil was purified by silica gel column chromatography (10% ethyl acetate in heptane) to afford the title compound as a colourless oil (3.70 g, 95%).

$^1$HNMR (CDCl$_3$): δ 2.62 (s, 3H), 7.02 (d, 1H), 7.35 (d, 1H), 7.45 (dd, 1H), 7.49 (t, 1H), 7.59 (t, 1H), 7.72 (d, 1H), 7.77 (d, 1H)

LCMS Rt=3.67 minutes MS m/z 279 [M–H]$^-$.

PREPARATION 43

(2E)-3-(Dimethylamino)-1-[4-hydroxy-2'-(trifluoromethyl)biphenyl-3-yl]prop-2-en-1-

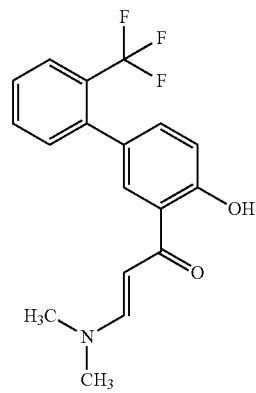 [SMILES: CN(C)/C=C/C(=O)c1cc(-c2ccccc2C(F)(F)F)ccc1O]

N,N-Dimethylformamide dimethyl acetal (0.95 mL, 7.13 mmol) was added to a solution of 1-[4-hydroxy-2'-(trifluoromethyl)biphenyl-3-yl]ethanone (Preparation 42, 1.02 g, 3.65 mmol) in isopropyl alcohol (6.0 mL). The reaction mixture was heated for 18 hours at 45° C. under an atmosphere of nitrogen. After 1 hour, crystallization was observed therefore the stirring was stopped. After 18 hours at 45° C. a yellow precipitate had formed. The reaction mixture was allowed to cool, the yellow precipitate was filtrated and washed with cold isopropyl alcohol to afford the title compound as a yellow solid (840 mg, 69%).

$^1$H NMR (d$_6$-DMSO): δ 2.95 (s, 3H), 3.20 (s, 3H), 5.96 (d, 1H), 6.87 (d, 1H), 7.29 (dd, 1H), 7.44 (d, 1H), 7.59 (t, 1H), 7.71 (t, 1H), 7.82 (d, 1H), 7.86 (d, 1H), 7.93 (d, 1H)

LCMS Rt=3.41 minutes MS m/z 336.43 [MH]$^+$.

PREPARATION 44

5-Chloro-N-(2,4-dimethoxybenzyl)-4-({3-[(2E)-3-(dimethylamino)prop-2-enoyl]-2'-(trifluoromethyl)biphenyl-4-yl}oxy)-2-fluoro-N-1,3,4-thiadiazol-2-ylbenzenesulfonamide

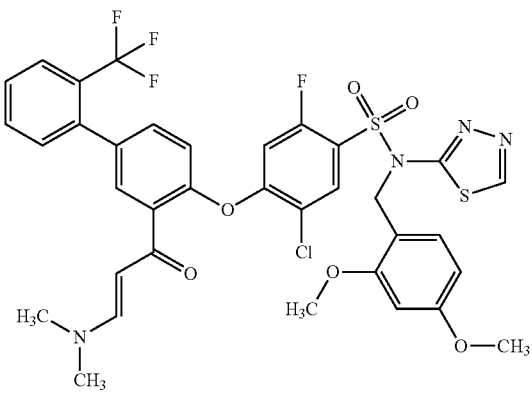 [SMILES: COc1ccc(CN(c2nncs2)S(=O)(=O)c2cc(Cl)c(Oc3ccc(-c4ccccc4C(F)(F)F)cc3C(=O)/C=C/N(C)C)cc2F)c(OC)c1]

To a suspension of (2E)-3-(Dimethylamino)-1-[4-hydroxy-2'-(trifluoromethyl)biphenyl-3-yl]prop-2-en-1-one (Preparation 43, 809 mg, 2.41 mmol) and 5-chloro-N-(2,4-dimethoxybenzyl)-2,4-difluoro-N-1,3,4-thiadiazol-2-ylbenzenesulfonamide (Preparation 16, 1.10 g, 2.39 mmol) in dimethylsulfoxide (10.0 mL) was added potassium carbonate (859 mg, 6.22 mmol). The reaction mixture was stirred for 18 hours at room temperature under an atmosphere of nitrogen. The reaction was poured into a saturated solution of aqueous ammonium chloride (20 mL) and extracted with dichloromethane (3×40 mL). The combined organic phase was washed with brine (3×40 mL), dried over anhydrous sodium sulfate, filtered and concentrated in vacuo to afford a yellow solid (1.96 g). The solid was purified by silica gel column chromatography (40%-75% ethyl acetate in heptane gradient elution) to afford the title compound as a clear glass (563 mg, 30%)

$^1$HNMR (d$_6$-DMSO): δ 2.77 (br.s, 3H), 3.06 (br.s, 3H), 3.68 (s, 3H), 3.73 (s, 3H), 5.13 (s, 2H), 5.35 (br.s, 1H), 6.45 (dd, 1H), 6.47 (d, 1H), 6.77 (br.d, 1H), 7.09 (d, 1H), 7.28 (d, 1H), 7.46-7.53 (m, 4H), 7.63-7.68 (m, 1H), 7.75-7.79 (m, 1H), 7.85-7.89 (m, 2H), 9.31 (s, 1H).

$^{19}$F NMR (d$_6$-DMSO): δ −55.31 (s).

LCMS Rt=3.79 minutes MS m/z 777.10 [MH]$^+$, 779.09 [MH]$^+$.

PREPARATION 45 tert-Butyl 3-{5-[4-(2-chloro-4-{[(2,4-dimethoxybenzyl)(1,3,4-thiadiazol-2-yl)amino]sulfonyl}-5-fluorophenoxy)-2'-(trifluoromethyl)biphenyl-3-yl]-1H-pyrazol-1-yl}azetidine-1-carboxylate

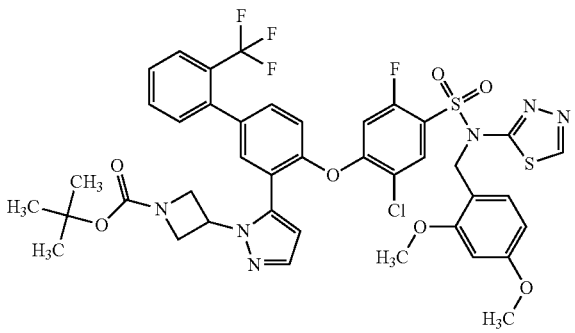 [SMILES: COc1ccc(CN(c2nncs2)S(=O)(=O)c2cc(Cl)c(Oc3ccc(-c4ccccc4C(F)(F)F)cc3-c3ccnn3C3CN(C(=O)OC(C)(C)C)C3)cc2F)c(OC)c1]

(5-Chloro-N-(2,4-dimethoxybenzyl)-4-({3-[(2E)-3-(dimethylamino)prop-2-enoyl]-2'-(trifluoromethyl)biphenyl-4-yl}oxy)-2-fluoro-N-1,3,4-thiadiazol-2-ylbenzenesulfonamide (Preparation 44, 563 mg, 0.724 mmol) in ethanol (10 mL) was slowly added a solution of tert-butyl 3-hydrazinoazetidine-1-carboxylate (Preparation 36, 603 mg, 3.22 mmol) in ethanol (10 mL) and acetic acid (0.25 mL) at 0° C. under nitrogen. The reaction was heated to 70° C. for 3 hours and then cooled to room temperature. The reaction mixture was neutralised to pH7 with saturated aqueous sodium hydrogen carbonate solution (2.0 mL) and concentrated in vacuo to afford a yellow oil. The oil was partitioned between water (100 mL) and ethyl acetate (100 mL). The aqueous layer was then extracted with ethyl acetate (2×100 mL). The combined organic layers were washed with brine (2×100 mL) dried over anhydrous sodium sulfate, filtered and concentrated in vacuo to afford a yellow oil (1.74 g). The oil was partially purified by silica gel column chromatography (0%-10% methanol in dichloromethane gradient elution) to afford the title compound as a solid (228 mg) of 52% purity via LCMS. The compound was used without further purification in the next step.

LCMS Rt=4.06 min MS m/z 651.15 [M−Boc−DMB+H]$^+$, 653.16 [M−Boc−DMB+H]$^+$, 801.25 [M−Boc+H]$^+$, 803.27 [M−Boc+H]$^+$, 923.37 [MNa]$^+$, 925.36 [MNa]$^+$.

PREPARATION 46

4-{[3-(1-Azetidin-3-yl-1H-pyrazol-5-yl)-2'-(trifluoromethyl)biphenyl-4-yl]oxy}-5-chloro-2-fluoro-N-1,3,4-thiadiazol-2-ylbenzenesulfonamide

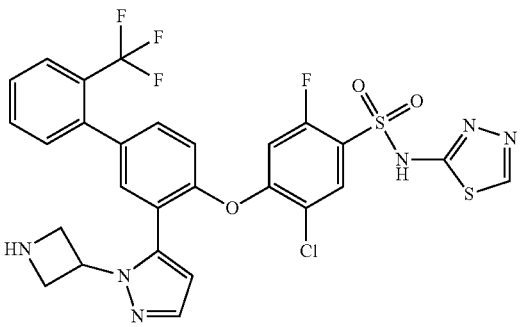 [SMILES: O=S(=O)(Nc1nncs1)c1cc(Cl)c(Oc2ccc(-c3ccccc3C(F)(F)F)cc2-c2ccnn2C2CNC2)cc1F]

Trifluoroacetic acid (0.55 mL, 7.18 mmol) was added to a solution of tert-butyl 3-{5-[4-(2-chloro-4-{[(2,4-dimethoxybenzyl)(1,3,4-thiadiazol-2-yl)amino]sulfonyl}-5-fluorophenoxy)-2'-(trifluoromethyl)biphenyl-3-yl]-1H-pyrazol-1-yl}azetidine-1-carboxylate (Preparation 45, 228 mg, 0.253 mmol) in dichloromethane (20 mL). The mixture was then heated to 40° C. for 18 hours under an atmosphere of nitrogen. The reaction was then cooled to room temperature and concentrated in vacuo to afford a clear oil (236.5 mg). The oil was then purified by preparative HPLC (Trilution method) to afford the title compound as a white solid (42.9 mg, 9% over 2 steps).

$^1$HNMR (d$_6$-DMSO): δ 4.27 (d, 4H), 5.24 (t, 1H), 6.45 (d, 1H), 7.09 (d, 1H), 7.13 (d, 1H), 7.40 (d, 1H), 7.47 (dd, 1H), 7.52 (br.d, 1H), 7.65 (br.t, 1H), 7.72-7.76 (m, 2H), 7.79, (d, 1H), 7.86 (d, 1H), 8.57 (s, 1H)

LCMS Rt=2.30 minutes MS m/z 651.05/653.06 [MH]$^+$

PREPARATION 47

3-Cyano-4-fluoro-N-(1,2,4-thiadiazol-5-yl)benzenesulfonamide

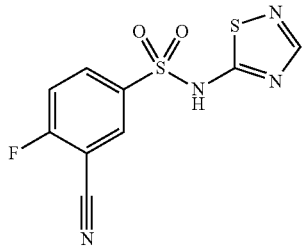 [SMILES: N#Cc1cc(S(=O)(=O)Nc2ncns2)ccc1F]

Sodium hydroxide (5.08 g, 0.127 mmol) was dissolved in water (60 mL) and 1,4-dioxane (300 mL). 1,2,4-thiadiazol-5-amine (10 g, 100 mmol) was added and the reaction stirred for 5 minutes. 3-Cyano-4-fluorobenzene-1-sulfonyl chloride (8.25 g, 37.6 mmol) was added and the reaction was allowed to stir for 3 hours at 20° C. After this time, the reaction was poured into a 1M aqueous solution of hydrogen chloride (150 mL). This solution was extracted with ethyl acetate (3×50 mL). The combined organics were dried over sodium sulfate, filtered and concentrated to give the title compound as a brown solid.

$^1$HNMR (d$_6$-DMSO): δ 7.71 (m, 1H), 8.19 (m, 1H), 8.39 (m, 1H), 8.54 (s, 1H)

LCMS Rt=1.22 minutes MS m/z 283 [MH]+

PREPARATION 48

5-Chloro-N-(2,4-dimethoxybenzyl)-2-fluoro-4-{[3-pyridazin-4-yl-4'-(trifluoromethyl)biphenyl-4-yl]oxy}-N-pyrimidin-2-ylbenzenesulfonamide

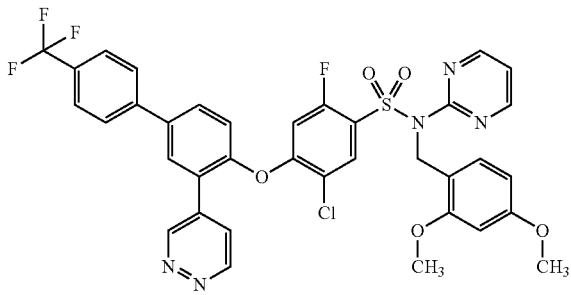 [SMILES: COc1ccc(CN(c2ncccn2)S(=O)(=O)c2cc(Cl)c(Oc3ccc(-c4ccc(C(F)(F)F)cc4)cc3-c3ccnnc3)cc2F)c(OC)c1]

5-Chloro-N-(2,4-dimethoxybenzyl)-2,4-difluoro-N-pyrimidin-2-yl-benzenesulfonamide (Preparation 13, 216 mg, 0.47 mmol), 3-pyridazin-4-yl-4'-(trifluoromethyl)biphenyl-4-ol (Preparation 8, 150 mg, 0.47 mmol) and potassium carbonate (196 mg, 1.42 mmol) were stirred in dimethylsulfoxide (3 mL) at room temperature for 18 hours. A 1M aqueous solution of sodium hydroxide was added to the reaction mixture whereupon a precipitate was observed. The precipitate was collected by filtration and dissolved in ethyl acetate. The ethyl acetate was dried over anhydrous magnesium sulfate, filtered and concentrated in vacuo to afford the title compound as a solid (357 mg, 100%).

$^1$HNMR (CDCl$_3$): δ 3.80 (m, 6H), 5.40 (s, 2H), 6.40 (m, 2H), 6.55 (m, 1H), 6.30 (m, 1H), 7.15 (m, 2H), 7.70 (m, 7H), 8.15 (m, 1H), 8.40 (m, 2H), 9.22 (m, 1H), 9.45 (m, 1H).

LCMS Rt=4.43 minutes MS m/z 752 [MH]+

PREPARATION 49

3-Chloro-N-(methoxymethyl)-N-pyridazin-3-yl-4-{[3-pyridazin-4-yl-4'-(trifluoromethyl)biphenyl-4-yl]oxy}benzenesulfonamide and 3-chloro-N-[(3E)-2-(methoxymethyl)pyridazin-3(2H)-ylidene]-4-{[3-Pyridazin-4-yl-4'-(trifluoromethyl)biphenyl-4-yl]oxy}benzenesulfonamide

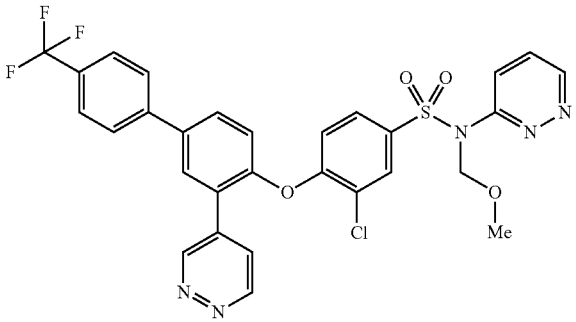

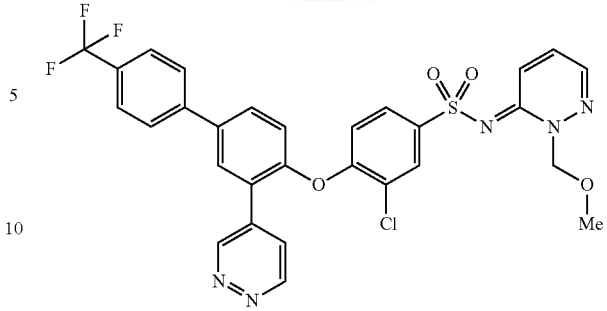

A mixture of regioisomers 3-chloro-4-fluoro-N-(methoxymethyl)-N-(pyridazin-3-yl)benzenesulfonamide and 3-chloro-4-fluoro-N-(methoxymethyl-2H-pyridazin-3-ylidene)benzenesulfonamide (Preparation 11, 157 mg, 0.47 mmol), 3-pyridazin-4-yl-4'-(trifluoromethyl)biphenyl-4-ol (Preparation 8, 150 mg, 0.47 mmol) and potassium carbonate (196 mg, 1.42 mmol) were stirred in dimethylsulfoxide (3 mL) at room temperature for 18 hours. The reaction mixture was then heated at 100° C. for 18 hours. Ethyl acetate (15 mL) was added the mixture was extracted with water (3×5 mL). The organic phase was separated, dried and concentrated in vacuo to afford the title compound (85 mg, 46%). This material was used directly in the next step.

PREPARATION 50

2-Chloro-3'-(trifluoromethyl)biphenyl-4-ol

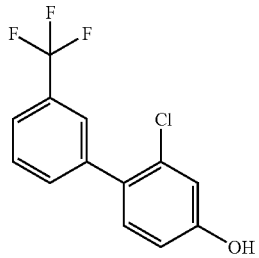 [SMILES: Oc1ccc(-c2cccc(C(F)(F)F)c2)c(Cl)c1]

4-Bromo-3-chlorophenol (518 mg, 2.5 mmol), 3-(trifluoromethyl)phenylboronic acid (617 mg, 3.25 mmol), potassium fluoride (435 mg, 7.5 mmol) palladium acetate (28 mg, 0.125 mmol) and S_phos (102 mg, 0.25 mmol) were stirred in dioxane (10 mL) at 80° C. for 4 hours. The reaction mixture was partitioned between ethyl acetate (100 mL) and water (50 mL). The EtOAc was dried over MgSO$_4$ and evaporated. The residue was resubjected to the reaction conditions and was redissolved in dioxane (10 mL). 3-(trifluoromethyl)phenylboronic acid (380 mg, 2 mmol), potassium fluoride (348 mg, 6 mmol) palladium acetate (14 mg, 0.0625 mmol) and S_phos (51 mg, 0.125 mmol) were added and the reaction stirred at 80° C. for a further 4 hours. The reaction mixture was worked up as before and the crude product was chromatographed on silica eluting with a gradient of heptane:ethyl acetate 100:0 to 75:25. Fractions containing product were evaporated. The resulting material was chromatographed on silica eluting with a gradient of cyclohexane:triethylamine:isopropyl alcohol 95:5:0 to 95:5:10 to give the title compound (310 mg, 1.14 mmol, 45%) as a colourless gum.

$^1$HNMR (400 MHz, CDCl$_3$): δ 6.75 (m, 1H), 6.94 (s, 1H), 7.15 (d, 1H), 7.49 (m, 1H), 7.56 (m, 2H), 7.60 (s, 1H).

LCMS (5.0 min) Rt=3.41 minutes, MS m/z 271 [M−H]$^-$

PREPARATION 51

2-Chloro-5-iodo-3'-(trifluoromethyl)biphenyl-4-ol

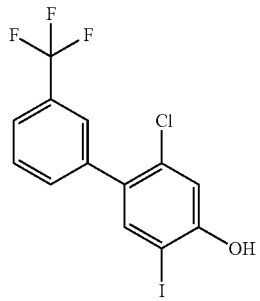 [SMILES: Oc1cc(Cl)c(-c2cccc(C(F)(F)F)c2)cc1I]

2-Chloro-3'-(trifluoromethyl)biphenyl-4-ol (Preparation 50, 310 mg, 1.14 mmol) was dissolved in acetic acid (2 mL), and cooled to 0° C. N-iodosuccinimide (256 mg, 1.14 mmol) was added followed by concentrated sulphuric acid (0.067 μL). The reaction was stirred at room temperature for 18 hours. A second portion of N-iodosuccinimide (25 mg, 0.11 mmol) was added and the reaction stirred at room temperature for a further 1 hour. The reaction mixture was partitioned between ethyl acetate (70 mL) and water (50 mL). The ethyl acetate was separated, dried over MgSO₄, filtered and evaporated. The residue was chromatographed on silica eluting with a gradient of heptane:ethyl acetate 100:0 to 80:20 to give the title compound (230 mg, 0.58 mmol, 51%) as a white solid.

$^1$HNMR (400 MHz, CDCl₃): δ 5.38 (s, 1H), 7.15 (s, 1H), 7.58 (m, 2H), 7.64 (m, 3H). MS m/z 397 [M−H]⁻

PREPARATION 52

2-Chloro-5-(pyridazin-4-yl)-3'-(trifluoromethyl)biphenyl-4-ol

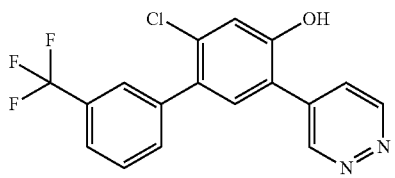 [SMILES: Oc1cc(Cl)c(-c2cccc(C(F)(F)F)c2)cc1-c1ccnnc1]

2-Chloro-5-iodo-3'-(trifluoromethyl)biphenyl-4-ol (Preparation 51, 230 mg, 0.57 mmol) was dissolved in acetonitrile (3 mL), 4-(tributylstannyl)pyridazine (273 mg, 0.75 mmol), caesium fluoride (173 mg, 1.14 mmol), copper iodide (22 mg, 0.114 mmol) and tetrakis(triphenylphosphine)palladium (0) (70 mg, 0.06 mmol) were added. The reaction was stirred at 45° C. for 1.5 hours and then after cooling to room temperature was partitioned between ethyl acetate (100 mL) and water (50 mL) containing 0.880 ammonia (1 mL). The mixture was stirred for 20 minutes. The ethyl acetate phase was separated and washed with an aqueous solution of potassium fluoride (1.5 g in 20 mL), 1M hydrochloric acid (20 mL) and aqueous ammonia (1 mL 0.880 in 50 mL water). The ethyl acetate was dried over MgSO₄, filtered and evaporated. The residue was chromatographed on silica eluting with a gradient of dichloromethane:methanol 100:0 to 95:5 to give the title compound (144 mg, 0.40 mmol, 71%) as a white solid.

$^1$HNMR (400 MHz, d6-DMSO): δ 7.20 (s, 1H), 7.30-7.80 (m, 5H), 7.98 (d, 1H), 9.22 (d, 1H), 9.57 (s, 1H), 10.96 (s, 1H). LCMS (5.0 min) Rt=3.06 minutes, MS m/z 351 [MH]⁺

PREPARATION 53

5-chloro-4-{[2-chloro-5-pyridazin-4-yl-3'-(trifluoromethyl)biphenyl-4-yl]oxy}-N-(2,4-dimethoxybenzyl)-2-fluoro-N-1,3,4-thiadiazol-2-ylbenzenesulfonamide

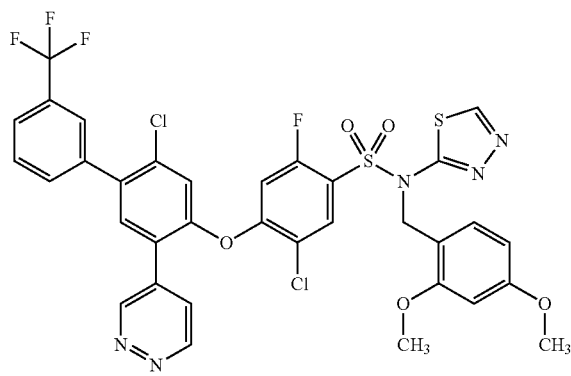 [SMILES: COc1ccc(CN(c2nncs2)S(=O)(=O)c2cc(Cl)c(Oc3cc(Cl)c(-c4cccc(C(F)(F)F)c4)cc3-c3ccnnc3)cc2F)c(OC)c1]

2-Chloro-5-(pyridazin-4-yl)-3'-(trifluoromethyl)biphenyl-4-ol (Preparation 52, 140 mg, 0.4 mmol) was dissolved in DMSO (1 mL) and potassium carbonate (110 mg, 0.8 mmol) was added followed by 5-chloro-N-(2,4-dimethoxybenzyl)-2,4-difluoro-N-(1,3,4-thiadiazol-2-yl)benzenesulfonamide (Preparation 16, 203 mg, 0.44 mmol). The reaction was stirred at room temperature for 18 hours and then partitioned between ethyl acetate (50 mL) and water (40 mL). The ethyl acetate was separated and dried over MgSO₄, filtered and evaporated. The residue was chromatographed on silica eluting with a gradient of heptane:ethyl acetate 80:20 to 20:80 to give the title compound (231 mg, 0.30 mmol, 73%) as a white solid.

$^1$HNMR (400 MHz, CDCl₃): δ 3.70 (s, 3H), 3.75 (s, 3H), 5.30 (s, 2H), 6.24 (s, 1H), 6.35 (d, 1H), 6.63 (d, 1H), 7.30 (m, 2H), 7.34, (d, 1H), 7.50-7.75 (m, 5H), 7.82 (d, 1H), 8.83 (s, 1H), 9.28 (d, 1H), 9.42 (s, 1H).
LCMS (5.0 min) Rt=3.85 minutes, MS m/z 792 M[H]+

PREPARATION 54

4'-Chloro-3'-(trifluoromethyl)biphenyl-4-ol

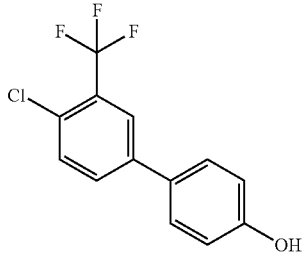 [SMILES: Oc1ccc(-c2ccc(Cl)c(C(F)(F)F)c2)cc1]

4-Chloro-3-(trifluoromethyl)phenylboronic acid (448 mg, 2 mmol) and 4-iodophenol (440 mg, 2 mmol) were dissolved in dioxane (10 mL). Caesium carbonate (1.95 g, 6 mmol), water (2 mL) and tetrakis(triphenylphosphine)palladium (0) (231 mg, 0.2 mmol) were added and the reaction stirred at 80° C. for 1 hour. The reaction was quenched with 2M HCl (5 mL) and partitioned between ethyl acetate (50 mL) and water (50 mL). The ethyl acetate was separated, dried over MgSO$_4$ and evaporated. The crude product was chromatographed on silica eluting with a gradient of heptane:ethyl acetate 100:0 to 80:20 to give the title compound (150 mg, 0.55 mmol, 27%) as a white solid.

$^1$HNMR (400 MHz, CDCl$_3$): δ 4.82 (br-s, 1H, OH), 6.92 (d, 2H), 7.44 (d, 2H), 7.51 (d, 1H), 7.58 (d, 1H), 7.80 (s, 1H).

LCMS (5.0 min) Rt=3.42 minutes, MS m/z 271 [M–H]$^-$

PREPARATION 55

4'-Chloro-3-iodo-3'-(trifluoromethyl)biphenyl-4-ol

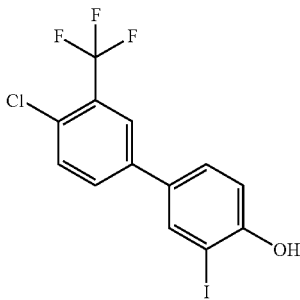 [SMILES: Oc1ccc(-c2ccc(Cl)c(C(F)(F)F)c2)cc1I]

4'-Chloro-3'-(trifluoromethyl)biphenyl-4-ol (Preparation 54, 150 mg, 0.55 mmol) was dissolved in acetic acid (5 mL) and concentrated sulphuric acid (0.032 μL) was added followed by N-iodosuccinimide (124 mg, 0.55 mmol). The reaction was stirred at room temperature for 18 hours and then partitioned between ethyl acetate (50 mL) and water (20 mL). The ethyl acetate was separated, dried over MgSO$_4$, filtered and evaporated. The crude product was chromatographed on silica eluting with a gradient of heptane:ethyl acetate 100:0 to 85:15 to give the title compound (167 mg, 0.42 mmol, 76%) as a gum.

$^1$HNMR (400 MHz, CDCl$_3$): δ 5.40 (br-s, 1H, OH), 7.06 (d, 1H), 7.44 (d, 1H), 7.55 (m, 1H), 7.58 (m, 1H), 7.79 (s, 1H), 7.84 (s, 1H).

LCMS (5.0 min) Rt=3.65 minutes, MS m/z 397 [M–H]$^-$

PREPARATION 56

4'-Chloro-3-(pyridazin-4-yl)-3'-(trifluoromethyl)biphenyl-4-ol

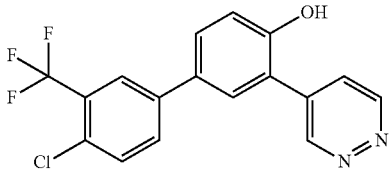 [SMILES: Oc1ccc(-c2ccc(Cl)c(C(F)(F)F)c2)cc1-c1ccnnc1]

4'-Chloro-3-iodo-3'-(trifluoromethyl)biphenyl-4-ol (Preparation 55, 167 mg, 0.42 mmol) was dissolved in acetonitrile (1 mL) and 4-(tributylstannyl)pyridazine (200 mg, 0.55 mmol), caesium fluoride (127 mg, 0.84 mmol), copper iodide (16 mg, 0.084 mmol) and tetrakis(triphenylphosphine) palladium (0) (46 mg, 0.04 mmol) were added. The reaction was stirred at 45° C. for 40 minutes and then partitioned between ethyl acetate (50 mL) and water (10 mL) containing 0.880 ammonia (1 mL). The mixture was stirred for 20 minutes. The ethyl acetate was separated, dried over MgSO$_4$, filtered and evaporated. The residue was chromatographed on silica eluting with a gradient of dichloromethane:methanol: 0.880NH$_3$ 100:0:0 to 92:8:0.8 to give the title compound (95 mg, 0.27 mmol, 64%) as a white solid.

$^1$HNMR (400 MHz, DMSO-d6): δ 7.15 (d, 1H), 7.75-7.78 (m, 2H), 7.90 (s, 1H), 8.00 (m, 2H), 8.08 (s, 1H), 9.24 (d, 1H) 9.58 (s, 1H), 10.58 (br-s, 1H, OH).

LCMS (5.0 min) Rt=3.08 minutes, MS m/z 349 [M–H]$^-$

PREPARATION 57

5-chloro-4-{[4'-chloro-3-pyridazin-4-yl-3'-(trifluoromethyl)biphenyl-4-yl]oxy}-N-(2,4-dimethoxybenzyl)-2-fluoro-N-1,3,4-thiadiazol-2-ylbenzenesulfonamide

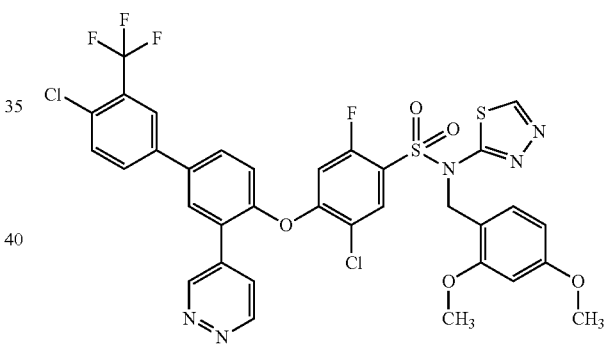

4'-Chloro-3-(pyridazin-4-yl)-3'-(trifluoromethyl)biphenyl-4-ol (Preparation 56, 88 mg, 0.25 mmol) was dissolved in DMSO (1 mL), potassium carbonate (69 mg, 0.5 mmol) was added followed by 5-chloro-N-(2,4-dimethoxybenzyl)-2,4-difluoro-N-(1,3,4-thiadiazol-2-yl)benzenesulfonamide (Preparation 16, 127 mg, 0.27 mmol). The reaction was stirred at room temperature for 3 hours and then partitioned between ethyl acetate (50 mL) and water (50 mL). The organic phase was separated and washed with water (2×50 mL), dried over MgSO$_4$, filtered and evaporated. The crude product was chromatographed on silica eluting with a gradient of heptane:ethyl acetate 100:0 to 20:80 to give the title compound (135 mg, 0.17 mmol, 69%) as a white solid.

$^1$HNMR (400 MHz, DMSO-d6): δ 3.62 (s, 3H), 3.68 (s, 3H), 5.14 (s, 2H), 6.40 (m, 2H), 7.06 (d, 1H), 7.28 (d, 1H), 7.34 (d, 1H), 7.84 (m, 2H), 7.95 (m, 2H), 8.13 (m, 1H), 8.16 (s, 1H), 8.22 (s, 1H), 9.30 (m, 2H), 9.54 (s, 1H).

LCMS (5.0 min) Rt=3.88 minutes, MS m/z 792 [MH]$^+$

PREPARATION 58

5-chloro-N-(2,4-dimethoxybenzyl)-2-fluoro-4-{2-pyridazin-4-yl-4-[6-(trifluoromethyl)pyridin-3-yl]phenoxy}-N-1,3,4-thiadiazol-2-ylbenzenesulfonamide

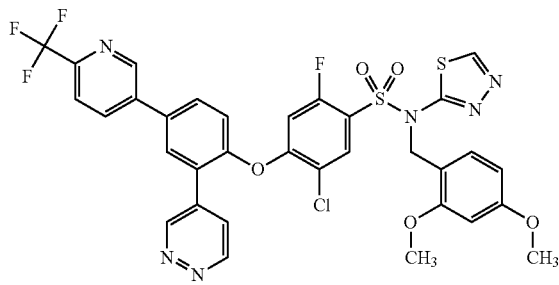 [SMILES: COc1ccc(CN(c2nncs2)S(=O)(=O)c2cc(Cl)c(Oc3ccc(-c4ccc(C(F)(F)F)nc4)cc3-c3ccnnc3)cc2F)c(OC)c1]

2-(Pyridazin-4-yl)-4-(6-(trifluoromethyl)pyridin-3-yl)phenol (Preparation 59, 360 mg, 1.134 mmol) was dissolved in DMSO (6 mL) and potassium carbonate (313 mg, 2.27 mmol) was added followed by 5-chloro-N-(2,4-dimethoxybenzyl)-2-difluoro-N-(1,3,4-thiadiazol-2-yl)benzenesulfonamide (Preparation 16, 524 mg, 1.134 mmol). The reaction was stirred at room temperature for 18 hours and then partitioned between ethyl acetate and water. The organic layer was separated, washed with brine, dried over anhydrous MgSO$_4$, filtered and concentrated in vacuo. The residue was purified on silica gel by Biotage (20% to 100% EtOAc in heptane over 20 CV) to give the title compound (501 mg, 58%) as yellow foam.

$^1$HNMR (400 MHz, CDCl$_3$): δ 3.65 (s, 3H), 3.70 (s, 3H), 5.30 (s, 2H), 6.20 (s, 1H), 6.30 (d, 1H), 6.65 (d, 1H), 7.15 (d, 1H), 7.20 (m, 1H), 7.70-7.90 (m, 5H), 8.10 (d, 1H), 8.80 (s, 1H), 8.95 (s, 1H), 9.30 (d, 1H), 9.45 (s, 1H).

$^{19}$F NMR (400 MHz, CDCl$_3$): δ −68.0, −104.0.

MS No mass ion seen

PREPARATION 59

2-(Pyridazin-4-yl)-4-(6-(trifluoromethyl)pyridin-3-yl)phenol

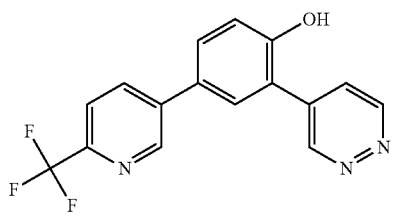 [SMILES: Oc1ccc(-c2ccc(C(F)(F)F)nc2)cc1-c1ccnnc1]

2-Iodo-4-(6-(trifluoromethyl)pyridin-3-yl)phenol (Preparation 60, 840 mg, 2.30 mmol) was dissolved in acetonitrile (20 mL) and 4-(tributylstannyl)pyridazine (1.10 g, 2.99 mmol), caesium fluoride (698 mg, 4.60 mmol), copper iodide (87 mg, 0.46 mmol) and tetrakis(triphenylphosphine)palladium (0) (266 mg, 0.23 mmol) were added. The reaction mixture was stirred at 80° C. for 18 hours and then partitioned between ethyl acetate and water containing 0.88 ammonia. The resulting mixture was stirred for 15 minutes and then filtered through a pad of celite. The aqueous phase was separated and extracted with ethyl acetate (2×20 mL) and the combined organic phases were washed with brine, dried over anhydrous MgSO$_4$, filtered and concentrated in vacuo. The residue was purified on silica gel by Biotage (10% to 100% EtOAc in heptane over 25 CV) to give a mixture of the title compound and triphenylphosphine oxide. The residue was triturated with dichloromethane to give the title compound (360 mg, 50%) as a white solid.

$^1$HNMR (400 MHz, CDCl$_3$): δ 4.9 (s, 1H), 7.05 (d, 1H), 7.75 (d, 1H), 7.90 (m, 2H), 8.05 (d, 1H), 8.30 (d, 1H), 9.00 (s, 1H), 9.2 (s, 1H), 9.6 (s, 1H).

$^{19}$F NMR (400 MHz, CDCl$_3$): δ −69.0

LCMS Rt=2.24 minutes, MS m/z 318 [MH]$^+$.

PREPARATION 60

2-iodo-4-[6-(trifluoromethyl)pyridin-3-yl]phenol

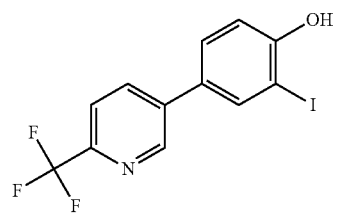 [SMILES: Oc1ccc(-c2ccc(C(F)(F)F)nc2)cc1I]

4-(6-(Trifluoromethyl)pyridin-3-yl)phenol (Preparation 61, 1.24 g, 5.18 mmol) was dissolved in a mixture of acetic acid (10 mL), dichloromethane (10 mL) and CH$_3$CN (10 mL) at room temperature. Concentrated sulphuric acid (0.5 mL) was then added followed by N-iodosuccinimide (1.052 g, 4.67 mmol). The reaction was stirred at room temperature for 18 hours. A further aliquot of N-iodosuccinimide (116 mg, 0.518 mmol) was added and the reaction mixture was stirred for one hour and concentrated in vacuo. The crude oil was purified on silica gel by Biotage™ (5% to 60% of EtOAc in heptane over 20 CV) and fractions containing product were evaporated to give an inseparable mixture of product/starting material 7:3 (840 mg). This was used directly in the next stage without further purification.

$^1$HNMR (400 MHz, CDCl$_3$): δ 6.90 (d, 1H), 7.40 (d, 1H), 7.60 (s, 1H), 7.80 (d, 1H), 7.85 (m, 1H), 8.80 (s, 1H).

$^{19}$F NMR (400 MHz, CDCl$_3$): δ −68.0

LCMS Rt=2.69 minutes, MS m/z 363 [M−H]

PREPARATION 61

4-(6-(Trifluoromethyl)pyridin-3-yl)phenol

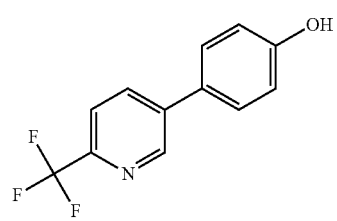 [SMILES: Oc1ccc(-c2ccc(C(F)(F)F)nc2)cc1]

5-Bromo-2-(trifluoromethyl)pyridine (1.18 g, 5.51 mmol), 4-hydroxyphenylboronic acid (775 mg, 5.51 mmol) and sodium carbonate (2.34 g, 22.0 mmol) were combined and dissolved in a mixture of dioxane/water (30 mL/6 mL). The reaction mixture was degassed and then tetrakistriphenylphosphinepalladium (0) (322 mg, 0.275 mmol) was added and the reaction mixture was heated at 70° C. for 18 hours. The cooled reaction mixture was partitioned between ethyl acetate and water. The organic layer was separated and washed with brine, dried over anhydrous MgSO$_4$ and concentrated in vacuo. The residue was purified on silica gel by Biotage™ (7% to 60% EtOAc in heptane over 20 CV) to give the title compound (1.24 g, 95%) as a white solid.

$^1$H NMR (400 MHz, CDCl$_3$): δ 5.30 (s, 1H), 6.95 (d, 2H), 7.50 (m, 2H), 7.85 (d, 1H), 7.95 (d, 1H), 8.85 (s, 1H).

LCMS Rt=2.71 minutes MS m/z 240 [MH]$^+$

PREPARATION 62

5-Chloro-4-{[3'-cyano-3-(3-nitro-1H-pyrazol-4-yl)biphenyl-4-yl]oxy}-2-fluoro-N-1,3,4-thiadiazol-2-ylbenzenesulfonamide

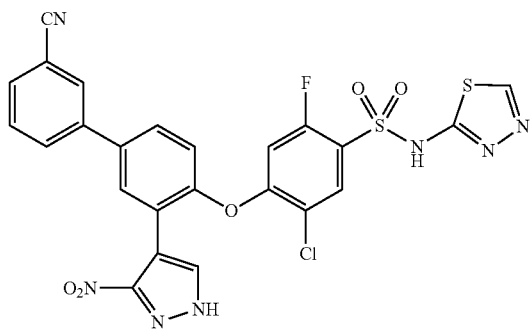 [SMILES: N#Cc1cccc(-c2ccc(Oc3cc(F)c(S(=O)(=O)Nc4nncs4)cc3Cl)c(-c3c[nH]nc3[N+](=O)[O-])c2)c1]

5-Chloro-4-(3'-cyano-3-(3-nitro-1-(tetrahydro-2H-pyran-2-yl)-1H-pyrazol-4-yl)biphenyl-4-yloxy)-N-(2,4-dimethoxybenzyl)-2-fluoro-N-(1,3,4-thiadiazol-2-yl)benzenesulfonamide (Preparation 63, 447 mg, 0.537 mmol) was dissolved in a 4M solution of HCl in 1,4-dioxane (2.7 mL, 10.74 mmol). The reaction mixture was stirred at room temperature for 18 hours and then concentrated in vacuo. The residue was purified by reverse phase chromatography on the ISCO™ system to afford the title compound (204 mg, 64%) as a white solid.

$^1$HNMR (400 MHz, d-6DMSO): δ 6.80 (d, 1H), 7.25 (d, 1H), 7.65 (t, 1H), 7.80 (m, 3H), 7.95 (s, 1H), 8.05 (dd, 1H), 8.20 (d, 1H), 8.25 (d, 1H), 8.80 (s, 1H).

$^{19}$F NMR (400 MHz, d-6DMSO): δ −107.0

LCMS Rt=3.13 minutes, MS m/z 596 [M−H]

PREPARATION 63

5-chloro-4-({3'-cyano-3-[3-nitro-1-(tetrahydro-2H-pyran-2-yl)-1H-pyrazol-4-yl]biphenyl-4-yl}oxy)-N-(2,4-dimethoxybenzyl)-2-fluoro-N-1,3,4-thiadiazol-2-ylbenzenesulfonamide

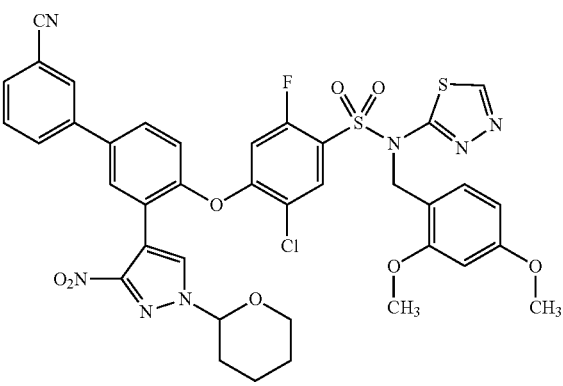 [SMILES: COc1ccc(CN(c2nncs2)S(=O)(=O)c2cc(Cl)c(Oc3ccc(-c4cccc(C#N)c4)cc3-c3cn(C4CCCCO4)nc3[N+](=O)[O-])cc2F)c(OC)c1]

4'-Hydroxy-3'-(3-nitro-1-(tetrahydro-2H-pyran-2-yl)-1H-pyrazol-4-yl)biphenyl-3-carbonitrile (Preparation 64, 250 mg, 0.64 mmol) was dissolved in DMSO (3.5 mL) and potassium carbonate (177 mg, 1.28 mmol) was added followed by 5-chloro-N-(2,4-dimethoxybenzyl)-2,4-difluoro-N-(1,3,4-thiadiazol-2-yl)benzenesulfonamide (Preparation 16, 310 mg, 0.67 mmol). The reaction was stirred at room temperature for 1 hour and then partitioned between ethyl acetate and water. The aqueous phase was separated and extracted with EtOAc (3×5 mL) and the combined organic layers were washed with brine, dried over anhydrous MgSO$_4$, filtered and concentrated in vacuo. The residue was purified on silica gel by Biotage™ (10% to 80% EtOAc in heptane over 12 CV) to give the title compound (451 mg, 85%) as a light yellow foam.

$^1$HNMR (400 MHz, CDCl$_3$): δ 1.60 (m, 3H), 2.00 (m, 2H), 2.20 (m, 1H), 3.60 (s, 3H), 3.75 (s, 3H), 3.80 (m, 1H), 4.05 (m, 1H), 5.20 (s, 2H), 5.40 (d, 1H), 6.2 (br s, 1H), 6.30 (d, 1H), 6.55 (d, 1H), 7.05 (d, 1H), 7.20 (d, 1H), 7.55-7.80 (m, 7H), 7.90 (s, 1H), 8.8 (s, 1H).

$^{19}$F NMR (400 MHz, CDCl$_3$): δ −104.0

LCMS Rt=3.25 minutes, MS no mass ion detected.

PREPARATION 64

4'-Hydroxy-3'-(3-nitro-1-(tetrahydro-2H-pyran-2-yl)-1H-pyrazol-4-yl)biphenyl-3-carbonitrile

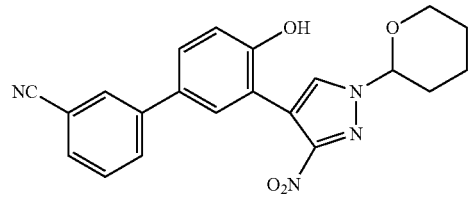 [SMILES: N#Cc1cccc(-c2ccc(O)c(-c3cn(C4CCCCO4)nc3[N+](=O)[O-])c2)c1]

4-Chloro-2-(3-nitro-1-(tetrahydro-2H-pyran-2-yl)-1H-pyrazol-4-yl)phenol (500 mg, 1.544 mmol), 3-cyanophenylboronic acid (453 mg, 3.09 mmol), di-mu-chlorobis[5- chloro-2-[(4-chlorophenyl)(hydroxyimino)methyl]phenyl] palladium (II) dimer (63 mg, 0.0772 mmol), tri-tert-butylphosphonium tetrafluoroborate (45 mg, 0.154 mmol), potassium carbonate (426 mg, 3.09 mmol) and tetrabutyl ammonium hydroxyde solution (1M in MeOH, 0.31 mL, 0.31 mmol) were combined in a microwave vial. DMF (7.5 mL) was added and the vial was sealed. The mixture was heated at 130° C. for 1 hour under microwave irradiation and then partitioned between ethyl acetate (25 mL) and water (10 mL). The organic layer was separated and washed with brine (10 mL), dried over anhydrous MgSO$_4$, filtered and concentrated in vacuo. The residue was purified on silica gel by Biotage™ (10% to 80% EtOAc in heptane over 20 CV) to give the title compound (254 mg, 41%) as brown oil $^1$HNMR (400 MHz, CDCl$_3$): δ 1.70 (m, 3H), 2.00 (m, 2H), 2.20 (m, 1H), 3.85 (m, 1H), 4.05 (m, 1H), 5.30 (br s, 1H), 5.50 (d, 1H), 7.00 (d, 1H), 7.40 (s, 1H), 7.50 (m, 2H), 7.60 (d, 1H), 7.75 (d, 1H), 7.8 (m, 2H).

LCMS Rt=2.79 minutes, MS m/z 389 [M−H]

PREPARATION 65 tert-Butyl {[4'-{2-cyano-4-[(1,3-thiazol-2-ylamino)sulfonyl]phenoxy}-3'-(1-methyl-1H-pyrazol-5-yl)biphenyl-2-yl]methyl}methylcarbamate

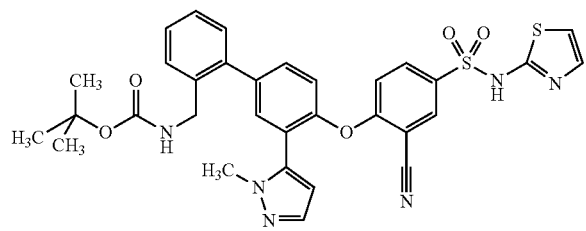 [SMILES: Cn1nccc1-c1cc(-c2ccccc2CNC(=O)OC(C)(C)C)ccc1Oc1ccc(S(=O)(=O)Nc2nccs2)cc1C#N]

4-[4-Bromo-2-(1-methyl-1H-pyrazol-5-yl)phenoxy]-3-cyano-N-1,3-thiazol-2-ylbenzene sulfonamide (Patent WO 2010079443, 500 mg, 0.97 mmol) was dissolved in dimethylformamide (3 mL) and added to a 5 mL microwave vial under nitrogen. Bis(pinacolato) diboron (327 mg, 1.33 mmol), (1,1'-bis(diphenylphosphino)ferrocene)-dichloropalladium (II) (71 mg, 0.1 mmol) and potassium acetate (475 mg, 4.84 mmol) were added. The reaction vessel was sealed and then heated to 100° C. for 1 hour in the microwave. The cooled reaction mixture was partitioned between ethyl acetate (20 mL) and water (20 mL). The organic layer was separated, filtered and then concentrated in vacuo. The residue was dissolved in 1,4-dioxane (3 mL) and added to a 5 mL microwave vial under nitrogen. Tert-butyl (2-iodobenzyl)methylcarbamate (European Journal of Organic Chemistry, 2010, 19, 3704-3710) (504 mg, 1.45 mmol), bis(triphenylphosphine) palladium (II) dichloride (68 mg, 0.1 mmol), potassium carbonate (334 mg, 2.42 mmol) and water (0.5 mL) were added and the reaction vessel sealed and then heated to 125° C. for 30 minutes in the microwave. The crude material was partitioned between ethyl acetate (20 mL) and 0.2M aqueous solution of HCl (20 mL). The organic layer was separated, filtered and then concentrated in vacuo and purified by silica gel column chromatography (ISCO™, 12 g silica, 99:1 DCM:formic acid to 90:10:1 DCM:MeOH:formic acid gradient to afford the title compound (630 mg, 100%) as a brown oil.

$^1$HNMR (CDCl$_3$): δ 1.42 (s, 9H), 2.72 (s, 3H), 3.90 (s, 3H), 3.96 (s 2H), 4.45 (br s, 1H) 6.25 (d, 1H) 6.59 (d, 1H), 6.81 (d, 1H) 7.07 (d, 1H) 7.40 (m, 8H), 7.94 (dd, 1H), 8.12 (d, 1H).

LCMS Rt=1.69 minutes MS m/z 657 [MH]$^+$.

PREPARATION 66

5-Chloro-4-(2-chloro-3'-fluoro-5-(pyridazin-4-yl)biphenyl-4-yloxy)-N-(2,4-dimethoxybenzyl)-2-fluoro-N-(1,3,4-thiadiazol-2-yl)benzenesulfonamide

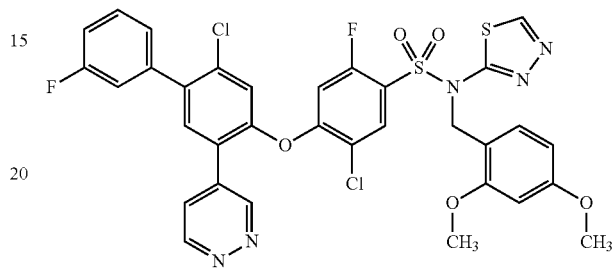

2-Chloro-3'-fluoro-5-(pyridazin-4-yl)biphenyl-4-ol (Preparation 67, 98 mg, 0.33 mmol) was dissolved in dimethylsulfoxide (2 mL) and 5-chloro-N-(2,4-dimethoxybenzyl)-2,4-difluoro-N-(1,3,4-thiadiazol-2-yl)benzenesulfonamide (Preparation 16, 181 mg, 0.39 mmol) and potassium carbonate (135 mg, 0.98 mmol) were added. The reaction was stirred at room temperature for 18 hours. Water (10 mL) and ethyl acetate (15 mL) were added and the two layers were separated. The aqueous phase was extracted with ethyl acetate (10 mL). The combined organic extracts were washed with brine (10 mL), dried over anhydrous MgSO$_4$, filtered and concentrated in vacuo. The residue was purified by silica gel column chromatography (20% heptane in ethyl acetate) to give the title compound (165 mg, 67%) as an off-white solid.

$^1$HNMR (400 MHz, CDCl$_3$): δ 3.64 (s, 3H), 3.68 (s, 3H), 5.24 (s, 2H), 6.20 (s, 1H), 6.30 (d, 1H), 6.56 (d, 1H), 7.15 (m, 5H), 7.38 (dd, 1H), 7.48 (s, 1H), 7.60 (dd, 1H), 7.78 (d, 1H), 8.76 (s, 1H), 9.18 (d, 1H), 9.36 (s, 1H).

LCMS Rt=3.62 minutes MS m/z 742 [MH]$^+$

PREPARATION 67

2-Chloro-3'-fluoro-5-(pyridazin-4-yl)biphenyl-4-ol

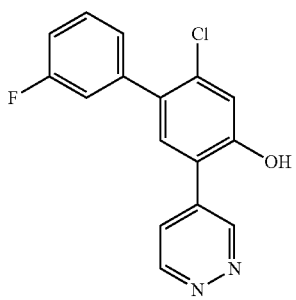 [SMILES: Oc1cc(Cl)c(-c2cccc(F)c2)cc1-c1ccnnc1]

2-Chloro-3'-fluoro-5-iodobiphenyl-4-ol (Preparation 68, 480 mg, 1.38 mmol) and 4-(tributylstannyl)pyridazine (610 mg, 1.65 mmol) were dissolved in degassed acetonitrile (7 mL). Caesium fluoride (418 mg, 2.75 mmol) was added and the mixture further degassed. Tetrakis(triphenylphosphine) palladium (0) (159 mg, 0.14 mmol) and copper (I) iodide (79 mg, 0.41 mmol) were added and the reaction heated at 50° C. for 2 hours. The reaction mixture was cooled and filtered through celite, washing with ethyl acetate. The organic solution was washed with water and brine, dried over anhydrous MgSO$_4$, filtered and evaporated. The residue was purified by silica gel column chromatography (20% heptane in ethyl acetate) followed by trituration with dichloromethane to give the title compound (98 mg, 24%) as a white solid.

$^1$HNMR (400 MHz, d6-DMSO): δ 7.14 (s, 1H), 7.20 (dd, 1H), 7.34 (m, 2H), 7.26 (dd, 1H), 7.56 (s, 1H), 7.94 (d, 1H), 9.22 (d, 1H), 9.56, (s, 1H), 10.86 (s, 1H).

PREPARATION 68

2-Chloro-3'-fluoro-5-iodobiphenyl-4-ol

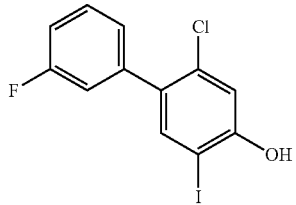 [SMILES: Oc1cc(Cl)c(-c2cccc(F)c2)cc1I]

2-Chloro-3'-fluorobiphenyl-4-ol (Preparation 69, 500 mg, 2.25 mmol) was dissolved in dichloromethane (5 mL) and acetic acid (5 mL). Concentrated sulfuric acid (0.05 mL) was added followed by N-iodosuccinimide (480 mg, 2.13 mmol) and the reaction stirred at room temperature for 18 hours. A further portion of N-iodosuccinimide (50 mg, 0.22 mmol) was added and stirring continued at room temperature for 3 hours. Water and dichloromethane were added and the two layers separated. The organic layer was washed twice with brine, dried over MgSO$_4$, filtered and concentrated in vacuo. The residue was purified by silica gel column chromatography (20% ethyl acetate in heptane) to afford the title compound (496 mg, 63%) as a yellow oil that solidified on standing.

$^1$HNMR (400 MHz, CDCl$_3$): δ 5.40 (s, 1H), 7.10 (m, 4H), 7.36 (dd, 1H), 7.62 (s, 1H).

LCMS Rt=2.67 minutes MS m/z 347 [M−H]$^−$

PREPARATION 69

2-Chloro-3'-fluorobiphenyl-4-ol

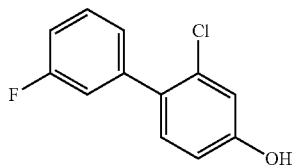 [SMILES: Oc1ccc(-c2cccc(F)c2)c(Cl)c1]

3-Fluorobenzeneboronic acid (405 mg, 2.89 mmol) and 4-bromo-3-chlorophenol (500 mg, 2.41 mmol) were dissolved in dioxane (15 mL) and water (3 mL) and the solution degassed. Tetrakis(triphenylphosphine) palladium (0) (278 mg, 0.24 mmol) was added followed by caesium carbonate (2.36 g, 7.23 mmol) and the reaction was stirred at 80° C. under nitrogen for 18 hours. The reaction mixture was cooled to room temperature and partitioned between ethyl acetate and water. The aqueous layer was separated and extracted with ethyl acetate. The combined organic extracts were washed with brine, dried over MgSO$_4$, filtered and concentrated in vacuo. The residue was purified by silica gel column chromatography (20% ethyl acetate in heptane) to afford the title compound (509 mg, 95%) as a colourless oil.

$^1$HNMR (400 MHz, CDCl$_3$): δ 6.80 (d, 1H), 7.00 (s, 1H), 7.06 (dd, 1H), 7.12 (dd, 1H), 7.18 (m, 2H), 7.36 (dd, 1H).

LCMS Rt=3.02 minutes MS m/z 221 [M−H]

PREPARATION 70

5-Chloro-4-(2-chloro-4'-fluoro-5-(pyridazin-4-yl)biphenyl-4-yloxy)-N-(2,4-dimethoxybenzyl)-2-fluoro-N-(1,3,4-thiadiazol-2-yl)benzenesulfonamide

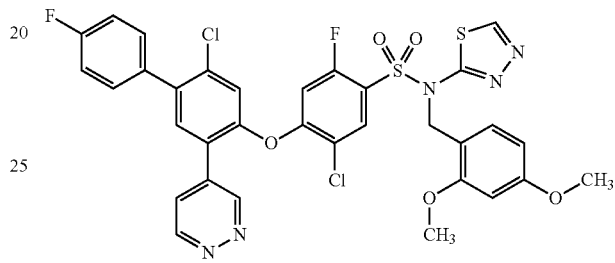

2-Chloro-4'-fluoro-5-(pyridazin-4-yl)biphenyl-4-ol (Preparation 71, 148 mg, 0.49 mmol) was dissolved in dimethylsulfoxide (3 mL) and 5-chloro-N-(2,4-dimethoxybenzyl)-2,4-difluoro-N-(1,3,4-thiadiazol-2-yl)benzenesulfonamide (Preparation 16, 273 mg, 0.59 mmol) and potassium carbonate (204 mg, 1.48 mmol) were added. The reaction was stirred at 20° C. for 18 hours and then partitioned between water and ethyl acetate. The aqueous phase was separated and extracted with ethyl acetate. The combined organic extracts were washed with brine, dried over MgSO$_4$, filtered and concentrated in vacuo. The residue was purified by silica gel column chromatography (20% heptane in ethyl acetate) to give the title compound (224 mg, 62%) as an off-white solid.

$^1$HNMR (400 MHz, CDCl$_3$): δ 3.68 (s, 3H), 3.76 (s, 3H), 5.32 (s, 2H), 6.26 (s, 1H), 6.36 (d, 1H), 6.60 (d, 1H), 7.18 (d, 2H), 7.22 (s, 1H), 7.26 (d, 1H), 7.46 (dd, 2H), 7.54 (s, 1H), 7.68 (d, 1H), 7.84 (d, 1H), 8.82 (s, 1H), 9.24 (d, 1H), 9.42 (s, 1H).

LCMS Rt=3.76 minutes MS m/z 742 [MH]$^+$.

PREPARATION 71

2-Chloro-4'-fluoro-5-(pyridazin-4-yl)biphenyl-4-ol

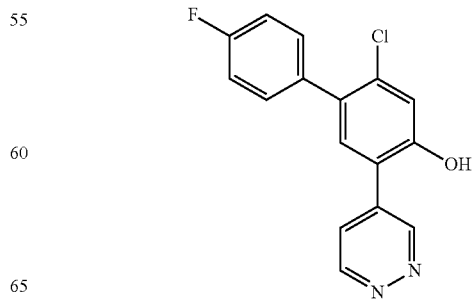

2-Chloro-4'-fluoro-5-iodobiphenyl-4-ol (Preparation 72, 553 mg, 1.59 mmol) and 4-(tributylstannyl)pyridazine (703 mg, 1.90 mmol) were dissolved in degassed acetonitrile (8 mL). Caesium fluoride (482 mg, 3.17 mmol) was added and the mixture further degassed. Tetrakistriphenylphosphine-palladium (0) (183 mg, 0.16 mmol) and copper (I) iodide (91 mg, 0.48 mmol) were added and the reaction heated at 50° C. for 2 hours. The reaction mixture was cooled and filtered through celite, washing with ethyl acetate. The organic solution was washed with water and brine, dried over MgSO$_4$, filtered and concentrated in vacuo. The residue was purified by trituration with hot ethyl acetate to give the title compound (151 mg, 32%) as a beige solid.

$^1$HNMR (400 MHz, d6-DMSO): δ 7.18 (s, 1H), 7.26 (dd, 2H), 7.72 (dd, 2H), 7.76 (s, 1H), 7.96 (d, 1H), 9.24 (d, 1H), 9.56, (s, 1H), 10.82 (s, 1H).

LCMS Rt=2.62 minutes MS m/z 301 [MH]$^+$.

PREPARATION 72

2-Chloro-4'-fluoro-5-iodobiphenyl-4-ol

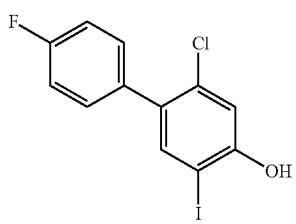 [SMILES: Oc1cc(Cl)c(-c2ccc(F)cc2)cc1I]

2-Chloro-4'-fluorobiphenyl-4-ol (Preparation 73, 503 mg, 2.26 mmol) was dissolved in dichloromethane (5 mL) and acetic acid (5 mL). Concentrated sulfuric acid (0.05 mL) was added followed by N-iodosuccinimide (508 mg, 2.26 mmol) and the reaction stirred at room temperature for 2 hours before partitioning it between water and dichloromethane. The organic layer was separated and washed twice with brine, dried over MgSO$_4$, filtered and concentrated in vacuo. The residue was purified by silica gel column chromatography (20% ethyl acetate in heptane) to afford the title compound (553 mg, 70%) as an orange oil.

$^1$HNMR (400 MHz, CDCl$_3$): δ 5.36 (s, 1H), 7.10 (dd, 2H), 7.14 (s, 1H), 7.36 (dd, 2H), 7.62 (s, 1H).

LCMS Rt=2.64 minutes MS m/z 347 [M–H]

PREPARATION 73

2-Chloro-4'-fluorobiphenyl-4-ol

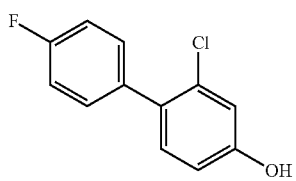 [SMILES: Oc1ccc(-c2ccc(F)cc2)c(Cl)c1]

4-Fluorobenzeneboronic acid (405 mg, 2.89 mmol) and 4-bromo-3-chlorophenol (500 mg, 2.41 mmol) were dissolved in dioxane (15 mL) and water (3 mL) under nitrogen. The solution was degassed before tetrakis(triphenylphosphine) palladium (0) (278 mg, 0.24 mmol) was added followed by caesium carbonate (2.36 g, 7.23 mmol) and the reaction was stirred at 80° C. for 18 hours. The cooled reaction mixture was partitioned between ethyl acetate and water. The aqueous layer was separated and extracted with ethyl acetate. The combined organic extracts were washed with brine, dried over MgSO$_4$, filtered and concentrated in vacuo. The residue was purified by silica gel column chromatography (20% ethyl acetate in heptane) to afford the title compound (503 mg, 94%) as a tan oil which solidified on standing.

$^1$HNMR (400 MHz, CDCl$_3$): δ 6.78 (d, 1H), 6.98 (s, 1H), 7.08 (dd, 2H), 7.18 (d, 1H), 7.38 (dd, 2H).

LCMS Rt=2.93 minutes MS m/z 221 [M–H]

PREPARATION 74

2-Chloro-2'-fluoro-5-(pyridazin-4-yl)biphenyl-4-ol

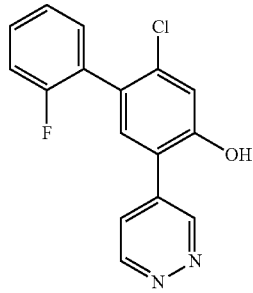 [SMILES: Oc1cc(Cl)c(-c2ccccc2F)cc1-c1ccnnc1]

2-Chloro-2'-fluoro-5-iodobiphenyl-4-ol (Preparation 75, 610 mg, 1.76 mmol) was dissolved in acetonitrile (3 mL) and 4-(tributylstannyl)pyridazine (843 mg, 2.28 mmol), caesium fluoride (533 mg, 3.51 mmol), copper iodide (67 mg, 0.35 mmol) and tetrakis(triphenylphosphine)palladium (0) (204 mg, 0.176 mmol) were added. The reaction was stirred at 80° C. for 18 hours and then the cooled reaction mixture was partitioned between ethyl acetate (100 mL) and water. The organic layer was separated and dried over MgSO$_4$, filtered and evaporated. The residue was chromatographed on silica gel eluting with heptane:ethyl acetate 1:1 to 100% ethyl acetate. Fractions containing product were evaporated and then triturated with dichloromethane to give the title compound (210 mg, 40%) as a yellow solid $^1$HNMR (400 MHz, CD$_3$OD): δ 7.26-7.15 (m, 3H), 7.45-7.33 (m, 2H), 7.48 (s, 1H), 8.00-7.98 (m, 1H), 9.17 (d, 1H), 9.51 (s, 1H).

$^{19}$FNMR (400 MHz, CD$_3$OD): δ –115.98

LCMS Rt=2.79 minutes, MS m/z 301 [MH]$^+$

PREPARATION 75

2-Chloro-2'-fluoro-5-iodobiphenyl-4-ol

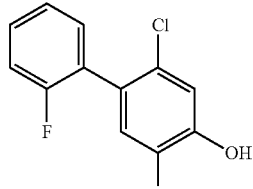

2-Chloro-2'-fluorobiphenyl-4-ol (Preparation 76, 430 mg, 1.93 mmol) was dissolved in DCM, and cooled to 0° C. Acetic acid (5 mL), N-iodosuccinimide (434 mg, 1.93 mmol) were added followed by concentrated sulphuric acid (0.2 mL). The reaction mixture was stirred at room temperature for 2 hours. The solvent was evaporated and the residue was purified by flash chromatography on silica gel eluting with heptane:ethyl acetate 7:3 to give the title compound (620 mg, 92%) as oil.

$^1$HNMR (400 MHz, CDCl$_3$): δ 5.37 (s, 1H), 7.29-7.11 (m, 4H), 7.40-7.35 (m, 1H) and 7.62 (s, 1H).
$^{19}$FNMR (400 MHz, CDCl$_3$): δ −114.01
LCMS Rt=3.40 minutes, MS m/z 347 [M−H]$^-$

PREPARATION 76

2-Chloro-2'-fluorobiphenyl-4-ol

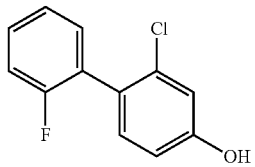 [SMILES: Oc1ccc(-c2ccccc2F)c(Cl)c1]

2-Fluorophenylboronic acid (0.405 g, 2.89 mmol) and 4-bromo-3-chlorophenol (0.500 g, 2.41 mmol) were dissolved in dioxane (10 mL). A solution of caesium carbonate (2.35 g, 7.21 mmol) in water (2 mL) was added and the reaction mixture was degassed. Tetrakis(triphenylphosphine) palladium (0) (0.280 g, 0.242 mmol) was added and reaction was further degassed before heating the reaction at 100° C. for 18 hours. The cooled reaction mixture was filtered through a pad of celite. The filtrate was diluted with EtOAc and washed with water and dried over MgSO$_4$, filtered and evaporated in vacuo. The residue was purified by flash chromatography on silica gel eluting with EtOAc/Heptane 2:3 to give the title compound (0.445 g, 69%) as dark solid $^1$HNMR (400 MHz, CDCl$_3$): δ 4.87 (s, 1H), 6.82-6.79 (m, 1H), 7.00 (s, 1H), 7.39-7.11 (m, 5H).
$^{19}$FNMR (400 MHz, CDCl$_3$): δ −114.28
LCMS Rt=3.09 minutes, MS m/z 221 [M−H]$^-$

PREPARATION 77 tert-Butyl {[4'-{2-cyano-4-[(1,3-thiazol-2-ylamino)sulfonyl]phenoxy}-3'-(1-methyl-1H-pyrazol-5-yl)biphenyl-3-yl]methyl}carbamate

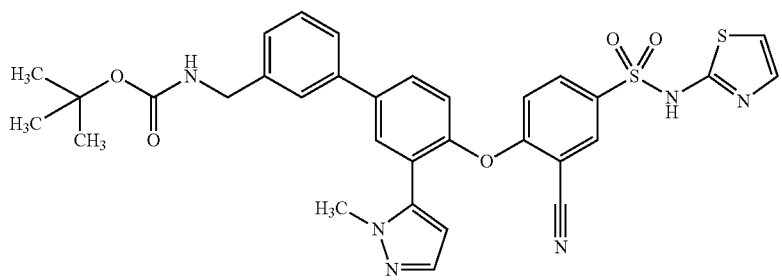 [SMILES: Cn1nccc1-c1cc(-c2cccc(CNC(=O)OC(C)(C)C)c2)ccc1Oc1ccc(S(=O)(=O)Nc2nccs2)cc1C#N]

In a 5 mL microwave vial 4-[4-bromo-2-(1-methyl-1H-pyrazol-5-yl)phenoxy]-3-cyano-N-1,3-thiazol-2-ylbenzene sulfonamide (Patent WO 2010079443, 500 mg, 0.97 mmol) was dissolved in 1,4-dioxane (3 mL) under nitrogen. (3-{[(Tert-butoxycarbonyl)amino]methyl}phenyl)boronic acid (362 mg, 1.44 mmol), bis(triphenylphosphine) palladium (II) dichloride (68 mg, 0.1 mmol), sodium carbonate (204 mg, 1.92 mmol) and water (0.5 mL) were added and the reaction vessel sealed and heated to 120° C. for 45 minutes in the microwave. The reaction mixture was partitioned between ethyl acetate (20 mL) and 0.2M aqueous HCl (20 mL). The organic layer was separated, filtered then concentrated in vacuo. The residue was purified by silica gel column chromatography (ISCO™, 12 g silica, 99:1 DCM:Acetic acid to 90:10:1 DCM:MeOH:Acetic acid gradient) to afford the title compound (380 mg, 61%) as a pale orange solid.

$^1$HNMR (400 MHz, CDCl$_3$): δ 1.46 (s, 9H), 3.88 (s, 3H), 5.29 (s, 2H), 6.24 (d, 1H), 6.59 (d, 1H), 6.73 (d, 1H), 7.08 (d, 1H), 7.27 (d, 1H), 7.32 (d, 1H), 7.38 (d, 1H), 7.45 (m, 1H) 7.50 (m, 2H) 7.64 (d, 1H) 7.72 (dd, 1H), 7.90 (dd, 1H), 8.09 (d, 1H), 9.40-10.20 (br s, 2H).
LCMS Rt=1.57 minutes MS m/z 643 [MH]$^+$.

PREPARATION 78

5-chloro-N-(2,4-dimethoxybenzyl)-2-fluoro-4-{2-pyridazin-4-yl-4-[2-(trifluoromethyl)pyridin-4-yl]phenoxy}-N-1,3,4-thiadiazol-2-ylbenzenesulfonamide

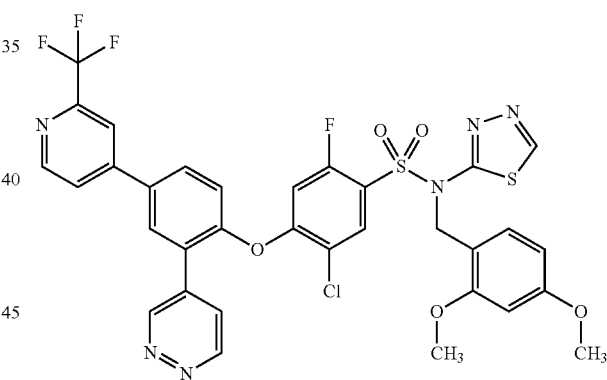

2-(Pyridazin-4-yl)-4-(2-(trifluoromethyl)pyridine-4-yl)phenol (Preparation 79, 0.105 mg, 0.33 mmol) was dissolved in DMSO (3 mL) and potassium carbonate (91 mg, 0.66 mmol) was added followed by 5-chloro-N-(2,4-dimethoxybenzyl)-2,4-difluoro-N-(1,3,4-thiadiazol-2-yl)benzensulfonamide (Preparation 16, 153 mg, 0.33 mmol). The mixture was stirred at room temperature for 3 hours and then partitioned between ethyl acetate (40 mL) and 1M aqueous sodium hydroxide solution (10 mL). The organic layer was separated and dried over Na$_2$SO$_4$, filtered and evaporated in vacuo. The residue was purified by silica gel column chromatography (ethyl acetate) to give the title compound (207 mg, 81%) as a beige solid.

$^1$HNMR (400 MHz, CDCl$_3$): δ 3.58 (s, 3H), 3.60 (s, 3H), 5.12 (s, 2H), 6.20 (d, 1H), 6.25 (d, 1H), 6.55 (d, 1H), 7.05 (d, 1H), 7.12 (m, 1H), 7.62 (m, 2H), 7.78 (m, 2H), 7.80 (d, 1H), 7.82 (s, 1H), 8.80 (m, 2H), 9.12 (d, 1H), 9.40 (s, 1H).

LCMS Rt=3.55 minutes, MS m/z 759 [MH]$^+$.

PREPARATION 79

2-(Pyridazin-4-yl)-4-(2-(trifluoromethyl)pyridine-4-yl)phenol

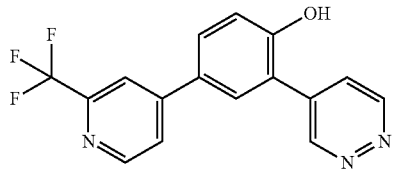 [SMILES: Oc1ccc(-c2ccnc(C(F)(F)F)c2)cc1-c1ccnnc1]

2-Iodo-4-(2-trifluoromethyl)pyridine-4-ylphenol (Preparation 80, 0.65 g, 1.8 mmol) was dissolved in acetonitrile (5 mL). 4-(tributylstannyl)pyridazine (0.90 g, 2.38 mmol) and caesium fluoride (0.53 g, 3.4 mmol) were added and the mixture was degassed for 10 minutes. Copper iodide (67 mg, 0.36 mmol) and tetrakistriphenylphosphinepalladium (0) (0.20 g, 0.18 mmol) were added and the mixture was heated at 50° C. for 18 hours. The cooled reaction mixture was concentrated in vacuo and the residue was purified by silica gel column chromatography eluting with a gradient of ethyl acetate:heptane 1:1 to 100% ethyl acetate to afford the title compound (102 mg, 19%).

$^1$HNMR (400 MHz, CD$_3$OD): δ 7.08 (d, 1H), 7.82 (d, 1H), 8.05 (m, 2H), 8.18 (m, 2H), 8.70 (d, 1H), 9.20 (d, 1H), 9.60 (s, 1H).

LCMS Rt=2.37 minutes, MS m/z 316 [M–H]–

PREPARATION 80

2-Iodo-4-(2-trifluoromethyl)pyridine-4-ylphenol

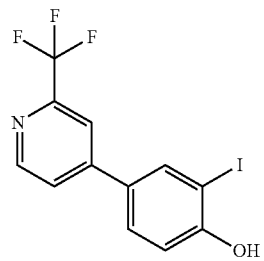 [SMILES: Oc1ccc(-c2ccnc(C(F)(F)F)c2)cc1I]

4-(2-Trifluoromethyl)pyridine-4-yl)phenol (Preparation 81, 3.60 g, 15 mmol) was dissolved in dichloromethane (200 mL) and acetic acid (60 mL). Concentrated sulphuric acid (2 mL) followed by N-iodosuccinimide (3.21 g, 14.2 mmol) were added. The reaction mixture was stirred for 18 hours at room temperature. The mixture was concentrated in vacuo and the residue was partitioned between ethyl acetate (200 mL) and water (100 mL). The organic layer was separated and concentrated in vacuo and the residue was purified by silica gel column chromatography (gradient 6% to 40% ethyl acetate in heptane) to afford a mixture (1.64 g) of the title compound and starting material which was used without further purification.

$^1$HNMR (400 MHz, CDCl$_3$): δ 5.15 (br s, 1H), 7.10 (d, 1H), 7.58 (m, 1H), 7.64 (m, 1H), 7.80 (s, 1H), 7.95 (s, 1H), 8.85 (m, 1H).

PREPARATION 81

4-(2-Trifluoromethyl)pyridine-4-ylphenol

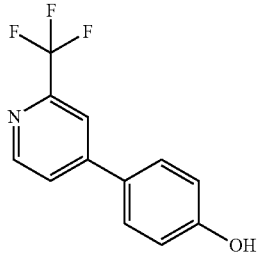 [SMILES: Oc1ccc(-c2ccnc(C(F)(F)F)c2)cc1]

4-Bromo-2-trifluoromethylpyridine (4 g, 17 mmol), 4-hydroxybenzene boronic acid (2.45 g, 17 mmol) and sodium carbonate (5.6 g, 52 mmol) were combined and dissolved in a mixture of dioxane/water (58 mL, 6:1). The reaction mixture was degassed and then tetrakistriphenylphosphinepalladium (0) (0.98 g, 0.85 mmol) was added and the reaction mixture was heated at 70° C. for 18 hours. The cooled reaction mixture was partitioned between ethyl acetate (100 mL) and water (50 mL). The organic layer was separated and dried over MgSO$_4$, filtered and concentrated in vacuo. The residue was purified by silica gel column chromatography (ethyl acetate:heptane 1:2) to provide the title compound (3.63 g, 84%) as a yellow solid.

$^1$HNMR (400 MHz, CDCl$_3$): δ 5.18 (s, 1H), 6.95 (d, 2H), 7.57 (m, 2H), 7.60 (d, 1H), 7.82 (s, 1H), 8.78 (d, 1H)

PREPARATION 82

5-chloro-N-(2,4-dimethoxybenzyl)-2-fluoro-4-{2-pyridazin-4-yl-4-[6-(trifluoromethyl)pyridin-2-yl]phenoxy}-N-1,3,4-thiadiazol-2-ylbenzenesulfonamide

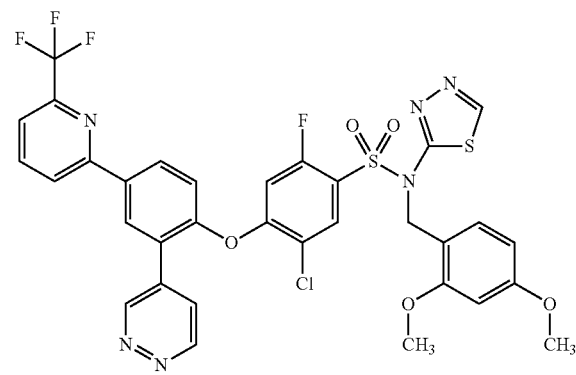 [SMILES: COc1ccc(CN(c2nncs2)S(=O)(=O)c2cc(Cl)c(Oc3ccc(-c4cccc(C(F)(F)F)n4)cc3-c3ccnnc3)cc2F)c(OC)c1]

2-(Pyridazin-4-yl)-4-(6-trifluoromethyl)pyridine-2-yl) phenol (Preparation 83, 75 mg, 0.23 mmol) was dissolved in DMSO (2 mL) and potassium carbonate (65 mg, 0.46 mmol) was added followed by 5-chloro-N-(2,4-dimethoxybenzyl)-2,4-difluoro-N-(1,3,4-thiadiazol-2-yl)benzenesulfonamide (Preparation 16, 109 mg, 0.23 mmol). The mixture was stirred at room temperature for 3 hours and then partitioned between ethyl acetate (40 mL) and 1M aqueous sodium hydroxide solution (10 mL). The organic layer was separated and dried over $Na_2SO_4$, filtered and evaporated. The residue was purified by silica gel column chromatography (1% methanol in dichloromethane) to give the title compound (52 mg, 29%) as a beige solid.

$^1$HNMR (400 MHz, $CDCl_3$): δ 3.60 (s, 3H), 3.65 (s, 3H), 5.25 (s, 2H), 6.08 (s, 1H), 6.25 (d, 1H), 6.42 (d, 1H), 7.05 (d, 1H), 7.10 (m, 1H), 7.45 (m, 1H), 7.78 (d, 1H), 7.90 (m, 2H), 8.08 (d, 1H), 8.12 (s, 1H), 8.88 (s, 2H), 9.10 (d, 1H), 9.20 (s, 1H).

LCMS Rt=3.10 minutes, MS m/z 759 [MH]$^+$.

PREPARATION 83

2-(Pyridazin-4-yl)-4-(6-trifluoromethyl)pyridine-2-ylphenol

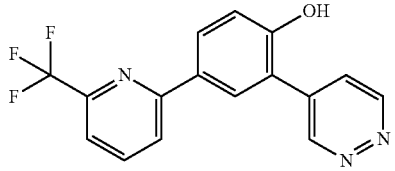 [SMILES: Oc1ccc(-c2cccc(C(F)(F)F)n2)cc1-c1ccnnc1]

2-Iodo-4-(6-trifluoromethyl)pyridin-2-ylphenol (Preparation 84, 0.25 g, 0.68 mmol) was dissolved in acetonitrile (5 mL), then 4-(tributylstannyl)pyridazine (0.30 g, 0.82 mmol) and caesium fluoride (0.20 g, 1.36 mmol) were added and the mixture was degassed. Copper iodide (67 mg, 0.36 mmol) and tetrakis(triphenylphosphine)palladium (0) (80 mg, 0.068 mmol) were added and the mixture was heated at 70° C. for 18 hours. The cooled reaction mixture was concentrated in vacuo and the residue was purified by silica gel column chromatography eluting with a gradient of ethyl acetate:heptane (1:1 to 100:0) to afford the title compound (100 mg, 46%).

$^1$HNMR (400 MHz, $CD_3OD$): δ 7.02 (d, 1H), 7.50 (d, 1H), 7.95 (m, 2H), 8.02 (m, 2H), 8.18 (m, 1H), 9.10 (br s, 1H), 9.50 (br s, 1H).

LCMS Rt=2.73 minutes, MS m/z 318 [MH]$^+$

PREPARATION 84

2-Iodo-4-(6-trifluoromethyl)pyridin-2-ylphenol

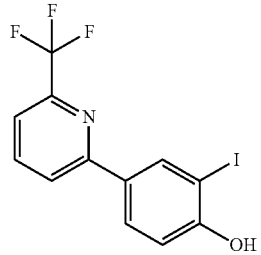 [SMILES: Oc1ccc(-c2cccc(C(F)(F)F)n2)cc1I]

4-(6-Trifluoromethyl)pyridine-2-yl)phenol (Preparation 85, 2.85 g, 12 mmol) was dissolved in dichloromethane (230 mL) and acetic acid (55 mL). Concentrated sulphuric acid (2 mL) was added followed by N-iodosuccinimide (2.41 g, 10.8 mmol). The reaction mixture was stirred for 18 hours at room temperature. The reaction mixture was concentrated in vacuo and the residue was partitioned between ethyl acetate (200 mL) and water (100 mL). The organic layer was separated, concentrated in vacuo and the residue was purified by silica gel column chromatography (gradient 6% to 40% ethyl acetate in heptane) to afford the title compound (2.16 g, 50%) as brown solid.

$^1$HNMR (400 MHz, $CDCl_3$): δ 5.25 (br s, 1H), 7.05 (d, 1H), 7.58 (d, 1H), 7.82 (m, 1H), 7.90 (m, 1H), 7.95 (m, 1H), 8.40 (s, 1H).

LCMS Rt=3.55 minutes, MS m/z 364 [M−H]

PREPARATION 85

4-(6-Trifluoromethyl)pyridine-2-yl)phenol

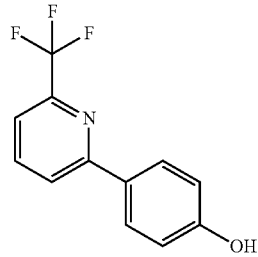 [SMILES: Oc1ccc(-c2cccc(C(F)(F)F)n2)cc1]

2-Bromo-6-trifluoromethylpyridine (3.5 g, 15.4 mmol), 4-hydroxybenzene boronic acid (2.12 g, 15.4 mmol) and sodium carbonate (4.2 g, 46 mmol) were dissolved in a 9:1 mixture of dioxane/water (120 mL) The reaction mixture was degassed and tetrakis(triphenylphosphine)palladium (0) (0.40 g, 0.35 mmol) was added. The reaction mixture was stirred at 80° C. for 18 hours. The cooled reaction mixture was partitioned between ethyl acetate (50 mL) and water (30 mL). The organic layer was separated and dried over $MgSO_4$, filtered and concentrated in vacuo. The residue was purified by silica gel chromatography (ethyl acetate:heptane 1:2) to provide the title compound (2.95 g, 79%) as a yellow solid.

$^1$HNMR (400 MHz, $CDCl_3$): δ 4.85 (br s, 1H), 6.85 (d, 2H), 7.45 (d, 1H), 7.78 (m, 1H), 7.80 (m, 1H), 7.98 (d, 2H).

LCMS Rt=2.98 minutes, MS m/z 240 [MH]$^+$.

PREPARATION 86

5-chloro-N-(2,4-dimethoxybenzyl)-2-fluoro-4-({3-[3-nitro-1-(tetrahydro-2H-pyran-2-yl)-1H-pyrazol-4-yl]-3'-(trifluoromethyl)biphenyl-4-yl}oxy)-N-1,3,4-thiadiazol-2-ylbenzenesulfonamide

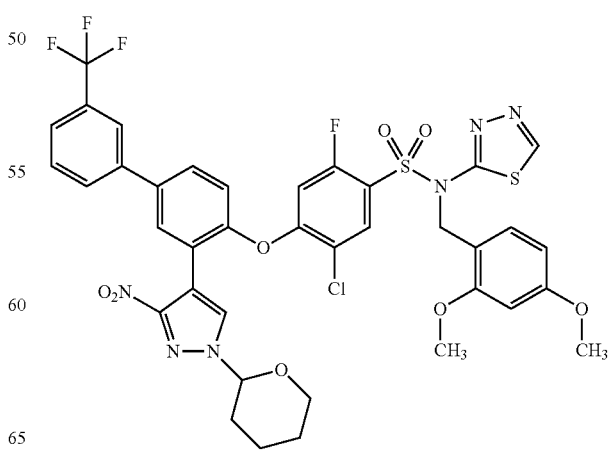

3-(3-Nitro-1-(tetrahydro-2H-pyran-2-yl)-1H-pyrazol-4-yl)-3'-(trifluoromethyl)biphenyl-4-ol (Preparation 87, 0.105 g, 0.24 mmol) was dissolved in DMSO (3 mL). 5-chloro-N-(2,4-dimethoxybenzyl)-2,4-difluoro-N-(1,3,4-thiadiazol-2-yl)benzene sulfonamide (Preparation 16, 0.11 g, 0.27 mmol) and potassium carbonate (35 mg, 0.25 mmol) were added and the mixture was stirred at room temperature for 18 hours. The reaction mixture was partitioned between ethyl acetate (40 mL) and water (10 mL). The organic layer was separated and dried over Na$_2$SO$_4$, filtered and evaporated. The residue was purified by silica gel chromatography eluting with a gradient of ethyl acetate:heptane 1:10 to 100% ethyl acetate to provide the title compound (0.15 g, 35%) as a white solid.

$^1$HNMR (400 MHz, CDCl$_3$): δ 1.82 (m, 3H), 1.95 (m, 2H), 2.10 (m, 1H), 3.62 (s, 3H), 3.68 (m, 1H), 3.70 (s, 3H), 3.95. (m, 1H), 4.20 (s, 2H), 5.40 (m, 1H), 6.18 (s, 1H), 6.30 (d, 1H), 6.48 (d, 1H), 7.05 (d, 1H), 7.20 (m, 2H), 7.55 (m, 1H), 7.60 (m, 2H), 7.70 (m, 2H), 7.76 (s, 2H), 8.78 (s, 1H).

LCMS Rt=3.50 minutes, MS m/z 875 [MH]$^+$.

PREPARATION 87

3-(3-Nitro-1-(tetrahydro-2H-pyran-2-yl)-1H-pyrazol-4-yl)-3'-(trifluoromethyl)biphenyl-4-ol

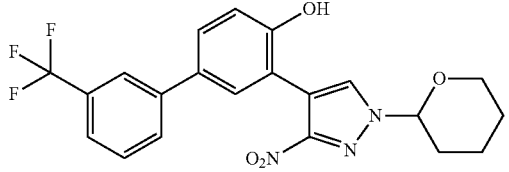 [SMILES: O=[N+]([O-])c1nn(C2CCCCO2)cc1-c1cc(-c2cccc(C(F)(F)F)c2)ccc1O]

A mixture of 3-iodo-3'-(trifluoromethyl)biphenyl-4-ol (Preparation 2, 0.5 g, 1.3 mmol), 3-nitro-1-(tetrahydro-2H-pyran-2-yl)-4-(4,4,5,5-tetramethyl-1,3,2-dioxaborolan-2-yl)-1H-pyrazole (0.42 g, 1.3 mmol), potassium fluoride (0.39 g, 0.65 mmol) in tetrahydrofuran (10 mL) was degassed. Bis-(tri-t-Butylphosphino)palladium (0) (35 mg, 0.068 mmol) was added and the reaction heated at 65° C. for 4 hours. After cooling the solvent was removed in vacuo and the residue was purified by silica gel chromatography (ethyl acetate:heptane 1:10) to provide the title compound (0.34 g, 61%) as a colourless oil.

$^1$HNMR (400 MHz, CDCl$_3$): δ 1.80 (m, 3H), 2.05 (m, 2H), 2.10 (m, 1H), 3.75 (m, 1H), 4.05 (m, 1H), 5.22 (m, 1H), 5.50. (br s, 1H), 6.90 (d, 1H), 7.45 (m, 4H), 7.62 (m, 1H), 7.70 (s, 1H), 7.78 (m, 1H).

$^{19}$FNMR (400 MHz, CDCl$_3$): δ −62

LCMS Rt=3.50 minutes, MS m/z 432 [M−H]$^-$

PREPARATION 88

4-[4-bromo-2-(1-methyl-1H-pyrazol-5-yl)phenoxy]-3-cyano-N-(2,4-dimethoxybenzyl)-N-1,3-thiazol-2-ylbenzenesulfonamide

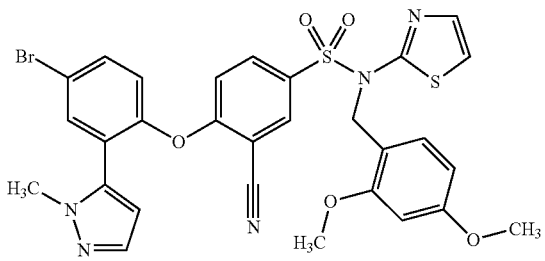 [SMILES: COc1ccc(CN(c2nccs2)S(=O)(=O)c2ccc(Oc3ccc(Br)cc3-c3ccnn3C)c(C#N)c2)c(OC)c1]

To a slurry of sodium hydride (54 mg, 1.4 mmol, 60% in mineral oil) in DMF (1 mL) was added 4-bromo-2-(1-methyl-1H-pyrazol-5-yl)phenol (Preparation 89, 210 mg, 0.83 mmol) as a solution in DMF (3 mL). After stirring for 30 minutes, 3-cyano-N-(2,4-dimethoxy-benzyl)-4-fluoro-N-thiazol-2-yl-benzenesulfonamide (Preparation 90, 415 mg, 0.957 mmol) was added. After 3 hours the reaction mixture was diluted with ethyl acetate (10 mL) and washed with water (5 mL) and brine (5 mL). The organic layer was dried over MgSO$_4$, filtered, and concentrated in vacuo. Purification by automated flash column chromatography using a 0-100% ethyl acetate/dichloromethane gradient provided the title compound (482 mg, 87%) as a yellow foam.

$^1$HNMR (400 MHz, d6-DMSO): δ 3.66 (s, 3H), 3.82 (s, 3H), 3.90 (s, 3H), 5.02 (m, 2H), 6.20 (m, 1H), 6.34 (m, 1H), 6.41 (m, 1H), 6.63 (m, 1H), 7.15 (m, 3H), 7.45 (m, 2H), 7.65 (m, 1H), 7.71 (m, 1H), 7.85 (m, 1H), 7.91 (m, 1H).

LCMS Rt=1.83 minutes; MS m/z 666 [MH]$^+$.

PREPARATION 89

4-Bromo-2-(1-methyl-1H-pyrazol-5-yl)phenol

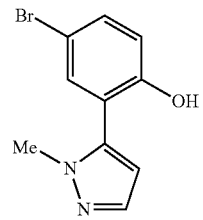

To a suspension of 6-bromochromone (1.58 g, 0.0070 mol) in ethanol (30 mL) was added methylhydrazine (0.41 mL, 0.0077 mol) and boron trifluoride etherate (1.15 mL, 0.0091 mol). The reaction was heated to reflux for 22 hours. After cooling, the reaction was concentrated in vacuo and the residue purified by automated flash column chromatography using a 0-100% ethyl acetate/hexanes gradient. This provided the title compound (0.79 g, 44%) as a light yellow solid.

$^1$HNMR (400 MHz, d6-DMSO): δ 3.70 (s, 3H), 6.30 (d, 1H), 6.96 (d, 1H), 7.36 (d, 1H), 7.47 (m, 2H), 10.28 (br s, 1H).

LCMS Rt=1.58 minutes MS m/z 253 [MH]$^+$.

PREPARATION 90

3-Cyano-N-(2,4-dimethoxybenzyl)-4-fluoro-N-1,3-thiazol-2-ylbenzenesulfonamide

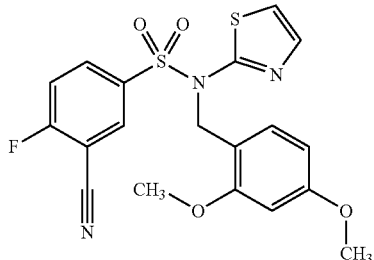

N-(2,4-Dimethoxybenzyl)-1,3-thiazol-2-yl-amine (Preparation 91, 8.010 g, 0.032 mol) was dissolved in tetrahydrofuran (100 mL) and the solution was cooled to −78° C. Lithium hexamethyldisilazide in tetrahydrofuran (35.2 mL, 1M) was added dropwise to the reaction mixture. The cooling bath was removed and the reaction mixture was allowed to stir for 30 minutes to attain room temperature before re-cooling to −78°

C. and a solution of 3-cyano-4-fluorobenzenesulfonyl chloride (7.028 g, 0.032 mol) in tetrahydrofuran (80 mL) was added dropwise to the reaction mixture. The reaction was allowed to stir 30 minutes at −78° C. before pouring it into saturated aqueous ammonium chloride (50 mL). The aqueous phase was separated and extracted with ethyl acetate (3×30 mL). The combined organic phases were washed twice with 10% aqueous citric acid solution (30 mL), water (30 mL), brine (20 mL), dried over MgSO$_4$, filtered and evaporated. The residue was purified by column chromatography (120 g silica gel column, hexanes/ethyl acetate gradient elution 100/0 to 0/100). Product fractions were combined and evaporated. The residue was triturated with 10% tert-butyl methyl ether in hexanes and the resulting off-white solid collected by filtration and rinsed with hexanes and vacuum dried to provide the title compound (3.58 g).

$^1$H NMR (400 MHz, d6-DMSO) δ 3.64 (s, 3H), 3.72 (s, 3H), 4.99 (s, 2H), 6.44 (dd, 1H), 6.48 (d, 1H), 7.05 (d, 1H), 7.50 (dd, 2H), 7.77 (t, 1H), 8.20 (m, 1H), 8.41 (dd, 1H).

LCMS Rt=1.66 minutes MS m/z 456 [MNa]$^+$.

PREPARATION 91

N-(2,4-Dimethoxybenzyl)-1,3-thiazol-2-amine

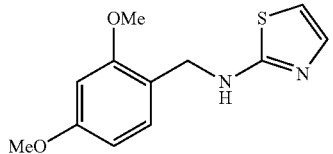 [SMILES: COc1ccc(CNc2nccs2)c(OC)c1]

2,4-Dimethoxybenzaldehyde (25 g, 150 mmol), 2-aminothiazole (15.1 g, 150 mmol) and piperidine (150 mg, 1.76 mmol) were combined in dichloroethane (500 ml) and the mixture was heated to reflux over 4 Å molecular sieves for 18 hours. The sieves were removed by filtration and the reaction mixture diluted with methanol (300 ml). Sodium borohydride (25 g, 662 mmol) was added in portions and the reaction mixture heated to reflux for 2 hours. The cooled reaction mixture was quenched with water (50 mL) and the organic solvents evaporated in vacuo. The aqueous residue was extracted with ethyl acetate (2×100 mL) and the combined organic solutions extracted with 2M HCl (2×50 mL). The acidic solution was basified with solid potassium carbonate and re-extracted with ethyl acetate (2×50 mL). The organic layer was dried over Na$_2$SO$_4$, filtered and evaporated in vacuo. The residue was purified by column chromatography eluting with 9:1 dichloromethane:methanol to yield the title compound (24 g, 96 mmol, 64%).

$^1$HNMR (300 MHz, CDCl$_3$): δ 3.80 (s, 3H), 3.83 (s, 3H), 4.38 (s, 2H), 5.1 (br s, 1H), 6.45 (m, 3H), 7.09 (d, 1H), 7.21 (d, 1H).

PREPARATION 92

5-Chloro-4-(6-chloro-2'-fluoro-4-(pyridazin-4-yl)biphenyl-3-yloxy)-N-(2,4-dimethoxybenzyl)-2-fluoro-N-(1,3,4-thiadiazol-2-yl)benzenesulfonamide

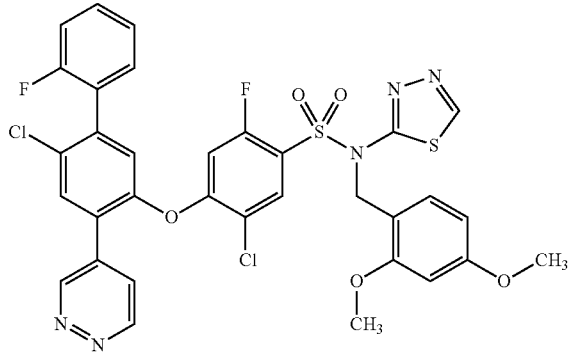 [SMILES: COc1ccc(CN(c2nncs2)S(=O)(=O)c2cc(Cl)c(Oc3cc(-c4ccccc4F)c(Cl)cc3-c3ccnnc3)cc2F)c(OC)c1]

Tetrakistriphenylphosphinepalladium (0) (44 mg, 0.038 mmol) and copper (I) iodide (29 mg, 0.152 mmol) were added to a degassed mixture of 5-chloro-4-(6-chloro-2'-fluoro-4-iodobiphenyl-3-yloxy)-N-(2,4-dimethoxybenzyl)-2-fluoro-N-(1,3,4-thiadiazol-2-yl)benzenesulfonamide (Preparation 93, 600 mg, 0.759 mmol), 4-(tributylstannyl)pyridazine (364 mg, 0.987 mmol), caesium fluoride (230 mg, 1.52 mmol), and acetonitrile (5.0 mL). The reaction was heated at 45° C. for 18 hours and then the cooled reaction mixture was diluted with ethyl acetate (30 mL) and filtered through Arbocel. The filtrate was then washed with water (5 mL), brine (5 mL), dried over MgSO$_4$, filtered and evaporated. The residue was purified by preparative HPLC using acetonitrile/water as eluent (15/85 to 95/5, Phenomenex Luna C18 5 u 110 A 21.2×150 mm) to give the title compound (220 mg, 39%) as a brown foam.

$^1$H-NMR (400 MHz, CDCl$_3$): δ 3.63 (s, 3H, OCH3), 3.68 (s, 3H, OCH3), 5.26 (s, 2H, NCH2), 6.16 (d, 1H, Ar), 6.29 (dd, 1H, Ar), 6.54 (d, 1H, Ar), 7.10 (s, 1H, Ar), 7.21 (m, 2H, Ar), 7.23 (m, 1H, Ar), 7.34 (m, 1H, Ar), 7.44 (m, 1H, Ar), 7.70 (m, 2H, Ar), 7.77 (d, 1H, Ar), 8.80 (s, 1H, Ar), 9.28 (dd, 1H, Ar), 9.45 (dd, 1H, Ar).

$^{19}$F-NMR (400 MHz, CDCl$_3$): δ −104.01, −114.04

LCMS (4.5 min) Rt=3.07 minutes, MS no mass ion seen.

PREPARATION 93

5-Chloro-4-(6-chloro-2'-fluoro-4-iodobiphenyl-3-yloxy)-N-(2,4-dimethoxybenzyl)-2-fluoro-N-(1,3,4-thiadiazol-2-yl)benzenesulfonamide

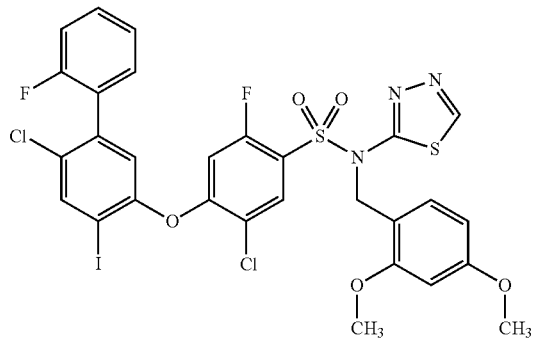 [SMILES: COc1ccc(CN(c2nncs2)S(=O)(=O)c2cc(Cl)c(Oc3cc(-c4ccccc4F)c(Cl)cc3I)cc2F)c(OC)c1]

6-Chloro-2'-fluoro-4-iodobiphenyl-3-ol (Preparation 94, 651 mg, 1.75 mmol) was added to a mixture of 5-chloro-N-(2,4-dimethoxybenzyl)-2,4-difluoro-N-(1,3,4-thiadiazol-2-yl)benzenesulfonamide (Preparation 16, 671 mg, 1.85 mmol) and potassium carbonate (967 mg, 7.00 mmol) in dimethylsulfoxide (17.5 mL) and the mixture stirred at room temperature for 18 hours. The reaction was quenched by addition of 0.75 N aq. sodium hydroxide (30.0 mL) and ethyl acetate (30 mL). The aqueous layer was separated and extracted with ethyl acetate (3×10 mL). The combined organic phases were washed with brine (10 mL), dried over MgSO$_4$, filtered and evaporated. The residue was purified on silica, eluting with ethyl acetate:heptanes (3:7) to give the title compound as a mixture of regioisomers (930 mg, 67%). Further purification by preparative HPLC using acetonitrile/water as eluent (5/95-95/5, Phenomenex Luna C18 5 u 110 A 21.2×150 mm) gave the title compound (600 mg, 43%) as a white solid.

$^1$H-NMR (400 MHz, CDCl$_3$): δ 3.68 (s, 3H), 3.71 (s, 3H), 5.33 (s, 2H), 6.24 (d, 1H), 6.32 (dd, 1H), 6.39 (d, 1H), 7.02 (s, 1H), 7.16 (m, 1H), 7.24 (m, 1H), 7.26 (m, 1H), 7.29 (m, 1H), 7.42 (m, 1H), 7.83 (d, 1H), 8.03 (s, 1H), 8.81 (s, 1H).

$^{19}$F-NMR (400 MHz, CDCl$_3$): δ −104.48, −113.97

LCMS (4.5 min) Rt=4.20 minutes, MS no mass ion seen.

PREPARATION 94

6-Chloro-2'-fluoro-4-iodobiphenyl-3-ol

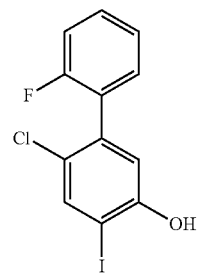 [SMILES: Oc1cc(-c2ccccc2F)c(Cl)cc1I]

Boron tribromide (251 mg, 2.61 mmol) was added to a solution of 2-chloro-2'-fluoro-4-iodo-5-methoxybiphenyl (Preparation 95, 671 mg, 1.85 mmol) in dichloromethane (4.7 mL) at −20° C. and the mixture allowed to warm slowly to room temperature for 18 hours. The reaction was quenched by addition of water (10.0 mL), before being diluted with dichloromethane (30 mL). The organic phase was separated and washed with water (3×5.0 mL), brine (5.0 mL), dried over $MgSO_4$, filtered and evaporated to give a purple oil. Column chromatography purification on silica, eluting with 1:4 ethyl acetate:heptanes gave the title compound (610 mg, 94%) as a colourless oil.

$^1$H-NMR (400 MHz, $CDCl_3$): δ 6.97 (s, 1H, Ar), 7.15 (t, 1H, Ar), 7.22 (m, 1H, Ar), 7.28 (m, 1H, Ar), 7.39 (m, 1H, Ar), 7.76 (s, 1H, Ar), $^{19}$F-NMR (400 MHz, $CDCl_3$): δ −114.03

LCMS (4.5 min) Rt=3.44 minutes, MS m/z 347 [M−H]$^-$

PREPARATION 95

2-Chloro-2'-fluoro-4-iodo-5-methoxybiphenyl

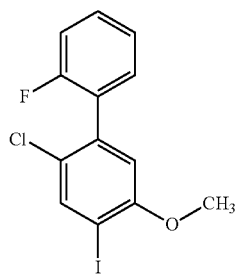 [SMILES: COc1cc(-c2ccccc2F)c(Cl)cc1I]

N-Iodosuccinimide (683 mg, 3.04 mmol) was added to a solution of 2-chloro-2'-fluoro-5-methoxybiphenyl (Preparation 96, 749 mg, 3.16 mmol) in concentrated sulfuric acid (0.09 mL), acetic acid (4.7 mL) and dichloromethane (4.7 mL). The resulting mixture was stirred at room temperature for 18 hours and then partitioned between dichloromethane (30 mL) and water (5 mL). The organic phase was separated and washed with water (2×5 mL), brine (5 mL), dried over $MgSO_4$, filtered and evaporated to give a red oil. Column chromatography purification on silica, eluting with dichloromethane:heptanes (1:9) gave the title compound (671 mg, 58%) as a colourless oil.

$^1$H-NMR (400 MHz, $CDCl_3$): δ 3.86 (s, 3H, OMe), 6.75 (s, 1H, Ar), 7.16 (t, 1H, Ar), 7.22 (m, 1H, Ar), 7.32 (m, 1H, Ar), 7.41 (m, 1H, Ar), 7.88 (s, 1H, Ar), $^{19}$F-NMR (400 MHz, $CDCl_3$): δ −114.02

LCMS (4.5 min) Rt=3.88 minutes, No mass ion seen

PREPARATION 96

2-Chloro-2'-fluoro-5-methoxybiphenyl

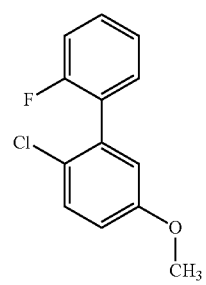 [SMILES: COc1ccc(Cl)c(-c2ccccc2F)c1]

Tetrakistriphenylphosphinepalladium (0) (229 mg, 0.20 mmol) was added to a degassed mixture of 2-fluorophenylboronic acid (556 mg, 3.97 mmol), 2-bromo-1-chloro-4-methoxybenzene (0.49 mL, 3.57 mmol), caesium carbonate (3.87 g, 11.9 mmol), water (5.0 mL) and dioxane (26.0 mL). The reaction was heated at 80° C. for 18 hours, cooled to room temperature and then partitioned between ethyl acetate (30.0 mL) and sat. aq. ammonium chloride (10.0 mL). The aqueous phase was separated and extracted with ethyl acetate (2×10 mL). The combined organic phases were washed with brine (5.0 mL), dried over $MgSO_4$, filtered and evaporated to give a pale yellow oil. Column chromatography purification on silica, eluting with heptanes gave the title compound (749 mg, 88%) as a colourless oil.

$^1$HNMR (400 MHz, $CDCl_3$): δ 3.81 (s, 3H, OMe), 6.87-6.89 (m, 2H, Ar), 7.15 (m, 1H, Ar), 7.21 (m, 1H, Ar), 7.31-7.41 (m, 3H, Ar).

LCMS (4.5 min) Rt=3.00 minutes, No mass ion seen.

PREPARATION 97

5-Chloro-4-(6-chloro-3'-fluoro-4-(pyridazin-4-yl)biphenyl-3-yloxy)-N-(2,4-dimethoxybenzyl)-2-fluoro-N-(1,3,4-thiadiazol-2-yl)benzenesulfonamide

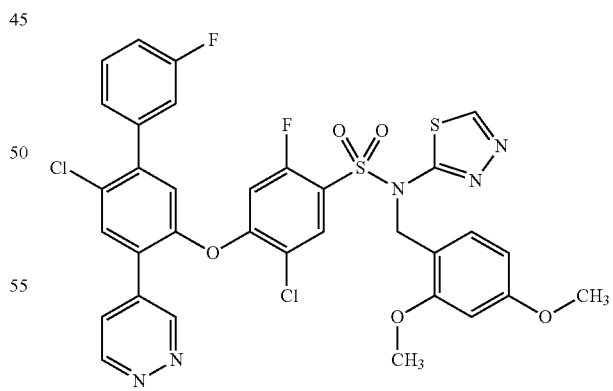

5-Chloro-N-(2,4-dimethoxybenzyl)-2,4-difluoro-N-(1,3,4-thiadiazol-2-yl)benzenesulfonamide (Preparation 16, 136 mg, 0.29 mmol) was added to a solution of 6-chloro-3'-fluoro-4-(pyridazin-4-yl)biphenyl-3-ol (Preparation 98, 133 mg, 0.29 mmol) and potassium carbonate (183 mg, 0.88 mmol) in dimethylsulfoxide (5 mL). The reaction mixture was stirred at room temperature for 18 hours. The reaction mixture was diluted with sodium hydroxide (1M, 5 mL) and extracted with ethyl acetate (3×10 mL). The combined organic layers were dried over MgSO4, filtered and concentrated in vacuo. The residue was dissolved in dimethylsulfoxide:acetonitrile (2.5 mL: 1.5 mL) and then purified on the reverse phase HPLC eluting with acetonitrile:water (from 5:95 to 95:5, 30 minutes gradient then 5 minutes isocratic) to give the title compound (60 mg, 18%) as a white solid.

$^{1}$H NMR (400 MHz, CDCl$_{3}$): δ 3.64 (s, 3H), 3.71 (s, 3H), 5.23 (s, 2H), 6.20 (d, 1H), 6.31 (dd, 1H), 6.52 (d, 1H), 7.08 (s, 1H), 7.13-7.23 (m, 4H), 7.43-7.48 (m, 1H), 7.69-7.71 (m, 2H), 7.80 (d, 1H), 8.80 (s, 1H), 9.28-9.30 (m, 1H), 9.44-9.45 (m, 1H).

$^{19}$F NMR (400 MHz, CDCl$_{3}$): δ −104, −112.

LCMS (4.5 min acidic run) Rt=3.16 minutes, MS m/z 742 [MH]$^{+}$.

PREPARATION 98

6-Chloro-3'-fluoro-4-(pyridazin-4-yl)biphenyl-3-ol

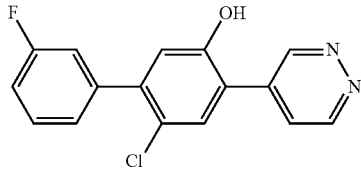 [SMILES: Oc1cc(-c2cccc(F)c2)c(Cl)cc1-c1ccnnc1]

Caesium fluoride (219 mg, 1.44 mmol) was added to a solution of 6-chloro-3'-fluoro-4-iodobiphenyl-3-ol (Preparation 99, 251 mg, 0.72 mmol) and 4-(tributylstannyl)pyridazine (345 mg, 0.93 mmol) in acetonitrile (5 mL). The reaction mixture was degassed and copper iodide (28 mg, 0.15 mmol) and tetrakistriphenylphosphinepalladium (0) (83 mg, 0.07 mmol) were added. The reaction mixture was stirred at 80° C. for 3 hours. The cooled reaction mixture was diluted with ethyl acetate (20 mL) and quenched with a solution of ammonia (10%, 10 mL) and stirred for a further 10 minutes. The organic layer was separated and washed with brine (1×10 mL), dried over MgSO$_{4}$, filtered and concentrated in vacuo. The residue was purified using silica gel chromatography (Biotage) eluting with heptane:ethyl acetate (93:7 to 0:100) to give the title compound (185 mg, 62%) as a yellow solid.

$^{1}$H NMR (400 MHz, d6-DMSO): δ 7.01 (s, 1H), 7.26-7.30 (m, 3H), 7.58-7.60 (m, 1H), 7.72 (s, 1H), 7.94-7.96 (m, 1H), 9.25-9.27 (m, 1H), 9.52-9.53 (m, 1H).

LCMS (4.5 min acidic run) Rt=2.88 minutes, MS m/z 301 [MH]$^{+}$.

PREPARATION 99

6-Chloro-3'-fluoro-4-iodobiphenyl-3-ol

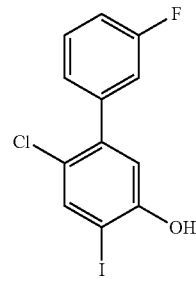 [SMILES: Oc1cc(-c2cccc(F)c2)c(Cl)cc1I]

N-Iodosuccinimide (261 mg, 1.16 mmol) was added to a mixture of 6-chloro-3'-fluorobiphenyl-3-ol (Preparation 100, 270 mg, 1.21 mmol) and concentrated sulphuric acid (24 μL, 0.43 mmol) in acetic acid (3 mL) and dichloromethane (3 mL). The reaction mixture was stirred at room temperature for 1.5 hours. The reaction mixture was diluted with dichloromethane (10 mL) and washed with sodium metabisulfite (0.5M, 10 mL), dried over MgSO$_{4}$, filtered and concentrated in vacuo. The residue was purified by flash chromatography eluting with heptane:dichloromethane (70:30) to give the title compound (193 mg, 46%) as a pale yellow solid.

$^{1}$H NMR (400 MHz, CDCl$_{3}$): δ 5.28 (br-s, 1H), 6.99-7.12 (m, 3H), 7.29-7.35 (m, 1H), 7.68 (s, 1H).

$^{19}$F NMR (400 MHz, CDCl$_{3}$): δ −113.

LCMS (4.5 min acidic run) Rt=3.51 minutes, MS m/z 347 [M−H]

PREPARATION 100

6-Chloro-3'-fluorobiphenyl-3-ol

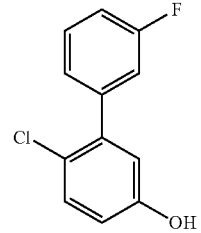 [SMILES: Oc1ccc(Cl)c(-c2cccc(F)c2)c1]

Caesium carbonate (1.15 g, 3.53 mmol) was added to a solution of 4-chloro-3-iodophenol (300 mg, 2.14 mmol) and 3-fluorophenylboronic acid (330 mg, 1.30 mmol) in dioxane:water (22.5 mL:4.5 mL). The reaction mixture was degassed and tetrakistriphenylphosphine palladium (0) (69 mg, 0.06 mmol) was added. The reaction mixture was stirred at 70° C. for 5 hours. The cooled reaction mixture was concentrated in vacuo and the aqueous residue was extracted with ethyl acetate (3×10 mL). The combined organic layers were dried over MgSO$_{4}$, filtered and concentrated in vacuo. The residue was purified on the biotage eluting with heptane:ethyl acetate (from 98:2 to 80:20) to give the title compound (270 mg, 100%) as a yellow solid.

$^{1}$H NMR (400 MHz, CDCl$_{3}$): δ 6.00 (br-s, 1H), 6.76-6.82 (m, 2H), 7.04-7.11 (m, 1H), 7.12-7.17 (m, 1H), 7.18-7.21 (m, 1H), 7.32 (d, 1H), 7.36-7.42 (m, 1H).

$^{19}$F NMR (400 MHz, CDCl$_{3}$): δ −114.

LCMS (4.5 min acidic run) Rt=3.16 minutes, MS m/z 221 [M−H]$^{-}$

PREPARATION 101

5-Chloro-4-(6-chloro-4'-fluoro-4-(pyridazin-4-yl)biphenyl-3-yloxy)-N-(2,4-dimethoxybenzyl)-2-fluoro-N-(1,3,4-thiadiazol-2-yl)benzenesulfonamide

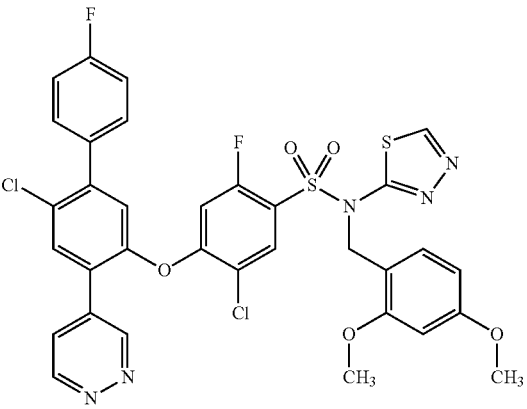 [SMILES: COc1ccc(CN(c2nncs2)S(=O)(=O)c2cc(Cl)c(Oc3cc(-c4ccc(F)cc4)c(Cl)cc3-c3ccnnc3)cc2F)c(OC)c1]

6-Chloro-4'-fluoro-4-(pyridazin-4-yl)biphenyl-3-ol (Preparation 102, 150 mg, 0.50 mmol), 5-chloro-N-(2,4-dimethoxybenzyl)-2,4-difluoro-N-(1,3,4-thiadiazol-2-yl)benzenesulfonamide (Preparation 16, 345 mg, 0.75 mmol), and potassium carbonate (207 mg, 1.50 mmol) were suspended in dimethyl sulfoxide (2 mL). The reaction mixture was stirred for 18 hours at room temperature. Water (50 mL) was added and the suspension was extracted with ethyl acetate (2×50 mL) and dichloromethane (3×50 mL). The organic layers were combined, dried over MgSO$_4$, filtered and evaporated. The residue was purified by semi preparative reverse phase HPLC (solvent A: 0.05% formic acid in acetonitrile; solvent B: 0.05% formic acid in water; flow rate: 15 mL/min; gradient 0 min 5% A, 2.5 min 5% A, 22.5 min 95% A, 32.5 min 95% A then return to initial conditions) to afford the title compound (100 mg, 27%) as a glass.

$^1$H NMR (400 MHz, CDCl$_3$): δ 3.64 (s, 3H), 3.71 (s, 3H), 5.25 (s, 2H), 6.20 (m, 1H), 6.31 (m, 1H), 6.52 (m, 1H), 7.07 (s, 1H), 7.18 (m, 3H), 7.44 (m, 2H), 7.70 (s, 1H), 7.74 (m, 1H), 7.80 (m, 1H), 8.81 (s, 1H), 9.29 (m, 1H), 9.46 (m, 1H).

$^{19}$F NMR (400 MHz, CDCl$_3$): δ −104.0, −112.2

LCMS Rt=3.46 min MS m/z 742 [MH]$^+$.

PREPARATION 102

6-Chloro-4'-fluoro-4-(pyridazin-4-yl)biphenyl-3-ol

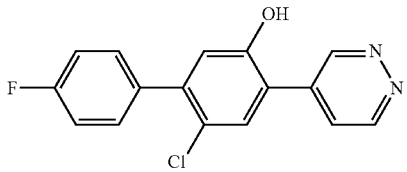

A suspension of 6-chloro-4'-fluoro-4-iodobiphenyl-3-ol (Preparation 103, 300 mg, 0.86 mmol), 4-(tributylstannyl)pyridazine (413 mg, 1.12 mmol), caesium fluoride (261 mg, 1.72 mmol), and copper (I) iodide (33 mg, 0.17 mmol) in acetonitrile (5 mL) was degassed for 20 minutes under nitrogen. Tetrakistriphenylphosphinepalladium (0) (100 mg, 0.09 mmol) was added and the reaction mixture was heated for 18 hours at 45° C. under nitrogen. The cooled reaction mixture was filtered through Arbocel and the Arbocel pad was washed with ethyl acetate (100 mL). The organic layer was washed with brine (2×15 mL), dried over MgSO$_4$, filtered and evaporated. The residue was purified by silica gel chromatography eluting with 20% heptane in ethyl acetate to afford the title compound (150 mg, 58%) as an oil.

$^1$H NMR (400 MHz, CDCl$_3$): δ 6.98 (s, 1H), 7.20 (m, 2H), 7.48 (m, 2H), 7.67 (s, 1H), 8.04 (m, 1H), 9.20 (m, 1H), 9.56 (m, 1H).

$^{19}$F NMR (400 MHz, CDCl$_3$): δ −116.2

LCMS Rt=2.85 min MS m/z 299 [M−H]

PREPARATION 103

6-Chloro-4'-fluoro-4-iodobiphenyl-3-ol

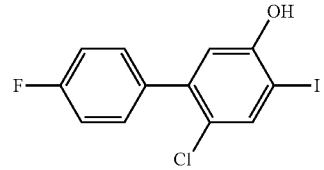 [SMILES: Oc1cc(-c2ccc(F)cc2)c(Cl)cc1I]

To a solution of 6-chloro-4'-fluorobiphenyl-3-ol (Preparation 104, 280 mg, 1.26 mmol) in acetic acid (2.5 mL), dichloromethane (2.5 mL) and concentrated sulfuric acid (25 μL) was added N-iodosuccinimide (272 mg, 1.21 mmol) at room temperature. The reaction mixture was stirred for 18 hours at room temperature. Dichloromethane (60 mL) was added and the organic layer was washed with brine (2×20 mL), dried over MgSO$_4$, filtered and evaporated. The residue was purified by silica gel chromatography eluting 33% dichloromethane in heptane to afford the title compound (306 mg, 70%) as a colourless oil.

$^1$H NMR (400 MHz, CDCl$_3$): δ 5.27 (s, 1H), 6.96 (s, 1H), 7.12 (m, 2H), 7.38 (m, 2H), 7.75 (s, 1H).

$^{19}$F NMR (400 MHz, CDCl$_3$): δ −113.8

LCMS Rt=3.52 min MS m/z 347 [M−H]

PREPARATION 104

6-Chloro-4'-fluorobiphenyl-3-ol

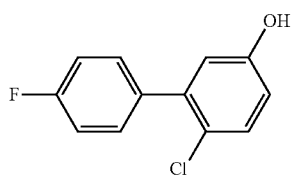 [SMILES: Oc1ccc(Cl)c(-c2ccc(F)cc2)c1]

A solution of 4-fluorophenylboronic acid (500 mg, 3.57 mmol), 4-chloro-3-iodophenol (455 mg, 1.79 mmol) and caesium carbonate (1.75 g) in dioxane (10 mL) and water (5 mL) was degassed 1 hour with nitrogen. Tetrakis(triphenylphosphine)palladium (0) (104 mg, 0.09 mmol) was added and the reaction mixture was heated for 18 hours at 75° C. The cooled reaction mixture was concentrated in vacuo and the residual aqueous layer was extracted with ethyl acetate (3×50 mL). The combined organic layer were dried over MgSO$_4$, filtered and evaporated. The residue was purified by silica gel chromatography eluting with 20% ethyl acetate in heptane to afford the title compound (280 mg, 70%) as a yellow oil.

$^1$H NMR (400 MHz, CDCl$_3$): δ 4.85 (s, 1H), 6.79 (m, 2H), 7.11 (m, 2H), 7.31 (m, 1H), 7.40 (m, 2H).

$^{19}$F NMR (400 MHz, CDCl$_3$): δ −114.0

LCMS Rt=2.96 min MS m/z 221 [M−H]

PREPARATION 105

5-Chloro-N-(2,4-dimethoxybenzyl)-2,4-difluoro-N-(5-fluoropyridin-2-yl)benzenesulfonamide

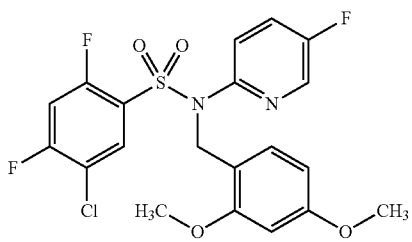 [SMILES: COc1ccc(CN(c2ccc(F)cn2)S(=O)(=O)c2cc(Cl)c(F)cc2F)c(OC)c1]

5-Chloro-2,4-difluorobenzenesulfonyl chloride (200 mg, 0.81 mmol), N-(2,4-dimethoxybenzyl)-5-fluoropyridin-2-amine (Preparation 106, 255 mg, 0.97 mmol) and pyridine (196 µL, 2.43 mmol) in dichloromethane (3 mL) were stirred at room temperature for 36 hours. The mixture was evaporated in vacuo and the residue was purified by silica gel column chromatography (5 g Varian bond-elut cartridge, heptane/ethyl acetate 100/0 to 70/30) to afford the title compound (193 mg) as a gum.

$^1$H NMR (400 MHz, CDCl$_3$) δ ppm 3.68 (s, 3 H), 3.76 (s, 3 H), 4.99 (s, 2 H), 6.31-6.37 (m, 2H), 6.96-7.05 (m, 1 H), 7.16 (d, 1 H), 7.29-7.36 (m, 2 H), 7.89 (dd, 1 H), 8.15-8.18 (m, 1 H).

LCMS Rt=1.74 minutes, MS no mass ion seen.

PREPARATION 106

N-(2,4-Dimethoxybenzyl)-5-fluoropyridin-2-amine

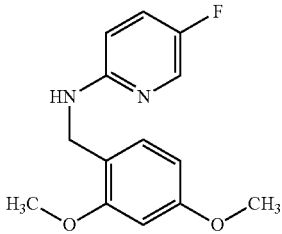

5-Fluoropyridin-2-amine (500 mg, 4.46 mmol) and 2,4-dimethoxybenzaldehyde (674 mg, 4.06 mmol) were stirred in dichloromethane (10 mL) at room temperature for 30 minutes. Sodium triacetoxyborohydride (1.3 g, 6.08 mmol) was added portion wise. The mixture was then stirred at room temperature for 18 hours before treatment with 1M aqueous sodium hydroxide solution (10 mL). The aqueous layer was separated and extracted with dichloromethane (10 mL). The combined organic layers were dried through a phase separating cartridge and evaporated to afford the title compound (1.2 g) as a brown solid.

$^1$H NMR (400 MHz, CDCl$_3$) δ 3.80 (s, 3 H), 3.84 (s, 3 H), 4.38 (d, 2 H), 4.84 (br. s., 1 H), 6.35 (dd, 1 H), 6.43 (dd, 2.34 Hz, 1 H), 6.48 (d, 1 H), 7.12-7.22 (m, 2 H), 7.96 (d, 1 H).

LCMS Rt=2.07 minutes, MS m/z 263 [MH]$^+$.

PREPARATION 107

3-(1-Methyl-1H-pyrazol-5-yl)biphenyl-4-ol

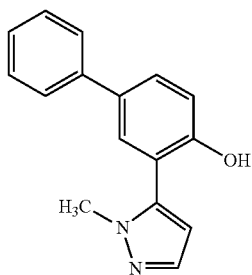 [SMILES: Cn1nccc1-c1cc(-c2ccccc2)ccc1O]

To a stirred suspension of 5-[4-(benzyloxy)biphenyl-3-yl]-1-methyl-1H-pyrazole (Preparation 108, 3 g, 8.81 mmol) in methanol (26 mL) was added palladium on carbon (300 mg). The mixture was stirred at room temperature under a hydrogen atmosphere for 16 hours before filtering through a Celite™ pad. The pad was washed with tetrahydrofuran and the filtrate was evaporated in vacuo. The residue was dissolved in ethyl acetate (26 mL) and the solution degassed with argon. Palladium on carbon (300 mg) was added and the mixture was stirred at room temperature under a hydrogen atmosphere for 6 hours. The catalyst was filtered off through a Celite pad and the filtrate was evaporated in vacuo. Trituration of the residue with n-hexane afforded the title compound (1.95 g) as a white solid.

$^1$H NMR (400 MHz, d-6DMSO) δ 3.89 (s, 3H), 6.30 (d, 1H), 7.06 (d, 1H), 7.29 (t, 1H), 7.38-7.46 (m, 4H), 7.56-7.64 (m, 3H), 10.14 (br. s, 1H).

LCMS Rt=3.29 minutes, MS m/z 251 [MH]+.

PREPARATION 108

5-[4-(Benzyloxy)biphenyl-3-yl]-1-methyl-1H-pyrazole

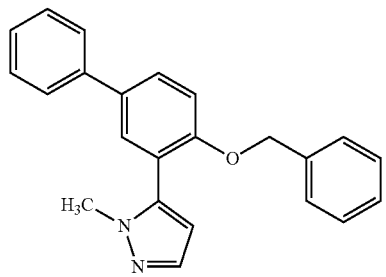 [SMILES: Cn1nccc1-c1cc(-c2ccccc2)ccc1OCc1ccccc1]

A solution of benzyl 3-bromobiphenyl-4-yl ether (500 mg, 1.47 mmol) and (1-methyl-1H-pyrazol-5-yl)boronic acid (185 mg, 1.47 mmol) in dioxane (4 mL) was degassed with argon for 30 minutes. Tris(dibenzylideneacetone)dipalladium (0) (54 mg, 0.06 mmol) and tricyclohexylphosphine (33 mg, 0.12 mmol) were added to the mixture under an argon atmosphere. A degassed solution of tripotassium phosphate (626 mg, 2.95 mmol) in water (2 mL) was added and the mixture was stirred at reflux for 16 hours under an argon atmosphere. The cooled reaction mixture was filtered through a pad of Celite and the filtrate evaporated in vacuo. The residue was dissolved in ethyl acetate (25 mL) and the solution was washed with water (2×10 mL), brine (10 mL), dried over Na$_2$SO$_4$, filtered and evaporated. The residue was purified by silica gel column chromatography (10% ethyl acetate in hexane) to afforded the title compound (320 mg).

$^1$H NMR (400 MHz, d-6DMSO) δ 3.67 (s, 3H), 5.21 (s, 2H), 6.35 (d, 1H), 7.27-7.45 (m, 10H), 7.56 (d, 1H), 7.65-7.69 (m, 2H), 7.72-7.77 (m, 1H).

LCMS Rt=2.21 minutes, MS m/z 341 [MH]$^+$.

PREPARATION 109 tert-butyl 4-{4-[4-(2-chloro-4-{[(2,4-dimethoxybenzyl)(pyrimidin-4-yl)amino]sulfonyl}-5-fluorophenoxy)-4'-(trifluoromethyl)biphenyl-3-yl]pyridin-2-yl}piperazine-1-carboxylate

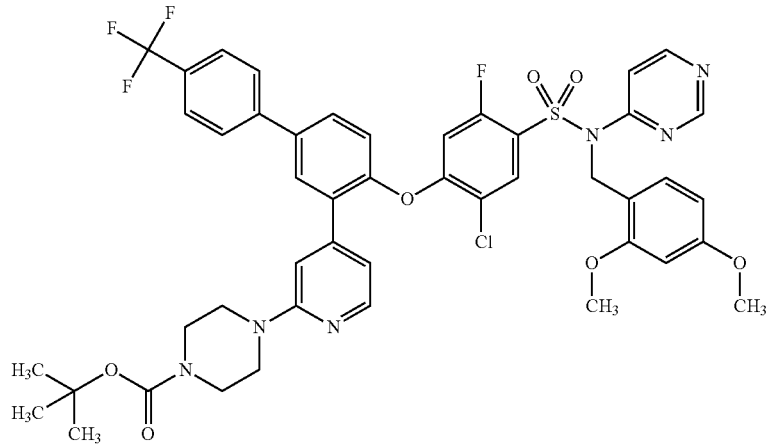

To a solution of tert-butyl 4-(4-(4-hydroxy-4'-(trifluoromethyl)biphenyl-3-yl)pyridin-2-yl)piperazine-1-carboxylate (Preparation 114, 200 mg, 0.401 mmol) in dimethyl sulfoxide (5 mL) was added potassium carbonate (111 mg, 0.802 mmol) followed by 5-chloro-N-(2,4-dimethoxybenzyl)-2,4-difluoro-N-(pyrimidin-4-yl)benzenesulfonamide (Preparation 110, 182 mg, 0.401 mmol). The reaction mixture was stirred at room temperature for 2 hours and then partitioned between ethyl acetate (20 mL) and water (10 mL). The organic layer was separated, dried over anhydrous MgSO$_4$, filtered and evaporated. The residue was purified by flash chromatography on silica gel eluting with 30% heptane in ethyl acetate to give the title compound (320 mg, 85%) as yellow foam.

$^1$HNMR (400 MHz, CDCl$_3$): δ 1.49 (s, 9H), 3.55 (br s, 8H), 3.75 (s, 3H), 3.77 (s, 3H), 5.18 (s, 2H), 6.42-6.36 (m, 3H), 6.75 (d, 1H), 6.82 (s, 1H), 7.23-7.16 (m, 3H), 7.75-7.66 (m, 6H), 8.02 (d, 1H), 8.16 (d, 1H), 8.46 (d, 1H), 8.79 (s, 1H)
$^{19}$FNMR (376 MHz, CDCl$_3$): δ −106.76 (F), −62.55 (CF3) LCMS Rt=4.49 minutes, m/z 935 [MH]$^+$.

PREPARATION 110

5-Chloro-N-(2,4-dimethoxybenzyl)-2,4-difluoro-N-(pyrimidin-4-yl)benzenesulfonamide

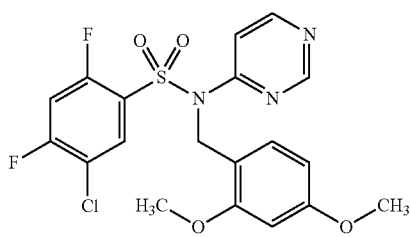 [SMILES: COc1ccc(CN(c2ccncn2)S(=O)(=O)c2cc(Cl)c(F)cc2F)c(OC)c1]

N-(2,4-Dimethoxybenzyl)pyrimidin-4-amine (Preparation 111, 1.80 g, 7.35 mmol), 5-chloro-2,4-difluorobenzene-1-sulfonyl chloride (1.81 g, 7.35 mmol) and 1,4-diazabicyclo[2.2.2]octane (0.82 g, 7.35 mmol) in acetonitrile (50 mL) were stirred at room temperature for 18 hours. The reaction mixture was concentrated in vacuo and the residue was partitioned between dichloromethane (30 mL) and water (15 mL). The organic layer was separated and dried over anhydrous MgSO$_4$, filtered and evaporated. The residue was purified by flash chromatography on silica gel eluting with 10% dichloromethane in ethyl acetate to give the title compound (1.47 g, 44%) as an orange solid.

$^1$HNMR (400 MHz, CDCl$_3$): δ 3.77 (s, 3H), 3.78 (m, 3H), 5.23 (s, 2H), 6.43-6.41 (m, 2H), 6.98 (t, 1H), 7.16-7.14 (dd, 1H), 7.20 (d, 1H), 8.12 (t, 1H), 8.49 (d, 1H), 8.79 (s, 1H).
$^{19}$FNMR (376 MHz, CDCl$_3$) δ −105.97 (F), −100.64 (F). LCMS Rt=3.51 minutes, no mass ion seen.

PREPARATION 111

N-(2,4-dimethoxybenzyl)pyrimidin-4-amine

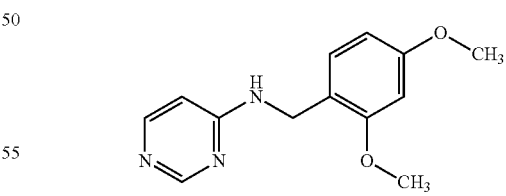

6-Chloro-N-(2,4-dimethoxybenzyl)pyrimidin-4-amine (Preparation 112, 3.46 g, 12.39 mmol) was dissolved in ethanol (140 mL). The solution was degassed and then 10% palladium on carbon (0.98 g) was added followed by ammonium formate (4.55 g, 72.15 mmol) and the reaction was heated at 80° C. for 2 hours. The reaction was cooled to room temperature, filtered through pad of Celite™ and the filtrate was concentrated in vacuo. The residue was partitioned between dichloromethane (30 mL) and water (15 mL). The organic layer was separated, dried over anhydrous MgSO₄, filtered and evaporated to give the title compound (2.94 g, 97%) as viscous oil.

¹HNMR (400 MHz, CDCl₃): δ 3.79 (s, 3H), 3.81 (m, 3H), 4.43 (br s, 2H), 5.55 (br s, 1H), 6.32 (d, 1H), 6.45-6.41 (m, 2H), 7.15 (d, 1H), 8.12 (d, 1H), 8.51 (s, 1H).

LCMS Rt=1.50 minutes, m/z 246 [MH]⁺.

PREPARATION 112

6-Chloro-N-(2,4-dimethoxybenzyl)pyrimidin-4-amine

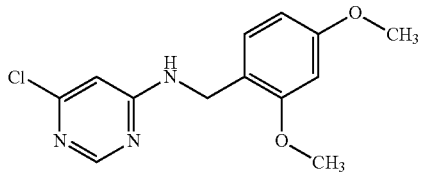 [SMILES: COc1ccc(CNc2cc(Cl)ncn2)c(OC)c1]

N,N-Diisopropylethylamine (8.10 mL, 46.50 mmol) and 2,4-dimethoxybenzylamine (2.52 mL, 16.78 mmol) were added to a solution of 4,6-dichloropyrimidine (2.50 g, 16.78 mmol) in butanol (80 mL) and reaction mixture was heated at 100° C. for 2 hours. The reaction mixture was cooled to room temperature and washed with water (30 mL). The aqueous layer was extracted with ethyl acetate (30 mL) and the combined organic layers were dried over anhydrous MgSO₄, filtered and evaporated. The residue was triturated in heptane to give the title compound (4.00 g, 85%) as a solid.

¹HNMR (400 MHz, CDCl₃): δ 3.80 (s, 3H), 3.83 (m, 3H), 4.40 (br s, 2H), 6.47-6.36 (m, 3H), 7.16 (d, 1H), 8.31 (s, 1H).

LCMS Rt=2.87 minutes, m/z 278 [M−H]⁻.

PREPARATION 113 tert-Butyl 4-{4-[4-(2-chloro-4-{[(2,4-dimethoxybenzyl)(1,3,4-thiadiazol-2-yl)amino]sulfonyl}-5-fluorophenoxy)-4'-(trifluoromethyl)biphenyl-3-yl]pyridin-2-yl}piperazine-1-carboxylate

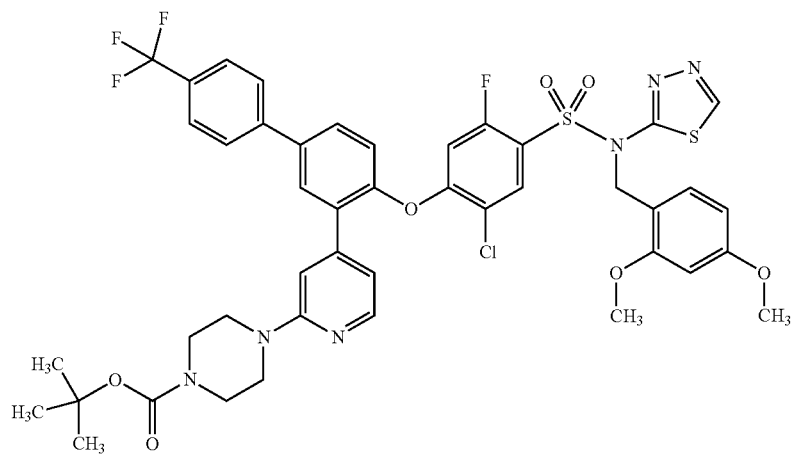 [SMILES: COc1ccc(CN(c2nncs2)S(=O)(=O)c2cc(Cl)c(Oc3ccc(-c4ccc(C(F)(F)F)cc4)cc3-c3ccnc(N4CCN(C(=O)OC(C)(C)C)CC4)c3)cc2F)c(OC)c1]

tert-Butyl 4-(4-(4-hydroxy-4'-(trifluoromethyl)biphenyl-3-yl)pyridin-2-yl)piperazine-1-carboxylate (Preparation 114, 200 mg, 0.400 mmol) was dissolved in dimethyl sulfoxide (3 mL) and potassium carbonate (110 mg, 0.800 mmol) was added followed by 5-chloro-N-(2,4-dimethoxybenzyl)-2,4-difluoro-N-(1,3,4-thiadiazol-2-yl)benzenesulfonamide (Preparation 16, 185 mg, 0.400 mmol). The reaction was stirred at room temperature for 18 hours and then partitioned between ethyl acetate (10 mL) and water (5 mL). The organic layer was separated and washed with brine (5 mL), dried over anhydrous MgSO₄, filtered and concentrated in vacuo. The residue was purified on silica gel by Biotage™ (7% to 60% ethyl acetate in heptane over 20 CV) to give the title product (340 mg, 90%) as a yellow foam.

¹HNMR (400 MHz, CDCl₃): δ 1.40 (s, 9H), 3.40 (m, 8H), 3.60 (s, 3H), 3.70 (s, 3H), 5.20 (s, 2H), 6.20 (s, 1H), 6.30 (m, 2H), 6.75 (d, 1H), 6.80 (s, 1H), 7.20 (m, 2H), 7.50-7.90 (m, 7H), 8.20 (d, 1H), 8.80 (s, 1H).

¹⁹F NMR (376 MHz, CDCl₃): δ −105.0, −63.0

LCMS Rt=3.26 minutes, MS m/z 941 [MH]⁺.

PREPARATION 114 tert-Butyl 4-(4-(4-hydroxy-4'-(trifluoromethyl)biphenyl-3-yl)pyridin-2-yl)piperazine-1-carboxylate tert-Butyl 4-(4-(4-(benzyloxy)-4'-(trifluoromethyl)biphenyl-3-yl)pyridin-2-yl)piperazine-1-carboxylate (Preparation 115, 1.30 g, 2.20 mmol) was dissolved in ethanol (20 mL) at room temperature and palladium hydroxide on activated charcoal (130 mg) was added. The reaction mixture was heated at 60° C. under a hydrogen atmosphere (50 psi) for 18 hours. The mixture was then filtered through a pad of Celite™, rinsed with ethanol and concentrated in vacuo. The residue was purified on silica gel by Biotage (5% to 60% ethyl acetate in heptane over 20 CV). Further purification by reverse phase using acetonitrile/water (5/95-95/5) with 0.1% formic acid as eluent gave the title compound (650 mg, 59%) as a white powder.

¹HNMR (400 MHz, CDCl₃): δ 1.49 (s, 9H), 3.59 (m, 8H), 6.75 (s, 1H), 6.79 (d, 1H), 7.08 (d, 1H), 7.48 (s, 1H), 7.53 (d, 1H), 7.60 (m, 4H), 8.30 (d, 1H).

¹⁹FNMR (376 MHz, CDCl₃): δ −62.41

LCMS Rt=2.93 minutes, MS m/z 500 [MH]⁺.

PREPARATION 115 tert-Butyl 4-(4-(4-(benzyloxy)-4'-(trifluoromethyl)biphenyl-3-yl)pyridin-2-yl)piperazine-1-carboxylate

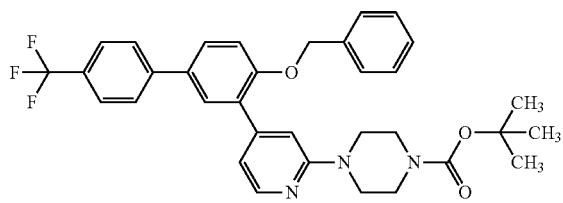 [SMILES: CC(C)(C)OC(=O)N1CCN(c2cc(-c3cc(-c4ccc(C(F)(F)F)cc4)ccc3OCc3ccccc3)ccn2)CC1]

tert-Butyl 4-(4-(2-(benzyloxy)-5-chlorophenyl)pyridin-2-yl)piperazine-1-carboxylate (Preparation 116, 1.10 g, 2.29 mmol), 4-(trifluoromethyl)phenylboronic acid (866 mg, 4.58 mmol), di-μ-chlorobis[5-chloro-2-[(4-chlorophenyl)(hydroxyimino)methyl]phenyl]palladium (II) dimer (93 mg, 0.114 mmol), tri-tert-butylphosphonium tetrafluoroborate (66 mg, 0.228 mmol), potassium carbonate (635 mg, 4.60 mmol) and tetrabutyl ammonium hydroxide (1M in methanol, 0.46 mL, 0.46 mmol) were combined in a microwave vial. Dimethylformamide (12 mL) was added and the vial was sealed. The mixture was heated at 130° C. for 2 hours in a microwave and then partitioned between ethyl acetate (15 mL) and water (5 mL). The organic layer was separated, washed with brine (5 mL), dried over anhydrous MgSO₄, filtered and concentrated in vacuo. The residue was dissolved in dimethylformamide (12 mL) and 4-(trifluoromethyl)phenylboronic acid (866 mg, 4.58 mmol), di-mu-chlorobis[5-chloro-2-[(4-chlorophenyl)(hydroxyimino)methyl]phenyl] palladium (II) dimer (93 mg, 0.114 mmol), tri-tert-butylphosphonium tetrafluoroborate (66 mg, 0.228 mmol), potassium carbonate (635 mg, 4.60 mmol) and tetrabutyl ammonium hydroxyde (1M in methanol, 0.46 mL, 0.46 mmol) were added. The mixture was heated at 130° C. for 1 hour in microwave and then partitioned between ethyl acetate and water. The organic layer was washed with brine, dried over anhydrous magnesium sulfate and concentrated in vacuo. The oil residue was purified on silica gel by Biotage (5% to 80% ethyl acetate in heptane over 20 CV) to give the title compound as a white solid (655 mg, 48%).

1HNMR (400 MHz, CDCl3): δ 1.40 (s, 9H), 3.50 (m, 8H), 5.10 (s, 2H), 6.85 (m, 2H), 7.15 (d, 1H), 7.30 (m, 4H), 7.60 (m, 2H), 7.65-7.80 (m, 5H), 8.20 (d, 1H).

LCMS Rt=3.05 minutes, MS m/z 590 [MH]⁺.

PREPARATION 116 tert-Butyl 4-(4-(2-(benzyloxy)-5-chlorophenyl)pyridin-2-yl)piperazine-1-carboxylate

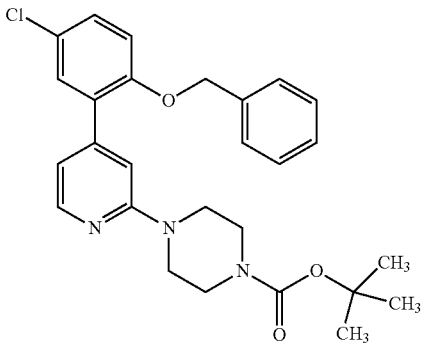 [SMILES: CC(C)(C)OC(=O)N1CCN(c2cc(-c3cc(Cl)ccc3OCc3ccccc3)ccn2)CC1]

tert-Butyl 4-(4-(5-chloro-2-hydroxyphenyl)pyridin-2-yl)piperazine-1-carboxylate (Preparation 117, 1.85 g, 4.755 mmol) was dissolved in dimethylformamide (10 mL) at room temperature under a nitrogen atmosphere. Potassium carbonate (1.31 g, 9.51 mmol) was added and the mixture was stirred for 10 minutes. Benzyl bromide (0.622 mL, 5.23 mmol) was added dropwise and the reaction mixture was heated at 60° C. for 18 hours and then partitioned between ethyl acetate (40 mL) and water (20 mL). The organic layer was separated and washed with brine (20 mL), dried over anhydrous MgSO₄, filtered and concentrated in vacuo to give the title compound (2.20 g, 96%) as a light yellow solid.

¹H NMR (400 MHz, CDCl₃): δ 1.45 (s, 9H), 3.40 (m, 4H), 3.50 (m, 4H), 5.05 (s, 2H), 680 (m, 2H), 6.95 (d, 1H), 7.20-7.40 (m, 7H), 8.20 (d, 1H).

LCMS Rt=3.56 minutes MS m/z 480 [MH]⁺.

PREPARATION 117 tert-Butyl 4-(4-(5-chloro-2-hydroxyphenyl)pyridin-2-yl)piperazine-1-carboxylate

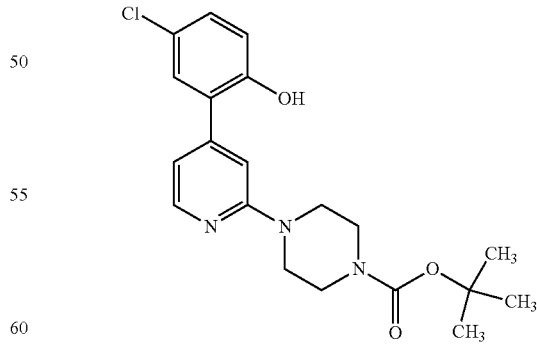

tert-Butyl 4-(4-bromopyridin-2-yl)piperazine-1-carboxylate (1.00 g, 2.66 mmol), 5-chloro-2-hydroxyphenylboronic acid (458 mg, 2.66 mmol) and sodium carbonate (1.13 g, 10.64 mmol) were combined and dissolved in a mixture of dioxane/water (14 mL/4 mL). The reaction mixture was degassed for 20 min with nitrogen and then tetrakistriphenylphosphinepalladium (0) (153 mg, 0.133 mmol) was added. The reaction mixture was heated at 70° C. for 18 hours and then partitioned between ethyl acetate (20 mL) and water (10 mL). The organic layer was separated, washed with brine (10 mL), dried over anhydrous MgSO$_4$, filtered and concentrated in vacuo. The residue was purified on silica gel by Biotage™ (10% to 60% ethyl acetate in heptane over 20 CV) to give the title compound (700 mg, 66%) as a white solid.

$^1$H NMR (400 MHz, CD$_3$OD): δ 1.40 (s, 9H), 3.50 (s, 8H), 6.80-6.90 (m, 2H), 6.95 (s, 1H), 7.15 (d, 1H), 7.30 (s, 1H), 8.05 (d, 1H).

LCMS Rt=2.48 minutes MS m/z 388 [M−H]$^−$.

PREPARATION 118

5-Chloro-4-[(3'-cyano-3-pyridazin-4-ylbiphenyl-4-yl)oxy]-N-(2,4-dimethoxybenzyl)-2-fluoro-N-1,3,4-thiadiazol-2-ylbenzenesulfonamide

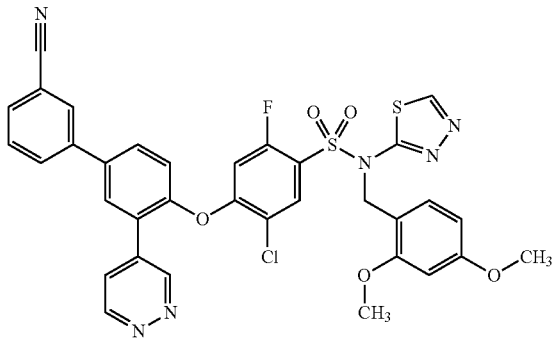 [SMILES: COc1ccc(CN(c2nncs2)S(=O)(=O)c2cc(Cl)c(Oc3ccc(-c4cccc(C#N)c4)cc3-c3ccnnc3)cc2F)c(OC)c1]

4'-Hydroxy-3'-(pyridazin-4-yl)biphenyl-3-carbonitrile (Preparation 119, 330 mg, 1.21 mmol) and potassium carbonate (334 mg, 2.42 mmol) were dissolved in dimethylsulfoxide (7 mL). Then 5-chloro-N-(2,4-dimethoxybenzyl)-2,4-difluoro-N-(1,3,4-thiadiazol-2-yl)benzenesulfonamide (Preparation 16, 558 mg, 1.21 mmol) was added and the reaction was stirred at room temperature for 2 hours. Water (15 mL) and ethyl acetate (25 mL) were added and the two layers were separated. The organic layer was dried over anhydrous MgSO$_4$, filtered and concentrated in vacuo. The residue was purified by flash chromatography on silica gel eluting with 10% dichloromethane in ethyl acetate to give the title compound (561 mg, 65%).

LCMS Rt=3.57 minutes, MS m/z 715 [MH]$^+$.

$^1$HNMR (400 MHz, CDCl$_3$): δ 3.69 (s, 3H), 3.75 (s, 3H), 5.30 (s, 2H), 6.26 (s, 1H), 6.36 (d, 1H), 6.55 (d, 1H), 7.18 (d, 1H), 7.26 (d, 1H), 7.63 (t, 1H), 7.74-7.70 (m, 4H), 7.85 (d, 2H), 7.89 (s, 1H), 8.82 (s, 1H), 9.28 (d, 1H), 9.47 (s, 1H).

$^{19}$FNMR (376 MHz, CDCl$_3$): δ −104.24 (s, 1 F)

PREPARATION 119

4'-hydroxy-3'-pyridazin-4-ylbiphenyl-3-carbonitrile

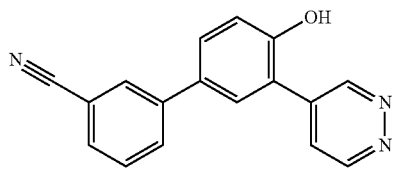 [SMILES: N#Cc1cccc(-c2ccc(O)c(-c3ccnnc3)c2)c1]

A mixture of 4'-hydroxy-3'-iodobiphenyl-3-carbonitrile (Preparation 120, 715 mg, 2.23 mmol), 4-(tributylstannyl)pyridazine (904 mg, 2.45 mmol) and cesium fluoride (677 mg, 4.46 mmol) in N,N-dimethylformamide (5 mL) was degassed under nitrogen. Then tetrakistriphenylphosphinepalladium (0) (258 mg, 0.22 mmol) and copper (I) iodide (85 mg, 0.45 mmol) were added, the reaction mixture was further degassed and then heated at 60° C. for 4 hours. The cooled reaction mixture was quenched with 10% ammonia (0.88M) in water (10 mL), diluted with ethyl acetate (20 mL) and then the mixture was stirred for 20 minutes. The resulting mixture was further diluted with ethyl acetate (10 mL) and the layers were separated. The organic layer was dried over anhydrous MgSO$_4$, filtered and the filtrate was concentrated in vacuo. The residue was purified by flash chromatography on silica gel eluting with 10% dichloromethane in ethyl acetate to give the title compound (355 mg, 55%).

LCMS Rt=2.54 minutes, MS m/z 274 [MH]$^+$.

$^1$HNMR (400 MHz, d-6DMSO): δ 7.11 (d, 1H), 7.61 (t, 1H), 7.75-7.70 (m, 2H), 7.89 (d, 1H), 8.05-8.00 (m, 2H), 8.24 (d, 1H), 9.25 (d, 1H), 9.59 (s, 1H), 10.51 (s, 1H).

PREPARATION 120

4'-Hydroxy-3'-iodobiphenyl-3-carbonitrile

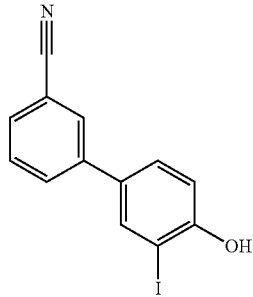 [SMILES: N#Cc1cccc(-c2ccc(O)c(I)c2)c1]

4'-Hydroxybiphenyl-3-carbonitrile (Preparation 121, 570 mg, 2.92 mmol) was dissolved in dichloromethane (10 mL) and acetic acid (10 mL). Then concentrated sulfuric acid (0.30 mL) and N-iodosuccinimide (657 mg, 2.92 mmol) were added at 0° C. (ice-bath cooling) and the reaction was allowed to warm to room temperature over 2 hours. The mixture was partitioned between ethyl acetate (30 mL) and water (15 mL). The organic layer was separated and dried over anhydrous MgSO$_4$, filtered and the filtrate was concentrated in vacuo. The residue was purified by flash chromatography on silica gel eluting with 50% ethyl acetate in heptane to give the title compound (720 mg, 77%).

LCMS Rt=3.16 minutes, MS m/z 320 [M−H]$^−$.

$^1$HNMR (400 MHz, CDCl$_3$): δ 5.41 (s, 1H), 7.08 (d, 1H), 7.46-7.44 (m, 1H), 7.54-7.50 (m, 1H), 7.62-7.59 (m, 1H), 7.74-7.71 (m, 1H), 7.78 (s, 1H), 7.86 (d, 1H).

PREPARATION 121

4'-Hydroxybiphenyl-3-carbonitrile

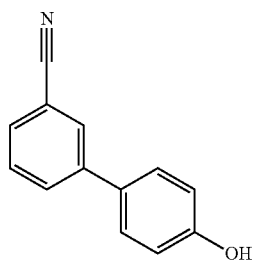 [SMILES: N#Cc1cccc(-c2ccc(O)cc2)c1]

3-Cyanophenylboronic acid (1.18 g, 8.03 mmol), 4-bromophenol (1.16 g, 6.69 mmol) and sodium carbonate (2.12 g, 20.07 mmol) were dissolved in dioxane (20 mL) and water (8 mL) and the reaction mixture was degassed under nitrogen. Tetrakistriphenylphosphinepalladium (0) (0.77 g, 0.67 mmol) was added and the reaction was stirred at 110° C. for 2 hours. The mixture was cooled to room temperature, filtered through pad of Arbocel™ and the filtrate was concentrated in vacuo. The residue was partitioned between ethyl acetate (30 mL) and water (15 mL). The organic layer was dried over anhydrous magnesium sulphate, filtered and the filtrate was concentrated in vacuo. The residue was purified by flash chromatography on silica gel eluting with 40% ethyl acetate in heptane to give the title compound as a pale yellow solid (0.58 g, 44%).

LCMS Rt=2.81 minutes, m/z mass ion not detected
$^{1}$HNMR (400 MHz, CDCl$_3$): δ 4.97 (s, 1H), 6.95 (d, 2H), 7.46 (d, 2H), 7.59-7.49 (m, 2H), 7.75 (d, 1H), 7.81 (s, 1H).

PREPARATION 122 tert-butyl 4-{4-[4-(2-chloro-4-{[(2,4-dimethoxybenzyl)(pyrimidin-2-yl)amino]sulfonyl}-5-fluorophenoxy)-4'-(trifluoromethyl)biphenyl-3-yl]pyridin-2-yl}piperazine-1-carboxylate

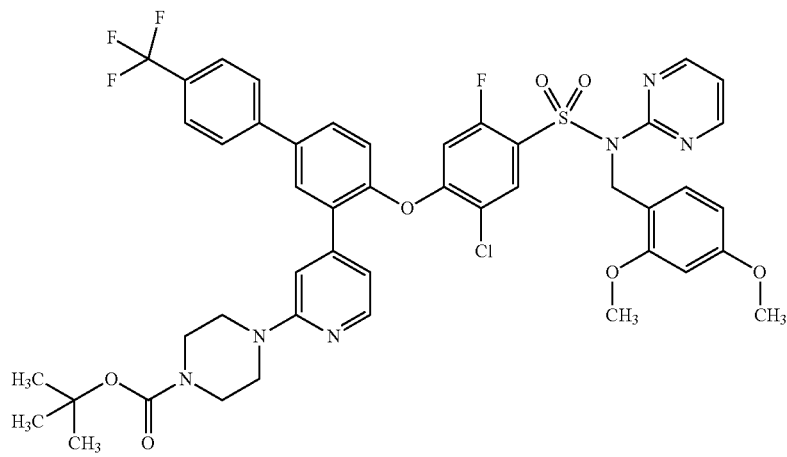 [SMILES: COc1ccc(CN(c2ncccn2)S(=O)(=O)c2cc(Cl)c(Oc3ccc(-c4ccc(C(F)(F)F)cc4)cc3-c3ccnc(N4CCN(C(=O)OC(C)(C)C)CC4)c3)cc2F)c(OC)c1]

tert-Butyl 4-(4-(4-hydroxy-4'-(trifluoromethyl)biphenyl-3-yl)pyridin-2-yl)piperazine-1-carboxylate (Preparation 114, 240 mg, 0.480 mmol) was dissolved in dimethyl sulfoxide (3 mL) and then potassium carbonate (133 mg, 0.962 mmol) followed by 5-chloro-N-(2,4-dimethoxybenzyl)-2,4-difluoro-N-(pyrimidin-2-yl)benzenesulfonamide (Preparation 13, 219 mg, 0.480 mmol) were added. The reaction mixture was stirred at room temperature for 20 hours. The reaction was then partitioned between ethyl acetate (15 mL) and 2M HCl (5 mL). The organic layer was separated and dried over anhydrous MgSO$_4$, filtered and evaporated. The residue was purified by flash chromatography on silica gel (gradient: 5-60% ethyl acetate in heptane) to give the title compound (380 mg, 84%) as a yellow foam.

$^{1}$HNMR (400 MHz, CDCl$_3$): δ 1.49 (s, 9H), 3.55 (br s, 8H), 3.76 (s, 6H), 5.38 (s, 2H), 6.44-6.36 (m, 3H), 6.75 (dd, 1H), 6.84 (s, 1H), 6.90 (t, 1H), 7.22-7.18 (m, 2H), 7.75-7.65 (m, 6H), 8.13-8.10 (m, 2H), 8.40 (d, 2H)
$^{19}$FNMR (376 MHz, CDCl$_3$): δ −107.11 (F), −62.50 (CF$_3$)
LCMS Rt=4.41 minutes, m/z 935 [MH]$^+$.

The ability of the compounds of formula (I) to block the Nav1.7 (or SCN9A) channel were measured using the assay described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 µg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 pg/ml G-418 in an incubator at 37° C. with a humidified atmosphere of 10% CO$_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM CaCl$_2$, 5.4 mM KCl, 1 mM MgCl$_2$, 10 mM glucose, and 10 mM HEPES, pH 7.4, with NaOH. Pipettes were filled with an intracellular solution of the following composition: 135 mM CsF, 5 mM CsCl, 2 mM MgCl$_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents. The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V1/2). Compounds were tested for their ability to inhibit hSCN9A sodium channels by activating the channel with a 20 msec voltage step to 0 mV following an 8 second conditioning prepulse to the empirically determined V1/2. Compound effect (% inhibition) was determined by difference in current amplitude before and after application of test compounds. For ease of comparison, "estimated IC-50" ($EIC_{50}$) values were calculated from single point electrophysiology data by the following equation, (tested concentration, uM)×(100-% inhibition/% inhibition). Inhibition values <20% and >80% were excluded from the calculation.

Electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of $1 \times 10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V1/2 and current was activated by a 20 msec voltage step to 0 mV.

Electrophysiological assays may also be conducted using the Ionworks Quattro automated electrophysiological platform (Molecular Devices Corp). Intracellular and extracellular solutions were as described above with the following changes, 100 µg/ml amphotericin was added to the intracellular solution to perforate the membrane and allow electrical access to the cells. hSCN9A cells were grown and harvested as for PatchXpress and cells were resuspended in extracellular solution at a concentration of $3-4 \times 10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

Compounds of the Examples were tested in the assay described above using the PatchXpress platform and found to have the Nav1.7 $EIC_{50}$ (uM) values specified in the table below.

| Ex | $EIC_{50}$ |
|---|---|
| 1 | 0.0018 |
| 2 | 0.0081 |
| 3 | 0.031 |
| 4 | 0.0029 |
| 5 | 0.0013 |
| 6 | 0.0029 |
| 7 | 0.0012 |
| 8 | 0.032 |
| 9 | 0.0116 |
| 10 | 0.0530 |
| 11 | 0.0077 |
| 12 | 0.0019 |
| 13 | 0.0022 |
| 14 | 0.0011 |
| 15 | 0.0060 |
| 16 | 0.0015 |
| 17 | 0.0027 |
| 18 | 0.018 |
| 19 | 0.011 |
| 20 | 0.24 |
| 21 | 0.10 |
| 22 | 0.033 |
| 23 | 0.0051 |
| 24 | 0.0017 |
| 25 | 0.0008 |
| 26 | 0.0023 |
| 27 | 0.0009 |
| 28 | 0.0009 |
| 29 | 0.0008 |
| 30 | 0.023 |
| 31 | 0.016 |
| 32 | 0.0053 |
| 33 | 0.016 |
| 34 | 0.0005 |
| 35 | 0.0022 |
| 36 | 0.011 |
| 37 | 0.012 |
| 38 | 0.018 |
| 39 | 0.0077 |
| 40 | 0.001 |

The ability of compounds of formula (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated IC50s are determined at the half inactivation for Nav1.5. These results can be compared to the $EIC_{50}$ value at the Nav1.7 channel to determine the selectivity of a given compound for Nav1.7 vs Nav1.5.

We claim:

1. A compound of formula (I):

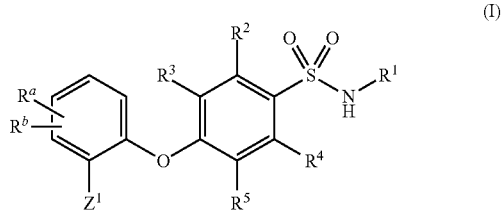

or a pharmaceutically acceptable salt thereof, wherein:
$R^1$ is a 'C-linked' 5- or 6-membered heteroaryl comprising one or two nitrogen atoms, wherein said heteroaryl is optionally substituted on a ring carbon atom by F or Cl; or
$R^1$ is a 'C-linked' 5-membered heteroaryl comprising one or two nitrogen atoms and one sulphur atom, wherein said heteroaryl is optionally substituted on a ring carbon atom by F or Cl;

$R^2$, $R^3$ and $R^4$ are independently H, F, Cl or —OCH$_3$;

$R^5$ is CN, F, Cl or $R^6$;

$R^a$ is phenyl optionally substituted by one to three substituents that are independently F, Cl, CN, H$_2$N(C$_1$-C$_4$)alkylene-, (C$_1$-C$_4$)alkylNH(C$_1$-C$_4$)alkylene-, (C$_3$-C$_8$)cycloalkyl or $R^6$; or $R^a$ is a 'C-linked' 5- or 6-membered heteroaryl comprising one or two nitrogen atoms, wherein said heteroaryl is optionally substituted by $R^7$ or $R^8$, or both $R^7$ and $R^8$;

$R^b$ is H, F, Cl, CN or $R^6$;

$R^6$ is (C$_1$-C$_4$)alkyl or (C$_1$-C$_4$)alkyloxy, each optionally substituted by one to eight F;

$Z^1$ is phenyl optionally substituted by one to three substituents that are independently F, Cl or $R^6$; or $Z^1$ is a 'C-linked' 5- or 6-membered heteroaryl comprising one or two nitrogen atoms, wherein said heteroaryl is optionally substituted by $R^7$ or $R^8$, or both $R^7$ and $R^8$;

$R^7$ is attached to a $Z^1$ ring carbon and is F, Cl, NR$^9$R$^{10}$, $R^6$, (C$_3$-C$_8$)cycloalkyl or Het';

$R^8$ is attached to a $Z^1$ ring nitrogen and is (C$_1$-C$_4$)alkyl or (C$_3$-C$_8$)cycloalkyl, each optionally substituted by, one to three F; or $R^8$ is attached to a $Z^1$ ring nitrogen and is a 'C-linked' Het$^1$;

Het$^1$ *is a* 3- to 8-membered saturated monoheterocycloalkyl comprising one or two ring members selected from —N(R$^{11}$)— and —O—, wherein said monoheterocycloalkyl is optionally substituted on a ring carbon atom by one to three substituents that are independently F, (C$_1$-C$_6$)alkyl, (C$_1$-C$_4$)alkyloxy(C$_o$-C$_4$)alkylene or (C$_3$-C$_8$)cycloalky; and .

$R^9$, $R^{10}$ and $R^{11}$ are independently H, (C$_1$-C$_6$)alkyl or (C$_3$-C$_8$)cycloalkyl; or, when Het$^1$ is 'N-linked', $R^{11}$ is absent from that nitrogen atom.

2. The compound according to claim 1 of the following formula:

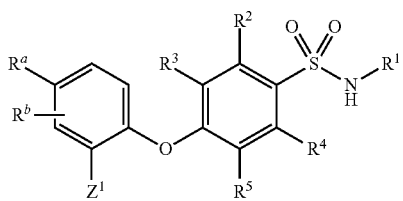

or a pharmaceutically acceptable salt thereof, wherein:

$R^1$ is a 'C-linked' 5- or 6-membered heteroaryl comprising one or two nitrogen atoms, wherein said heteroaryl is optionally substituted on a ring carbon atom by F or Cl; or $R^1$ is a 'C-linked' 5-membered heteroaryl comprising one or two nitrogen atoms and one sulphur atom, wherein said heteroaryl is optionally substituted on a ring carbon atom by F or Cl;

$R^2$, $R^3$ and $R^4$ are independently H, F, Cl or —OCH$_3$;

$R^5$ is CN, F, Cl or $R^6$;

$R^a$ is phenyl optionally substituted by one to three substituents that are independently from F, Cl or $R^6$;

$R^b$ is H, F, Cl or $R^6$;

$R^6$ is (C$_1$-C$_4$)alkyl or (C$_1$-C$_4$)alkyloxy, each optionally substituted by one to three F;

$Z^1$ is phenyl optionally substituted by one to three substituents that are independently F, Cl or $R^6$; or $Z^1$ is a 'C-linked' 5- or 6-membered heteroaryl comprising one or two nitrogen atoms, wherein said heteroaryl is optionally substituted by $R^7$ or $R^8$, or both $R^7$ and $R^8$;

$R^7$ is attached to a $Z^1$ ring carbon and is F, Cl, NR$^9$R$^{10}$, $R^6$, (C$_3$-C$_8$)cycloalkyl or Het$^1$;

$R^8$ is attached to a $Z^1$ ring nitrogen and is (C$_1$-C$_4$)alkyl, (C$_3$-C$_8$)cycloalkyl or 'C-linked' Het$^1$;

Het$^1$ is a 3- to 8-membered saturated monoheterocycloalkyl comprising one or two ring members selected from —N(R$^{11}$)— and —O—, wherein said monoheterocycloalkyl is optionally substituted on a ring carbon atom by one to three substituents that are independently F, (C$_1$-C$_6$)alkyl, (C$_1$-C$_4$)alkyloxy(C$_o$-C$_4$)alkylene or (C$_3$-C$_8$)cycloalky; and $R^9$, $R^{10}$ and $R^{11}$ are independently H, (C$_1$-C$_6$)alkyl or (C$_3$-C$_8$)cycloalkyl; provided that when Het$^1$ is 'N-linked', $R^{11}$ is absent from that nitrogen atom.

3. The compound according to claim 2 wherein $R^1$ is a 'C-linked' heteroaryl selected from thiazolyl, thiadiazolyl, pyridazinyl or pyrimidinyl, wherein said heteroaryl is optionally substituted on a ring carbon atom by F or Cl.

4. The compound according to claim 2 wherein $R^1$ is a 'C-linked' heteroaryl selected from thiazolyl or thiadiazolyl, wherein said heteroaryl is optionally substituted on a ring carbon atom by F.

5. The compound according to claim 4 wherein $R^2$, $R^3$ and $R^4$ are independently H or F.

6. The compound according to claim 5 wherein $R^5$ is CN, F or Cl.

7. The compound according to claim 6 wherein $R^a$ is phenyl, optionally substituted by $R^6$.

8. The compound according claim 7 wherein $R^b$ is H.

9. The compound according to claim 8 wherein $Z^1$ is a 'C-linked' 5- or 6-membered heteroaryl comprising one or two nitrogen atoms, wherein said heteroaryl is optionally substituted by $R^7$ or $R^8$, or both $R^7$ and $R^8$.

10. The compound according claim 8 wherein $Z^1$ is a 'C-linked' 5- or 6-membered heteroaryl comprising one or two nitrogen atoms, wherein said heteroaryl being is optionally substituted by R8.

11. The compound according to claim 10 wherein said 'C-linked' 5- or 6-membered heteroaryl is pyrazolyl or pyridazinyl, wherein said heteroaryl is optionally substituted by $R^8$.

12. The compound according to claim 10 wherein said 'C-linked' 5- or 6-membered heteroaryl is pyridazinyl or pyrazolyl, wherein said pyrazolyl is optionally substituted by methyl or a 'C-linked' 3- to 4-membered saturated monoheterocycloalkyl comprising one —N((C$_1$-C$_2$)alkyl)- ring member.

13. A pharmaceutical composition comprising a compound according to claim 1, or a pharmaceutically acceptable salt thereof, and one or more pharmaceutically acceptable excipients.

14. The pharmaceutical composition according to claim 13 further comprising one or more additional therapeutic agents.

15. The compound according to claim 1 that is
3-Cyano-4-{[3-pyridazin-4-yl-3'-(trifluoromethyl)biphenyl-4-yl]oxy}-N-1,2,4-thiadiazol-5-ylbenzenesulfonamide;
5-Chloro-2-fluoro-4-{[3-pyridazin-4-yl-4'-(trifluoromethyl)biphenyl-4-yl]oxy}-N-pyrimidin-2-ylbenzenesulfonamide;
3-Chloro-N-pyridazin-3-yl-4-{[3-pyridazin-4-yl-4'-(trifluoromethyl)biphenyl-4-yl]oxy}benzenesulfonamide;
5-Chloro-2-fluoro-4-{[3-pyridazin-4-yl-2'-(trifluoromethyl)biphenyl-4-yl]oxy}-N-1,3,4-thiadiazol-2-ylbenzenesulfonamide;

5-Chloro-2-fluoro-4-{[3-pyridazin-4-yl-3'-(trifluoromethyl)biphenyl-4-yl]oxy}-N-1,3,4-thiadiazol-2-ylbenzenesulfonamide;
5-Chloro-2-fluoro-4-{[3-pyridazin-4-yl-4'-(trifluoromethyl)biphenyl-4-yl]oxy}-N-1,3,4-thiadiazol-2-ylbenzenesulfonamide;
3-Cyano-4-{[3-pyridazin-4-yl-4'-(trifluoromethyl)biphenyl-4-yl]oxy}-N-1,2,4-thiadiazol-5-ylbenzenesulfonamide;
3-Fluoro-4-{[3-(1-methyl-1H-pyrazol-5-yl)biphenyl-4-yl]oxy}-N-1,3-thiazol-2-ylbenzenesulfonamide;
3-Chloro-4-[(3-pyridazin-4-ylbiphenyl-4-yl)oxy]-N-1,3,4-thiadiazol-2-ylbenzenesulfonamide;
3-Cyano-4-[(3-pyridazin-4-ylbiphenyl-4-yl)oxy]-N-1,3,4-thiadiazol-2-ylbenzenesulfonamide;
5-Chloro-2-fluoro-4-[(3-pyridazin-4-ylbiphenyl-4-yl)oxy]-N-1,3,4-thiadiazol-2-ylbenzenesulfonamide;
3-Cyano-4-[(3-pyridazin-4-ylbiphenyl-4-yl)oxy]-N-1,2,4-thiadiazol-5-ylbenzenesulfonamide;
5-Chloro-2-fluoro-4-({3-[1-(1-methylazetidin-3-yl)-1H-pyrazol-5-yl]-2'-(trifluoromethyl)biphenyl-4-yl}oxy)-N-1,3,4-thiadiazol-2-ylbenzenesulfonamide;
5-Chloro-2-fluoro-4-({3-[1-(1-methylazetidin-3-yl)-1H-pyrazol-5-yl]-4'-(trifluoromethyl)biphenyl-4-yl}oxy)-N-1,3,4-thiadiazol-2-ylbenzenesulfonamide; -4-yl-loxy)-N-1,3,4-thiadiazol-2-ylbenzenesulfonamide;
3-Cyano-N-(5-fluoro-1,3-thiazol-2-yl)-4-{[3-(1-methyl-1H-pyrazol-5-yl)biphenyl-4-yl]oxy}benzenesulfonamide;
3-Cyano-4-{[3-(1-methyl-1H-pyrazol-5-yl)biphenyl-4-yl]oxy}-N-1,2,4-thiadiazol-5-ylbenzenesulfonamide;
3-Cyano-4-{[3-pyridazin-4-yl-2'-(trifluoromethyl)biphenyl-4-yl]oxy}-N-1,2,4-thiadiazol-5-ylbenzenesulfonamide;
3-Cyano-4-{[3'-methoxy-3-(1-methyl-1H-pyrazol-5-yl)biphenyl-4-yl]oxy}-N-(1,3-thiazol-2-yl)benzenesulfonamide;
3-Cyano-4-{[2'-methoxy-3-(1-methyl-1H-pyrazol-5-yl)biphenyl-4-yl]oxy}-N-(1,3-thiazol-2-yl)benzenesulfonamide;
3-Cyano-N-(5-fluoropyridin-2-yl)-4-{[3-(1-methyl-1H-pyrazol-5-yl)biphenyl-4-yl]oxy}benzenesulfonamide;
4-{[3'-(Aminomethyl)-3-(1-methyl-1H-pyrazol-5-yl)biphenyl-4-yl]oxy}-3-cyano-N-(1,3-thiazol-2-yl)benzenesulfonamide;
5-Chloro-2-fluoro-N-(5-fluoropyridin-2-yl)-4-{[3-(1-methyl-1H-pyrazol-5-yl)biphenyl-4-yl]oxy}benzenesulfonamide;
3-Cyano-4-({2'-[(methylamino)methyl]-3-(1-methyl-1H-pyrazol-5-yl)biphenyl-4-yl}oxy)-N-(1,3-thiazol-2-yl)benzenesulfonamide;
5-Chloro-4-{[2-chloro-4'-fluoro-5-(pyridazin-4-yl)biphenyl-4-yl]oxy}-2-fluoro-N-(1,3,4-thiadiazol-2-yl)benzenesulfonamide;
4-{[3-(3-Amino-1H-pyrazol-4-yl)-3'-(trifluoromethyl)biphenyl-4-yl]oxy}-5-chloro-2-fluoro-N-(1,3,4-thiadiazol-2-yl)benzenesulfonamide;
5-Chloro-4-{[2-chloro-3'-fluoro-5-(pyridazin-4-yl)biphenyl-4-yl]oxy}-2-fluoro-N-(1,3,4-thiadiazol-2-yl)benzenesulfonamide;
5-Chloro-4-{[2-chloro-2'-fluoro-5-(pyridazin-4-yl)biphenyl-4-yl]oxy}-2-fluoro-N-(1,3,4-thiadiazol-2-yl)benzenesulfonamide;
5-Chloro-4-{[2-chloro-5-(pyridazin-4-yl)-3'-(trifluoromethyl)biphenyl-4-yl]oxy}-2-fluoro-N-(1,3,4-thiadiazol-2-yl)benzenesulfonamide;
5-Chloro-4-{[4'-chloro-3-(pyridazin-4-yl)-3'-(trifluoromethyl)biphenyl-4-yl]oxy}-2-fluoro-N-(1,3,4-thiadiazol-2-yl)benzenesulfonamide;
5-Chloro-2-fluoro-4-{2-(pyridazin-4-yl)-4-[6-(trifluoromethyl)pyridin-3-yl]phenoxy}-N-(1,3,4-thiadiazol-2-yl)benzenesulfonamide;
5-Chloro-2-fluoro-4-{2-(pyridazin-4-yl)-4-[6-(trifluoromethyl)pyridin-2-yl]phenoxy}-N-(1,3,4-thiadiazol-2-yl)benzenesulfonamide;
4-{[3-(5-Amino-1H-pyrazol-4-yl)-3'-cyanobiphenyl-4-yl]oxy}-5-chloro-2-fluoro-N-(1,3,4-thiadiazol-2-yl)benzenesulfonamide;
5-Chloro-2-fluoro-4-{2-(pyridazin-4-yl)-4-[2-(trifluoromethyl)pyridin-4-yl]phenoxy}-N-(1,3,4-thiadiazol-2-yl)benzenesulfonamide;
5-Chloro-2-fluoro-4-({3-[2-(piperazin-1-yl)pyridin-4-yl]-4'-(trifluoromethyl)biphenyl-4-yl}oxy)-N-(1,3,4-thiadiazol-2-yl)benzenesulfonamide;
5-Chloro-2-fluoro-4-({3-[2-(piperazin-1-yl)pyridin-4-yl]-4'-(trifluoromethyl)biphenyl-4-yl}oxy)-N-(pyrimidin-4-yl)benzenesulfonamide;
5-Chloro-4-[(6-chloro-3'-fluoro-4-pyridazin-4-ylbiphenyl-3-yl)oxy]-2-fluoro-N-1,3,4-thiadiazol-2-ylbenzenesulfonamide;
5-Chloro-4-[(6-chloro-4'-fluoro-4-pyridazin-4-ylbiphenyl-3-yl)oxy]-2-fluoro-N-1,3,4-thiadiazol-2-ylbenzenesulfonamide;
5-Chloro-4-[(6-chloro-2'-fluoro-4-pyridazin-4-ylbiphenyl-3-yl)oxy]-2-fluoro-N-1,3,4-thiadiazol-2-ylbenzenesulfonamide;
5-chloro-4-[(3'-cyano-3-pyridazin-4-ylbiphenyl-4-yl)oxy]-2-fluoro-N-1,3,4-thiadiazol-2-ylbenzenesulfonamide;
5-chloro-2-fluoro-4-{[3-(2-piperazin-1-ylpyridin-4-yl)-4'-(trifluoromethyl)biphenyl-4-yl]oxy}-N-pyrimidin-2-ylbenzenesulfonamide;

or a ;pharmaceutically acceptable salt thereof.

* * * * *